US010829516B2

(12) United States Patent
Luyt et al.

(10) Patent No.: US 10,829,516 B2
(45) Date of Patent: Nov. 10, 2020

(54) PEPTIDOMIMETICS FOR IMAGING THE GHRELIN RECEPTOR

(71) Applicant: London Health Sciences Centre Research Inc., London (CA)

(72) Inventors: Leonard G. Luyt, London (CA); Milan Mrazek Fowkes, Abingdon (GB)

(73) Assignee: LONDON HEALTH SCIENCES CENTRE RESEARCH INC., London (CA)

( * ) Notice: Subject to any disclaimer, the term of this patent is extended or adjusted under 35 U.S.C. 154(b) by 0 days.

(21) Appl. No.: 15/578,105

(22) PCT Filed: May 27, 2016

(86) PCT No.: PCT/CA2016/050607
§ 371 (c)(1),
(2) Date: Nov. 29, 2017

(87) PCT Pub. No.: WO2016/191865
PCT Pub. Date: Dec. 8, 2016

(65) Prior Publication Data
US 2018/0155395 A1  Jun. 7, 2018

Related U.S. Application Data

(60) Provisional application No. 62/168,314, filed on May 29, 2015.

(51) Int. Cl.
| | | |
|---|---|---|
| *A61K 38/00* | (2006.01) | |
| *A61K 51/08* | (2006.01) | |
| *C07K 7/06* | (2006.01) | |
| *C07K 14/60* | (2006.01) | |
| *C07K 5/00* | (2006.01) | |
| *C07K 5/10* | (2006.01) | |
| *G01N 33/574* | (2006.01) | |
| *C07K 5/107* | (2006.01) | |
| *G01N 33/74* | (2006.01) | |
| *C07K 19/00* | (2006.01) | |

(52) U.S. Cl.
CPC .............. *C07K 7/06* (2013.01); *A61K 38/00* (2013.01); *A61K 51/08* (2013.01); *C07K 5/00* (2013.01); *C07K 5/1016* (2013.01); *C07K 5/1027* (2013.01); *C07K 14/60* (2013.01); *C07K 19/00* (2013.01); *G01N 33/57492* (2013.01); *G01N 33/74* (2013.01); *G01N 2333/71* (2013.01)

(58) Field of Classification Search
CPC ........ A61K 38/00; A61K 51/00; A61K 51/08; A61K 51/088; G01N 33/74; G01N 33/57492; G01N 2333/71; C07K 7/06; C07K 19/00; C07K 5/1016; C07K 5/1027; C07K 5/00; C07K 14/60

USPC .... 424/1.11, 61.65, 1.69, 9.1, 9.2, 9.6, 1.65, 424/9.3, 9.4; 530/300, 329, 330
See application file for complete search history.

(56) References Cited

U.S. PATENT DOCUMENTS

| | | | | |
|---|---|---|---|---|
| 5,798,337 A | * | 8/1998 | Somers | ................ C07D 209/20 514/11.2 |
| 7,094,869 B2 | * | 8/2006 | Somers | .................. A61K 38/25 514/11.2 |
| 2002/0111461 A1 | * | 8/2002 | Somers | .................. A61K 38/25 530/330 |

OTHER PUBLICATIONS

Fowkes, Peptidomimetic GHS-R1a Agonists as PET Imaging Agents for Prostate Cancer, pp. 1-153. (Year: 2014).*
Bowers, C. Y., et al. Mol. Endocrinol. Proc. 1977, 287-292.
Bowers, C. Y., et al. Endocrinology 1984, 114, 1537-1545.
Bowers, C. Y. J. Pediatr. Endocrinol. 1993, 6, 21-31.
Ilson, B. E., et al. Clin. Endocrinol. Metab. 1989, 69, 212-214.
Moulin, A., et al. Recent Developments in Ghrelin Receptor Ligands, ChemMedChem 2007, 2, 1242-1259.
Akman, M. S., et al. Endocrinology 1993, 132, 1286-1291.
Isidro, M. L., et al. High Throughput Screening 2006, 9, 175-180.
Smith, R. G., et al. Science 1993, 260, 1640-1643.
Conley, L. K., et al. Endocrine 1994, 2, 691-695.
Patchett, A. A., et al. Proc. Natl. Acad. Sci. 1995, 92, 7001-7005.
Deghenghi, R. et al. Life Sci. 1994, 54, 1321-1328.
Elias, K., et al. Endocrinology 1995, 136, 5694-5699.
Muccioli, G., et al. Endocr. Updates 2004, 23, 27-45.
Howard, A. D., et al. Science 1996, 273, 974-977.
Kojima, M.; et al. Nature 1999, 402, 656-660.
Bednarek, M. A.; et al. Structure—Function Studies on the New Growth Hormone-Releasing Peptide, Ghrelin: Minimal Sequence of Ghrelin Necessary for Activation of Growth Hormone Secretagogue Receptor 1a. J. Med. Chem. 2000, 43, 4370-4376.
Torsello, A.; et al. Endocrinology 2002, 143, 1968-1971.
Ye, Z.; et al. Modeling Directed Design and Biological Evaluation of Quinazolinones as Non-Peptidic Growth Hormone Secretagogues. Bioorg. Med. Chem. Lett. 2000, 10, 5-8.
Li, J. J.; et al. Bioorg. Med. Chem. Lett. 2008, 18, 2536-2539.
Tokunaga, T.; et al. Bioorg. Med. Chem. Lett. 2005, 15, 1789-1792.
Raun, K.; et al. Eur. J. Endocrinol. 1998, 139, 552-561.
Ankersen, M.; et al. A New Series of Highly Potent Growth Hormone-Releasing Peptides Derived from Ipamorelin. J. Med. Chem. 1998, 41, 3699-3704.
Hansen, T. K.; et al. J. Med. Chem. 1998, 41, 3705-3714.
Ankersen, M.; et al. Eur. J. Med. Chem. 1999, 34, 783-790.
Hansen, B.; et al. Eur. J. Endocrinol. 1999, 141, 180-189.
Peschke, B.; et al. Eur. J. Med. Chem. 1999, 34, 363-380.
Peschke, B.; et al. Bioorg. Med. Chem. Lett. 1999, 9, 1295-1298.
Ankersen, M.; et al. Eur. J. Med. Chem. 2000, 35, 487-497.
Peschke, B.; et al. Eur. J. Med. Chem. 2000, 35, 599-618.

(Continued)

*Primary Examiner* — D. L. Jones
(74) *Attorney, Agent, or Firm* — Eduardo Krupnik

(57) ABSTRACT

The present invention concerns compositions comprising and methods of identification and use of imaging agents. The imaging agents comprise a growth hormone secretagogues having a conjugated fluoride. The imaging agents of the present invention may be used for detection, diagnosis and/or staging of prostate or other forms of cancer, and may also be used for cardiac disease.

20 Claims, 45 Drawing Sheets

(56) References Cited

OTHER PUBLICATIONS

Hansen, T.; et al. Bioorg. Med. Chem. Lett. 2001, 11, 1915-1918.
Peschke, B.; et al. Eur. J. Med. Chem. 2002, 37, 487-501.
Muccioli, G.; et al. Eur. J. Pharmacol. 2002, 440, 235-254.
Broglio, F.; et al. Eur. J. Pharmacol. 2002, 448, 193-200.
Jeffery, P. L.; et al. J. Endocrinol. 2002, 172, R7-R11.
Lu, C.; et al. The Prostate 2012, 72, 825-833.
Jemal, A.; Siegel, R.; Xu, J.; Ward, E. CA Cancer J. Clin. 2010, 60, 277-300.
The Canadian Cancer Society Prostate Cancer Risks. http://www.cancer.ca/en/cancer-information/cancer-type/prostate/risks/?region=on (accessed May 25, 2013, 2013).
Seitz, M.; et al. Eur. Urol. 2009, 55, 801-814.
Kattan, M. W.; et al. J Natl Cancer Inst 1998, 90, 766-771.
Eifler, J. B.; et al. An updated prostate cancer staging nomogram (Partin tables) based on cases from 2006 to 2011. BJU Int 2013, 111, 22-29.
D'Amico, A. V.; et al. Biochemical Outcome After Radical Prostatectomy, External Beam Radiation Therapy, or Interstitial Radiation Therapy for Clinically Localized Prostate Cancer. JAMA 1998, 280, 969-974.
Gupta, R. T.; et al. Oncology (Williston Park) 2013, 27, 262-270.
Turkbey, B., et al. J Urol 2011, 186, 1818-1824.
Thormer, G.; et al. Eur Radiol 2012, 22, 1820-1828.
Jadvar, H. J. Nucl. Med 2011, 52, 81-89.
Fuchsjager, M.; et al. Acta Radiol 2008, 49, 107-120.
Schwarzenboeck, S.; et al. Choline PET and PET/CT in Primary Diagnosis and Staging of Prostate Cancer. Theranostics 2012, 2, 318-330.
Warburg, O. Science 1956, 123, 309-314.
Fanti, S.; PET in genitourinary tract cancers. Q J Nucl Med Mol Imaging 2007, 51, 260-271.
Kato, T.; et al. Eur. J. Nucl. Med. Mol. Imaging 2002, 29, 1492-1495.

* cited by examiner

LCE00210: H-Aib-His-D-2-Nal-D-Phe-Lys-NH₂

LCE00211: H-Aib-His-D-2-Nal-D-Phe-Lys(4-FB)-NH₂

LCE00217: H-Aib-His-D-2-Nal-D-Phe-Lys(AEEA-4-FB)-NH₂

LCE00239: H-His-D-Trp-Ala-Trp-D-Phe-Lys-NH₂

LCE00240: H-Ala-His-D-2-Nal-Ala-Trp-D-Phe-Lys-NH$_2$

LCE00243: H-Inp-D-2-Nal-D-2-Nal-Phe-Lys(4-FB)-NH2

LCE00244: H-Inp-D-2-Nal-D-2-Nal-1-Nal-Lys-NH2

LCE00246: H-Inp-His-D-2-Nal-D-2-Thi-Lys(4-FB)-NH₂

LCE00267: H-Aib-His-D-2-Nal-D-2-Thi-Lys(4-FB)-NH₂

LCE00268: H-Inp-His-D-2-Nal-D-Phe-Lys(4-FB)-NH₂

LCE00281: H-His-D-Trp-Ala-Trp-D-Phe-Dpr(4-FB)-NH₂

LCE00282: H-D-Ala-D-2-Nal-Ala-Trp-D-Phe-Lys-NH₂

LCE00295: H-Inp-D-2-Nal-D-2-Nal-Phe-Lys(2-FP)-NH₂

CE00210: H-Aib-His-D-2-Nal-D-Phe-Lys-NH₂

LCE00217: H-Aib-His-D-2-Nal-D-Phe-Lys(4-FB-AEEA)-NH₂

LCE00269: H-Inp-His-D-2-Nal-D-2-Nal-Lys(4-FB)-NH₂

LCE00295: H-Inp-D-2-Nal-D-2-Nal-Phe-Lys(2-FP)-NH$_2$

Ghrelin 1-28

LCE00210

LCE00211

LCE00239

LCE00240

LCE00243

LCE00244

LCE00245

LCE00267

LCE00268

LCE00269

LCE00270

LCE00272

LCE00281

TL-MF-5-2FP

TL-MF-4-2FP

PEPTIDOMIMETICS FOR IMAGING THE GHRELIN RECEPTOR

CROSS REFERENCE TO RELATED APPLICATIONS

This application is a national stage application under 35 U.S.C. 371 of International Application No. PCT/CA2016/050607, filed May 27, 2016, which in turn claims the benefit under 35 U.S.C. 119(e) of U.S. Provisional Ser. No. 62/168,314, filed May 29, 2015, the contents of each of which are hereby incorporated by reference into the present disclosure.

FIELD OF THE INVENTION

The present invention relates to peptidomimetics designed based upon growth hormone secretagogues (GHS) and their uses in imaging the ghrelin receptor, cancer cells and cardiomyocytes.

BACKGROUND OF THE INVENTION

In 1977, Bowers and co-workers studied enkephalin (EK) analogues in order to gain a better understanding of small peptide structure-activity relationships (SARs) and pituitary hormone secretion. [1] During the course of their research they found that certain enkephalin derivatives (such as DTrp$^2$-MetEKNH$_2$ for example) released growth hormone (GH) in vitro from the pituitary glands of female rats. [1] This eventually led them to discover the hexamer H-His-D-Trp-Ala-Trp-D-Phe-Lys-NH$_2$ in 1984, which represented the first synthetic peptide that released GH in vitro in rats and in vivo in a number of animals including lambs, rats, monkeys [2] and humans. [3] This compound was later termed growth hormone releasing peptide 6 (GHRP-6, compound 1 of FIG. 1A). In 1989, a paper by Ilson et al. [4] discussed the potential of these synthetic peptides to replace recombinant human growth hormone (rhGH) for the treatment of GH deficiency. [4] This form of therapy, however, is expensive and requires injection or inhalation of the recombinant hormone on a daily basis. [5]

Two second generation congeners of GHRP-6 were synthesized in 1993, GHRP-1 [6] and GHRP-2 [3] (compounds 2 and 3 respectively, FIG. 1A). These peptides were also found to release GH in vivo in humans. [3]

Growth hormone releasing peptides (GHRPs) belong to a class of compounds known as growth hormone secretagogues. [7] These are compounds that are specifically defined as molecules that stimulate the secretion of pituitary GH through a route different from that of GH releasing hormone (GHRH). [7] Between 1993 and 1995 a number of GHSs were synthesized by research teams with the aim of developing orally bioavailable drugs for treating GH deficiency. These included small molecules such as L692,429 [8] (Merck & Co.), EP-51389 [9] (Europeptides) and MK-0677 [10] (Merck & Co.), peptides such as hexarelin [11] (Mediolanum Farmaceutici) and peptidomimetics such as G-7039, G-7143, G-7203 and G-7502 [12] (all Genentech). In 1996 the group of R. Smith at the Merck Sharp & Dohme Research Laboratory (USA) identified the receptor that these compounds acted on through expression cloning methods. [13, 14] This receptor was termed the growth hormone secretagogue receptor type 1a and is predominantly expressed in the hypothalamus and pituitary, as well as in the thyroid gland, stomach, intestine, pancreas, spleen, ventricular myocardium, aorta, lung, adrenal gland, kidney, adipose tissue, testis, ovary and lymphocytes. [13]

The endogenous ligand for the GHS-R1a was isolated from the rat stomach by Kojima and co-workers, [15] thereby completing the cycle of reverse pharmacology. This ligand, termed "ghrelin" (compound 4 of FIG. 1B) is a 28 amino acid peptide with an n-octanoyl group on the Ser 3 side-chain that is important for binding to the GHS-R1a and releasing GH in vivo. [13] In addition, this acylation is also responsible for ghrelin's numerous biological activities, such as regulation of glucose metabolism, insulin release, gut motility and many others. [13] Since ghrelin is the endogenous ligand for the GHS-R1a, this receptor is also referred to as the ghrelin receptor.

Following the isolation of ghrelin, research shifted towards truncated ghrelin derivatives. This was carried out in order to identify the active pharmacophore of the peptide that is responsible for its biological activity. [16] Amongst these derivatives are peptide agonists 5-7 (FIG. 1B). Only the first four to five N-terminal amino acids of ghrelin (Gly-Ser-Ser-Phe/-Leu) were needed to bind to and activate the receptor. This is clearly indicated by the decrease in in vitro potency with decreasing number of N-terminal residues (FIG. 1B, cf. 5 to 6 to 7, EC50=11.5±2.3 nM, 72±29 nM and >10, 000 nM respectively). [16]

Unfortunately, these shortened ghrelin derivatives were incapable of releasing GH in vivo. [17] A wide range of different GHS-R1a agonists have been synthesized since the discovery of ghrelin. These encompass small molecule agonists described in [18], [19] and [20] as well as the extensive work on peptidomimetic and pseudo-peptide agonists disclosed in [21-31], whose structures possess some pharmacophoric similarities to the native ligand.

Other than treating GH deficiency, GHS-R1a agonists could also be developed for treating a variety of disorders such as anorexia nervosa [5, 32] and heart failure. [5, 33] Additionally, The GHS-R1a was recently found to be expressed in a number of prostate cancer cell lines such as ALVA-41, LNCaP, DU145 and PC3. [34] Development of GHS-R1a agonists that specifically target prostate cancer cells could provide a means to detect and visualize prostatic tumours in vivo through the use of a suitable imaging modality. This would enable an alternative means to image prostate cancer (PCa).

Prostate cancer (PCa) is the foremost male malignancy in North America. [35] In the US in 2010 it was estimated that prostate cancer represented 28% of all new cancer cases and 11% of all cancer deaths in men. [36] Despite the absence of a single cause for PCa, a number of potential risk factors do exist. [37] These include exposure to pesticides, inherited gene mutations and diets high in fat, processed meat and dairy products. [37] Clinical methods currently used to diagnose PCa involve a combination of the digital rectal examination (DRE), the serum prostate-specific antigen (PSA) test and transrectal ultrasound (TRUS)-guided biopsy. [38] These methods are not only used to predict the recurrence of tumours after radical prostatectomy [39] and the potential for cancer to spread from the prostate, [40] but also to divide patients into groups based on the risk of PCa reappearance after localized treatment. [41, 42] Despite the utility that these techniques provide, the presence of sampling error in TRUS-guided biopsies [42] coupled with patients who have consistently elevated levels of serum PSA in spite of negative prostate biopsies, [38] suggests that developing non-invasive imaging methods that improve disease identification at an earlier phase of illness is crucial. [42]

One such non-invasive technique for PCa diagnosis and staging is a combination of magnetic resonance imaging (MRI) and functional MRI methods such as diffusion-weighted MRI (DW-MRI), magnetic resonance spectroscopic imaging (MRSI) and dynamic contrast-enhanced MRI (DCE-MRI). [38] Briefly, these methodologies collect information on in vivo diffusion coefficients for biological tissues, metabolism and tissue vascularity respectively. [38] The combination of T2-weighted MRI and two or more functional techniques make up the multi-parametric prostate MRI (mpMRI) exam, which is currently a highly effective way to identify and localize PCa. [42] Despite the usefulness of the data gathered by functional MRI, it tends to suffer from difficult and lengthy procedures (MRSI), [42] limited lesion detection in the central gland, [43] the requirement for dedicated computer software for data analysis (DCE-MRI) [42] and the inability to specify cut-off values in apparent diffusion coefficients (ADC) in DW-MRI thus making the delineation between benign and malignant tumours problematic. [42, 44]

In addition to these factors, there are currently no guidelines available that can specify which functional sequence is most appropriate in a particular clinical scenario. [38]

Alternative imaging methods for diagnosing and staging PCa include computed tomography (CT) and positron emission tomography (PET). These two techniques are often used in tandem (FIG. 2B). Unfortunately, much like in the case of MRI, a number of limitations exist. The former imaging modality alone is unable to distinguish between benign and malignant prostatic tissue, [46] thereby restricting its use in detecting primary prostate cancer. [47] A combination of PET/CT using the radiotracer 18F-FDG enables tumour localization via the Warburg effect [45, 48] but suffers from renal excretion, thus masking possible prostatic tumours due to build-up of activity in the bladder. [47, 49] In addition to this, PET has a limited ability to distinguish between benign and malignant disease, despite the use of alternative radiotracers such as [$^{18}$F]fluorodihydrotestosterone (FDHT) [47], [11C]acetate, [50] [$^{11}$C]Choline [51] and [$^{11}$C]methionine. [47, 52] It is therefore clear that the development of novel imaging techniques to improve differentiation between benign and malignant prostatic tumours—as well as addressing the clinical issue of over-diagnosing prostate cancer and thus over-treating potentially benign tumours—is of paramount importance. [35] The GHS-R1a is known to have differential expression in breast carcinomas, ovarian tumours as well as in normal, benign and cancerous prostatic tissue. [35] Previous work within the Luyt group has shown that targeting the GHS-R1a expressed in PCa cell lines may enable non-invasive radionuclide imaging of prostate cancer. [35] This was indicated by the specificity of the peptidic imaging probe fluorescein-ghrelin(1-19) towards PCa, with low level association in benign prostatic hyperplasia (BPH) or normal prostatic tissue. [35] Targeting this receptor with peptidomimetic GHS-R1a agonists such as those tabulated in Table 2 could allow differentiation between BPH and PCa through PET imaging. By moving from the original peptide based fluorescein-ghrelin(1-19) to peptidomimetics, imaging agents with superior targeting, stability and pharmacokinetic properties should result.

In cardiomyocytes, ghrelin regulates signaling pathways that link to myocardial metabolism and cardiomyocyte growth and survival, thus indicating that ghrelin may play a vital role in the progression of cardiomyopathy.

SUMMARY OF THE INVENTION

The present invention relates to peptidomimetics designed based upon growth hormone secretagogues.

In one embodiment, the present invention relates to a growth hormone secretagogue (GHS) having a fluoride.

The present invention, in one embodiment, provides a conjugate including a peptidomimetic of a growth hormone secretagogue (GHS) having a conjugated fluoride group.

In one embodiment of the conjugate of the present invention, the peptidomimetic includes one or more unnatural amino acid residues.

In one embodiment of the conjugate of the present invention, the peptidomimetic includes a lysine residue and the fluoride group is conjugated to the lysine residue.

In one embodiment of the conjugate of the present invention, the fluoride is non-radioactive or radioactive.

In one embodiment of the conjugate of the present invention, the peptidomimetic having the conjugated fluoride is selected from H-Inp-D-2-Nal-D-2-Nal-Phe-Lys(4-FB)-NH2 and H-Inp-D-2-Nal-D-2-Nal-1-Nal-Lys(4-FB)-NH2.

In one embodiment of the conjugate of the present invention, the peptidomimetic having the conjugated fluoride is selected from H-Inp-(D-2-Nal)2-Ser-Phe-Lys(2-FP)-NH2, H-Inp-(D-2-Nal)2-Phe-Ser-Lys(2-FP)-NH2, H-Inp-(D-2-Nal)2-Tyr-Lys(2-FP)-NH2 and H-Inp-(D-2-Nal)2-Ser-Lys(2-FP)-NH2.

In another embodiment, the present invention relates to a method of detecting ghrelin receptors at a target site of a subject, the method including: (a) providing a conjugate comprising a peptidomimetic of a growth hormone secretagogue (GHS) having a conjugated fluoride group as per any of the previous embodiments; (b) administering the conjugate of step (a) to the subject in an amount effective to detect the growth hormone receptors at the target site; (c) allowing the conjugate to accumulate at the target site within the subject; and (d) detecting the conjugate at the target site thereby detecting the growth hormone receptors at the target site.

In one embodiment of the method of detecting ghrelin receptors at a target site of a subject, the target site is a tumor or cardiac tissue.

In one embodiment of the method of detecting ghrelin receptors at a target site of a subject, the detecting is performed with positron emission tomography (PET), PET-computed tomography (CT) hybrid or PET-magnetic resonance imaging (MRI) hybrid.

In another embodiment, the present invention relates to a method of assessing the malignancy of a tumor, the method including: (a) contacting the tumor with a conjugate as defined in any of the previous embodiments, (b) detecting the expression of the conjugate in the tumor, (c) comparing the expression of step (b) with the expression of said conjugate in a control tissue, and (d) assessing the malignancy of the tumor based on the comparison. In aspects, the detecting is performed with positron emission tomography (PET), PET-computed tomography (CT) hybrid or PET-magnetic resonance imaging (MRI) hybrid.

In another embodiment, the present invention is a use of the conjugate according to any one of the previous embodiments for imaging cancer cells and cardiac tissue.

In another embodiment, the present invention is a use of the conjugate according to any one of the previous embodiments for the treatment of GH deficiency, stimulate GH secretion from the pituitary, increase appetite, attenuate cachexia in patient with cancer or chronic obstructive pulmonary disease, suppressing ghrelin's orexigenic effects, treating obesity, regulating food intake, GI motility, gastric emptying, body weight, and treating ulcer or gastroparesis, treating anorexia nervosa, heart failure, diabetes mellitus (including Type 1 and 2) or diabetes mellitus complications, constipation and Parkinson's disease.

In another embodiment the present invention is a method of treating a disorder associated with the regulation of ghrelin receptor, the method including administering to a subject in need, an effective amount of a peptidomimentic of the present invention. In aspects, the disorder is selected from cachexia in patient with cancer or chronic obstructive pulmonary disease, heart failure, and diabetes mellitus (including Type 1 and 2).

In another embodiment, the present invention is a conjugate as defined in any one of previous embodiments for use in imaging a ghrelin receptor. In aspects, the ghrelin receptor is GHS-R1a.

In another embodiment, the present invention is a conjugate as defined in any one of the previous embodiments for use in imaging a ghrelin receptor.

In another embodiment, the present invention is a conjugate as defined in any one of the previous embodiments for use in imaging, diagnosing or staging cancer, and heart disease.

In another embodiment, the present invention is a pharmaceutical composition comprising a conjugate as defined in any of the previous embodiments, and a pharmaceutically acceptable carrier.

In another embodiment, the present invention is a method of increasing the level of endogenous growth hormone in a subject comprising administering to the subject a pharmaceutically effective amount of a pharmaceutical composition according to any of the previous embodiments.

In another embodiment, the present invention is a method for treating a subject of a ghrelin receptor related disorder or condition, the method including administering to the subject a pharmaceutically effective amount of the pharmaceutical composition of the present invention, wherein the disorder or condition is selected from increase appetite, attenuate cachexia in patient with cancer or chronic obstructive pulmonary disease, suppressing ghrelin's orexigenic effects, treating obesity, regulating food intake, GI motility, gastric emptying, body weight, and treating ulcer or gastroparesis, treating anorexia nervosa, heart failure, diabetes mellitus (including Type 1 and 2) or diabetes mellitus complications, constipation and Parkinson's disease.

In another embodiment, the present invention is an isolated peptidimimetc, wherein said isolated peptidomimetic is selected from the group consisting of peptidomimetics included in Tables 1 and 2 which include a fluoride group.

In another embodiment, the present invention is an isolated peptidomimetic, wherein said isolated peptidomimetic comprises the amino acid sequence H-Inp-D-2-Nal-D-2-Nal-1-Nal-Lys(4-FB)-NH2.

In another embodiment, the present invention is an isolated peptidomimetic, wherein said isolated peptidomimetic comprises the amino acid sequence H-Inp-D-2-Nal-D-2-Nal-Phe-Lys(2-FP)-NH2.

In another embodiment, the present invention is an isolated peptidomimetic, wherein said isolated peptidomimetic comprises the amino acid sequence H-Inp-D-2-Nal-D-2-Nal-Tyr-Lys(2-FP)-NH2.

In another embodiment, the present invention provides for a method of delivering an agent to a population of cancer cell or cardiac cells. The method, in one embodiment, includes: a) providing a conjugate of any of the previous embodiments carrying the agent; and b) exposing the conjugate to the population of cells suspected of containing cancer cells or cardiac cells.

In another embodiment, the present invention is a compound having the amino acid sequence H-Inp-D-2-Nal-D-2-Nal-Xaa-Aaa(fluorine containing side-chain)-NH2, wherein Aaa is an amino acid having a side chain that readily allows the incorporation of a fluorine group.

In one embodiment of the previous embodiment, Xaa is 0, 1, or 2 variable amino acid residues.

In one embodiment of the previous embodiment, Xaa is 1 or 2 variable amino acid residues.

In one embodiment of the compound of the previous three embodiments the variable amino acid Xaa is selected from the group consisting of 1-Nal, Tyr, Phe and Ser.

In one embodiment of the compound of the previous four embodiments, the Aaa is Lys.

In another embodiment, the present invention provides compound comprising a formula selected from the group of formulae consisting of the formulae included in FIGS. 46A, 46B, 49A, 49B, 50A and 50B.

BRIEF DESCRIPTION OF THE DRAWINGS

The following figures illustrate various aspects and preferred and alternative embodiments of the invention.

DESCRIPTION OF THE INVENTION

Definitions and Abbreviations

Figure 1A:
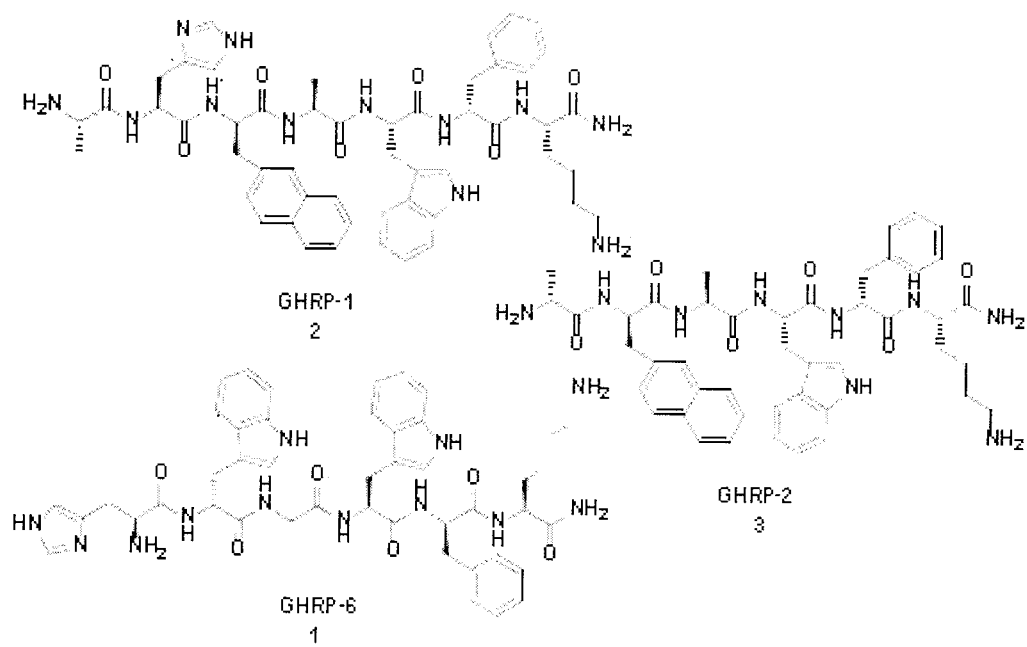
FIG. 1 (A) Chemical structure of prior art peptides of the original class of GHRPs. (B) Truncated ghrelin derivatives.
Figure 1B:
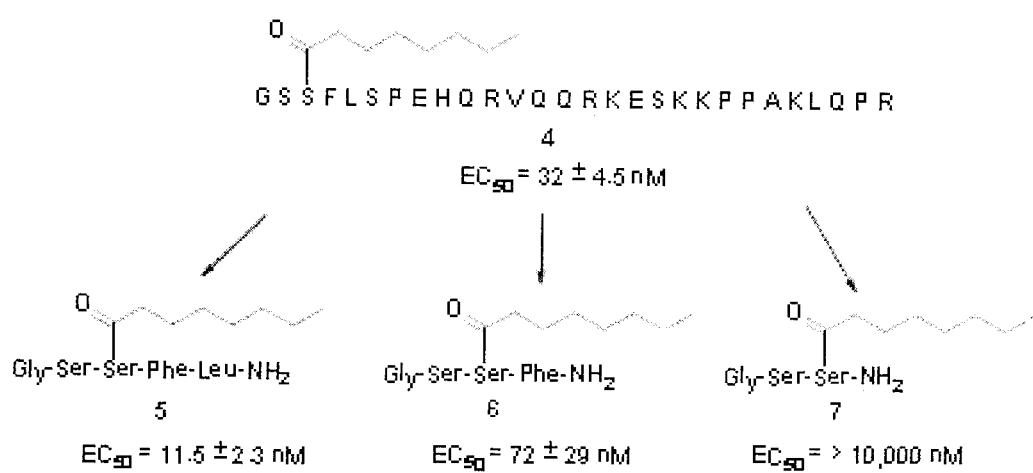
Figure 2A:
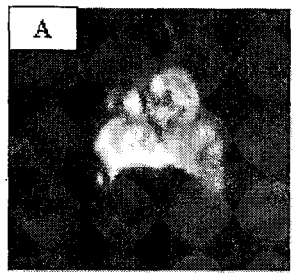
FIG. 2 A) DW-MRI in a 67-year-old male with PCa in the left mid-gland. Arrows show a restricted diffusion in the left peripheral zone of the prostate, (adapted from Seitz, M. et al., 2009), [38] B) 18F-fluorodeoxyglucose (FDG) PET/CT image of a 67-year-old man with PCa, with intense hypermetabolism in the right prostatic lobe apparent (adapted from Jadvar, H., 2011). [45]
Figure 2B:
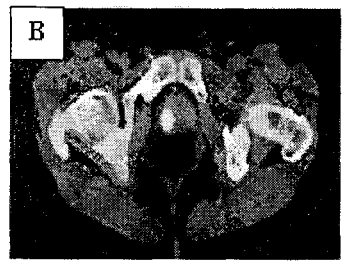

Unless defined otherwise, all technical and scientific terms used herein have the same meaning as commonly understood by one of ordinary skill in the art to which this invention belongs. Also, unless indicated otherwise, except within the claims, the use of "or" includes "and" and vice versa. Non-limiting terms are not to be construed as limiting unless expressly stated or the context clearly indicates otherwise (for example "including", "having" and "comprising" typically indicate "including without limitation"). Singular forms including in the claims such as "a", "an" and "the" include the plural reference unless expressly stated otherwise. In order to aid in the understanding and preparation of the within invention, the following illustrative, non-limiting, examples are provided. All publications cited are incorporated herein by reference.

The following standard one letter and three letter abbreviations for the amino acid residues in L forms which may be used throughout the specification: A, Ala—alanine; R, Arg—Arginine; N, Asn—Asparagine; D, Asp—Aspartic acid; C, Cys—Cysteine; Q, Gln—Glutamine; E, Glu—Glutamic acid; G, Gly—Glycine; H, His—Histidine; I, Ile—Isoleucine; L, Leu—Leucine; K, Lys—Lysine; M, Met—Methionine; F, Phe—Phenylalanine; P, Pro—Proline; S, Ser—Serine; T, Thr—Threonine; W, Trp—Tryptophan; Y, Tyr—Tyrosine; and V, Val—Valine.

D-Phe: D-Phenylalanine
D-2-Nal: D-2-Naphthylalanine
D-Ala: D-Alanine
Inp: Isonipecotic acid, i.e.:

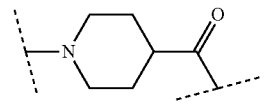

Aib: Aminoisobutyric acid.
1-Nal: 1-naphthylalanine.
4-FB: 4-fluorobenzoyl
2-FP: 2-fluoropropionyl
AEEA: Aminoethylethanolamine
$EC_{50}$: half-maximal effective concentration
$IC_{50}$: half-maximal inhibitory concentration

[18F]SFB: N-Succinimidyl-4-[18F]fluorobenzoate
[18F]NFP: 4-nitrophenyl 2-[18F]fluoropropionate
"hot": the radioactive form of the compound
"cold": the non-radioactive form of the compound
"GHRPs": growth hormone releasing peptides
"GH": growth hormone
"GHS": growth hormone secretagogues The term "amino acid residue" is known in the art. In general the abbreviations used herein for designating the amino acids and the protective groups are based on recommendations of the IUPAC-IUB Commission on Biochemical Nomenclature (see Biochemistry (1972) 11:1726-1732). In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan. In certain embodiment, the amino acids used in the application of this invention include analogs, derivatives and congeners of any specific amino acid referred to herein, as well as C-terminal or N-terminal protected amino acid derivatives (e.g. modified with an N-terminal or C-terminal protecting group) as well as unnatural amino acids.

The term "unnatural" refers in this document to amino acids not naturally encoded or found in the genetic code of any organisms.

In this document the term "non-coded" amino acid or residue, refers to a natural amino acid that substitutes another natural amino acid in the wild type amino acid sequence of a peptide, including a natural amino acid that substitutes a natural amino acid in the peptide.

"Subject" or "patient" refers to a subject in need of treatment for a condition, disorder or disease, or in need of a diagnosis for a condition, disorder or disease.

Generic groups that allow both derivatisation with fluorine as well as convenient introduction of radiofluorine may be used. These groups are referred to as prosthetic groups.

Peptidomimetics are synthetic or artificial compounds based on, or derived from, peptides and proteins. Such peptidomimetics may have such attributes as having increased specificity and/or affinity for a receptor. Peptidomimetics of the present invention may be obtained by inserting an amino acid residue into a native or non-native GHS.

The peptides and peptidomimetics of the invention, can have a variety of lengths. A peptide or peptidomimetic of the invention can have, for example, a relatively short length of at least 4 residues, including 4, 5, 6, 7, 8, 9, 10, 11, 12, 13, 14, 15, 16, 17, 18, 19, 20 and so forth residues. A peptide or peptidomimetic of the invention also can be useful in the context of a significantly longer sequences.

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α-dialkylglycine or α-aminocycloalkane carboxylic acid; an Nα-Cα cyclized amino acid; an Nα-methylated amino acid; a β- or γ-amino cycloalkane carboxylic acid; an α,β-unsaturated amino acid; a β,β-dimethyl or β-methyl amino acid; a β-substituted-2,3-methano amino acid; an N-Cδ or Cα-Cδ cyclized amino acid; a substituted proline or another amino acid mimetic; a cyclized amino acid such as Inp. A peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

In one embodiment of the present invention, the peptides and peptidomimetics of the invention may be provided in isolated form. As used herein in reference to a peptide or peptidomimetic of the invention, the term "isolated" means a peptide or peptidomimetic that is in a form that is relatively free from material such as contaminating polypeptides, lipids, nucleic acids and other cellular material that normally is associated with the peptide or peptidomimetic in a cell or that is associated with the peptide or peptidomimetic in a library or in a crude preparation.

The compounds of the present invention may include a fluoro-containing prosthetic group, whereby the radioisotope fluorine-18 (F-18 or F18) is a part of the prosthetic group molecule allowing for attachment to the peptidomimetic. Non-limiting examples of prosthetic groups that may be used with the present invention may include 4-FB and 2-FP. Other prosthetic groups that readily allow for the incorporation of F-18 include click chemistry approaches to create a fluorinated triazole species, for example, through azide alkyne Huisgen cycloaddition or inverse electron demand Diels-Alder reaction. Alternatively, the addition of F-18 can be accomplished through the direct labelling of the peptide side-chain, through aliphatic or aromatic nucleophilic substitution.

Presented herein are imaging tools that may be used to investigate changes in the peptide hormone ghrelin and its receptor, GHS-R, in cancer cells and in cardiomyocytes as a possible marker of disease severity.

The present invention also provides a method of imaging a target site in a subject. The target site may be a tumor, preferably prostate cancer, and may be used to distinguish between malignant and benign tumors by targeting the ghrelin receptor, which is known to have a differential expression in benign and malignant tumors.

In one embodiment, a method of assessing or diagnosing the malignancy of a tumor may include: (a) contacting the tumor with a conjugate as defined in claims 1-6, (b) detecting the expression of the conjugate in the tumor, (c) comparing the expression of step (b) with the expression of said conjugate in a control tissue, and (d) assessing the malignancy of the tumor based on the comparison.

In another embodiment, a method of assessing or diagnosing the malignancy of a tumor may include administering to a subject a conjugate which contains a detectable label such as a fluoro-containing prosthetic group linked to a peptidomimetic of the present invention, and detecting the conjugate, thereby imaging the tumor in the subject. The image may then be compared to images of normal prostate tissue, or to images of benign prostate cancer, or to images of malignant prostate cancer. A diagnosis of the subject's image may then be made based on one or more of these comparisons. The present invention may also be used to diagnose heart disease, cardiac dysfunction. Examples of radionuclides useful as detectable labels include, but are not limited to, 4-FB, 2-FP and other prosthetic groups that allow for the incorporation of F-18.

Positron emission tomography (PET), including fluorine-18 PET, PET-computed tomography (CT) hybrid and PET-magnetic resonance imaging (MRI) hybrid imaging with the compounds of the present invention may enable oncologists to diagnose and stage cancer, and to enable cardiologists to predict LV dysfunction before it occurs through detection of early derangements in GHS-R, and to gauge the response to therapy.

In a further embodiment, the present invention provides a pharmaceutical composition comprising a conjugate of the present invention and a pharmaceutically acceptable carrier.

Such pharmaceutical compositions may be used for diagnostic purposes, preferably, for visualization of organs and tissues having a ghrelin receptor, preferably, for diagnosis of tumors, including distinguishing between benign and malignant tumors. Any suitable solid tumor may be encompassed by the invention, both primary tumors and metastasis, of tumors selected from, but not limited to, from melanoma, colon, breast, lung, prostate, brain or head and neck cancer. Preferably for diagnosis of prostate cancer, including distinguishing between benign and malignant prostate cancer. Such pharmaceutical compositions may also be used for diagnosis of heart disease or growth hormone (GH) deficiency.

The pharmaceutical compositions of the present invention may be used for administration to subjects in a biologically compatible form suitable for administration in vivo. By "biologically compatible form suitable for administration in vivo" is meant a form of the substance to be administered in which any toxic effects are outweighed by the therapeutic effects. Administration of a therapeutically active amount of the pharmaceutical compositions of the present invention, or an "effective amount", is defined as an amount effective at dosages and for periods of time, necessary to achieve the desired result. A therapeutically effective amount of a substance may vary according to factors such as the disease state/health, age, sex, and weight of the recipient, and the inherent ability of the particular peptidomimetic to elicit a desired response. Dosage regimen may be adjusted to provide the optimum therapeutic response. For example, several divided doses may be administered daily or on at periodic intervals, and/or the dose may be proportionally reduced as indicated by the exigencies of the therapeutic situation. The amount of peptidomimetic for administration will depend on the nature of the peptidomimetic, the route of administration, time of administration and varied in accordance with individual subject responses. Suitable administration routes may be intramuscular injections, subcutaneous injections, intravenous injections or intraperitoneal injections, oral and intranasal administration. In a preferred embodiment, the administration route may be intravenous injection.

The pharmaceutical compositions may be provided in a kit that includes instructions or labels as to the use of the conjugate (i.e. imaging, diagnosis, etc. of ghrelin-receptors containing sites, such as tumors or cardiac tissue).

Such pharmaceutical compositions may be used to treat GH deficiency, stimulate GH secretion from the pituitary or increase appetite, attenuate cachexia in patient with cancer or chronic obstructive pulmonary disease. Such pharmaceutical compositions may also be used for suppressing ghrelin's orexigenic effects, treating obesity, regulating food intake, GI motility, gastric emptying or body weight, and treating ulcer or gastroparesis.

Such pharmaceutical compositions may also be used to treat a variety of disorders such as anorexia nervosa, heart failure, diabetes mellitus (including Type 1 and 2) or diabetes mellitus complications, constipation and Parkinson's disease. Such pharmaceutical compositions may also be used as a therapeutic agent to treat cancer (Vodnik M et al. Horm Metab Res 2016; 48: 1-15; Dimitrios Nikolopoulos et al., Regulatory Peptides 163 (2010) 7-17).

The peptidomimetics of the present invention have been found to have high affinity for GHS-R1a receptors as demonstrated by receptor-ligand binding assays described in Example 1, with $IC_{50}$ nanomolar values in the single digits and even sub-nM values. As such, the peptidomimetics of the present invention listed in Table 1 (excluding GHRP-6, GHRP-1, GHRP-2 and G-7039) and Table 2, particularly TL-MF-4-2FP, TL-MF-3-2FP, 2-FP-G-7039 and MMF-01-113-G are GHS-R1a ligands.

Figure 51:
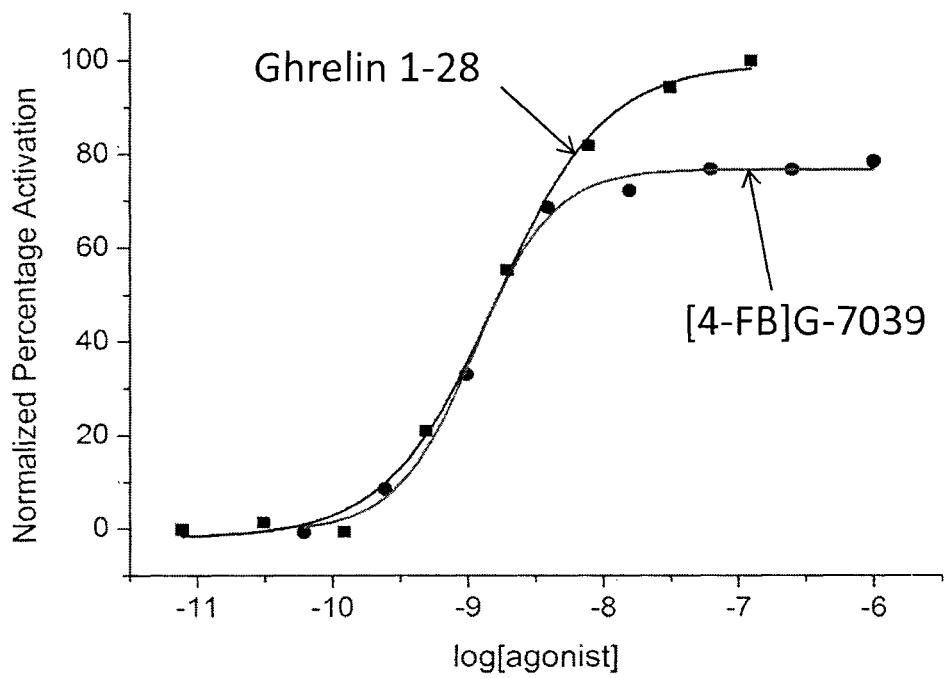
FIG. 51 Efficacy curves for agonist 1-Nal$^4$, Lys$^5$(4-FB)] G-7039 (referred to in Table 1 as compound MMF-01-115-H, LCE No. 270) and the control ligand ghrelin.
Figure 52:
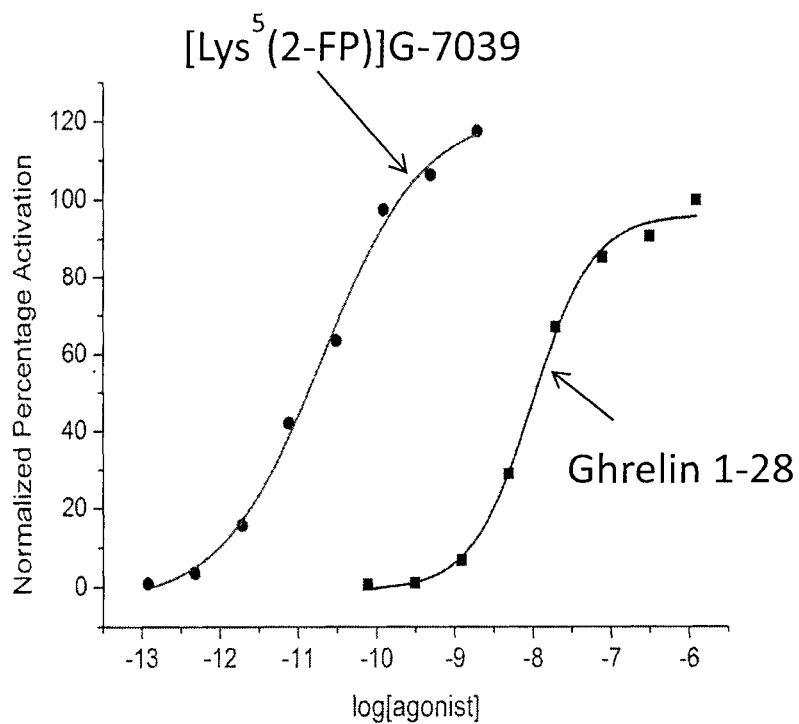
FIG. 52 Efficacy curves for agonist [Lys$^5$(2-FP)]G-7039 (referred to in Table 1 as compound 2-FP-G-7039; LCE No. 295) and the control ligand ghrelin.

As seen in Example 3 and illustrated in FIGS. 51 and 52, peptidomimetics of the present invention were also found to have low $EC_{50}$ values and may serve as GHS-R1a agonists. As such, peptidomimetics of the present invention may be used for indications such as suppressing ghrelin's orexigenic effects, treating obesity, regulating food intake, GI motility, gastric emptying or body weight, and treating ulcer or gastroparesis, to treat a variety of disorders such as anorexia nervosa, heart failure, diabetes mellitus (including Type 1 and 2) or diabetes mellitus complications, constipation and Parkinson's disease.

Examples of peptidomimetics that may be used as agonists include MMF-01-115-H and 2-FP-G-7039 both having an $EC_{50}$ value below that of ghrelin (see FIGS. 51 and 52 respectively and Example 3).

As such, the present application includes methods of treating a disorder associated with GHS-R1a, including stimulation of growth hormone release, increase in appetite, gastric emptying, and cachexia, including cachexia in patients with cancer. The method may include administering to a person in need, an effective amount of a peptidomimetic of the present invention.

In order to aid in the understanding and preparation of the within invention, the following illustrative, non-limiting, examples are provided.

Example 1

Materials and Methods

All reagents were obtained from commercial suppliers and used without further purification. Reaction monitoring was carried out by TLC using 60F254 silica coated plastic plates (EMD Chemicals Inc.), with visualization under a UV lamp (254/365 nm). Melting points were recorded on a Mel-Temp® 1101D digital melting point apparatus. Peptides were either synthesized manually or through the use of a Biotage® Syro Wave™ automated peptide synthesizer. Peptide vessels were shaken using an IKA® Vibrax VXR basic shaker with centrifugation performed on a Beckman Coulter™ Allegra X-30R or Fisher GS-6R centrifuge. In order to aid peptide dissolution, sonication of solutions was accomplished via a Bransonic® 2510R-MTH or Fisher F5-14 ultrasonic cleaner. A Fisher 2052 Isotemp® machine was used to heat up test tubes in the Kaiser Test. Peptides were cryodessicated using a Labconco® FreeZone Freeze Dry System. UV traces were obtained with a Waters 2487 UV/Vis Dual λ Absorbance Detector (170-900 nm) and low-resolution mass spectra with a Micromass® Quattro Micro™ API mass spectrometer (ESI-LC-MS). Peptide purification was achieved through HPLC (MeCN+0.1% TFA, H$_2$O+0.1% TFA solvent system). All peptides and small molecules obtained had a purity ≥95% as determined by HPLC or UPLC. A reverse-phase (RP) semi-preparative C-18 column (SunFire™ OBD™, 19×150 mm or Agilent™ Zorbax® 21.2×150 mm) was used for preparative HPLC, whilst a C-18 RP column (SunFire™ 4.6×150 mm or Agilent™ Zorbax®, 4.6×150 mm) was used for analytical HPLC. Accurate mass spectrometry (HRMS) was carried out on a Finnigan™ MAT 8400 Mass Spectrometer (EI) for small molecules and on a Bruker Daltonics Reflex™ IV Mass Spectrometer (ESI) for peptides. $^1$H NMR and $^{13}$C NMR spectroscopy were performed on a Mercury VX 400 machine at 400 and 100 MHz respectively. Chemical shifts are referenced to residual solvent, reported in ppm on a δ scale and all coupling constants quoted in hertz (Hz).

General Procedures

Manual Fmoc Solid-Phase Peptide Synthesis (Fmoc-SPPS)

Rink amide MBHA resin (192 mg, 0.1 mmol, 1.0 eq., 0.52 mmol g-1 loading) was vortexed in DCM (2.0 ml, 1 min.), allowed to swell (15 mins) and solvent removed. This was followed by addition of DMF (2.0 ml), vortexing (1 min.) and removal of solvent. Deprotection of the Fmoc group was then performed. A solution of 20% piperidine/DMF (1.5 ml, v/v) was added to the resin and the subsequent mixture vortexed (2 mins) and solvent removed. This was then repeated a second time with vortexing for 15 minutes. After solvent had been removed, the resin was washed of any unreacted by-products with DMF six times (2.0 ml, vortex 30 s). The desired amino acid or small molecule (Fmoc-AA1, 0.3 mmol, 3.0 eq.) and coupling reagent (HCTU, 0.12 g, 0.3 mmol, 3.0 eq.) were then dissolved in DMF (1.5 ml) and added to the deprotected resin. After vortexing (30 s), DIPEA (111 μl, 0.6 mmol, 6.0 eq.) was added and the final mixture vortexed (1-2 hrs). The resin was then washed with DMF (2.0 ml, 30 s vortex) a final four times. The deprotection/coupling cycle was then repeated unless the final amino acid in the sequence had been added, in which case the peptide was washed with DCM five times (2.0 ml, 30 s vortex) and stored in a refrigerator. Removal of the N-terminal Fmoc-group was carried out in the same fashion as the deprotection cycle described previously, with resin washing occurring six times with DMF (2.0 ml, 30 s vortex) and four times with DCM (2.0 ml, 30 s vortex). Successful synthesis of the desired peptide was then ascertained via a microcleave prior to full cleavage of the peptide from the solid-support. This was carried out as follows: a solution of 95% TFA: 2.5% (iPr)3SiH: 2.5% H2O (300 μl) was added to a small number of resin beads (<5 mg) and the subsequent mixture vortexed (3 hrs). The clear liquid was then treated with N$_2$ until a small film formed. Analytical HPLC was then performed to determine whether the correct peptide had been synthesized. If the correct peptide had been obtained, a full cleavage was performed using a mixture of 95% TFA: 2.5% (iPr)3SiH: 2.5% H$_2$O (2.0 ml) for 5-6 hrs. The subsequent solution was cooled in an ice-bath alongside $^t$Bme (40 ml). After 10 minutes, $^t$Bme (20 ml) was added to the peptide solution, leading to the formation of a white precipitate. The precipitate was cooled further (10 mins) and then centrifuged (7 mins). Decanting of the supernatant was followed by addition of a second aliquot of tBMe (20 ml), vortexing (30 s) and final centrifugation (7 mins). This delivered a white solid which was then freeze-dried (20 mins) to furnish crude peptide. Preparative HPLC was then used to purify the product peptide.

Deprotection of the Alloc Protecting Group

The resin-bound peptide was vortexed in DCM (4.5 ml, 30 s) and allowed to swell (10 mins). Deprotection was carried out under a blanket of N$_2$. The swollen resin-bound peptide was stirred (5 mins) before addition of PhSiH$_3$ (296 μl, 2.4 mmol, 24.0 eq.). Further stirring (5 mins) ensued prior to treating with Pd(PPh$_3$)$_4$ (120 mg, 0.01 mmol, 0.1 eq.). The reaction mixture changed colour from yellow to orange to brown to dark brown. After 5 minutes, the solution was vortexed (5 mins), solvent removed and the brown-coloured resin washed four times with DCM (2.0 ml, 30 s vortex). The procedure was then repeated ab initio, with final resin washing occurring in the following order: DCM, DMF, MeOH, DMF and DCM (all 2.0 ml, 30 s vortex).

Kaiser Test

The Kaiser test was used as a qualitative test to determine the success of amino acid coupling. A small number of resin beads (<5 mg) were taken and treated with Phenol: EtOH (200 μl, 8:2 v/v), 0.001 M KCN(aq.): Pyridine (200 μl, 2:98 v/v, 0.001 M aqueous KCN) and Ninhydrin in EtOH (200 μl, 5% w/v) respectively. Tentagel resin (<5 mg) was used as a control in this test. Both test tubes were heated to 70° C. The presence of free amine was indicated by blue resin beads whilst yellow resin beads showed protected amine groups to be present.

Receptor-Ligand Binding Assay

Competitive binding assays were run at the Lawson Health Research Institute at St. Joseph's Health Care in London. These were carried out in triplicate using HEK293/GHS-R1a cells (prepared by our collaborator Becky McGirr) with [$^{125}$I]ghrelin as a competitive radioligand. To begin with, a fresh solution of binding buffer (50 ml) was made up by adding HEPES (0.3 g, 25 mM), MgCl$_2$ (0.051 g, 5 mM), CaCl$_2$ (7.4×10$^{-3}$ g, 1 mM), EDTA (0.015 g, 2.5 mM) and BSA (0.2 g, 0.4%) to distilled H2O. The resultant solution was mixed over gentle heat. The pH was then adjusted to 7.4 and the solution filtered. Two miniature complete protease inhibitor tablets were then added and the final buffer solution kept on ice.

After the buffer had been made, assay tubes were labelled and kept on ice during the setup. To assay tubes 1-21, 25-27 and 28-30 was added binding buffer (200 μl, 230 μl and 300 μl respectively). No buffer was added to tubes 22-24. An aliquot of frozen cells was thawed to room temperature, centrifuged (3000×g, 10 mins, room temperature) and the subsequent cell pellet re-suspended in binding buffer (2 ml) and placed on ice. Cells (50 μl) were then added to assay tubes 1-21 and 25-27. Cold peptide was then prepared. This was carried out by adding stock peptide (20 μl) to binding buffer (180 μl) to make a peptide solution of 10$^{-4}$M concentration. Binding buffer (180 μl) was then added to assay tubes labelled 10$^{-5}$ to 10$^{-11}$. A series of dilutions was then made in order to acquire 10$^{-5}$ to 10$^{-11}$M concentrations. Cold peptide (30 μl) was then added to the corresponding assay tubes in triplicate.

[$^{125}$I]-ghrelin was then prepared by adding 10 μl to binding buffer (3 ml) and vortexing the resultant solution. A second solution of [$^{125}$I]-ghrelin (20 μl) was added to an empty assay tube and counted on the gamma counter (using protocol 3). The volume of [$^{125}$I]-ghrelin or binding buffer was adjusted as needed in order to get 15 000 cpm for every 20 μl aliquot. [$^{125}$I]-ghrelin (20 μl) was then pipetted into assay tubes 1-27. All assay tubes were then vortexed, capped and immediately agitated (550 rpm, 20 mins, 37° C.). After 20 minutes, tubes 1-21 and 25-27 were spun in a large centrifuge (2800 rpm, 2 mins, 4° C.). The solution in all of the tubes was then transferred to Eppendorf tubes (0.5 ml), further binding buffer added (200 µl), the solutions mixed by pipetting and transferred to 0.5 ml tubes. The tubes were then spun again (13 000×g, 5 mins, 4° C.) and placed on ice. The supernatant was removed and the cell pellet rinsed with ice-cold Tris-HCl (200 µl, 50 mM, pH 7.4) and the tubes mixed by inversion. Tubes were spun a final time (13,000×g, 5 mins, 4° C.), cooled on ice and supernatant removed. The tubes were then placed in 12×75 mm assay tubes and counted using a gamma counter (see protocol 3). The binding assay may be summarized as follows:

1) Tubes 1-21: 200 µl binding buffer, 50 µl cells, 30 µl cold peptide, 20 µl [$^{125}$I]-ghrelin.
2) Tubes 22-24: 20 µl [$^{125}$I]-ghrelin.
3) Tubes 25-27: 20 µl [$^{125}$I]-ghrelin, 50 µl cells, 230 µl binding buffer.
4) Tubes 28-30: 300 µl binding buffer.

Synthesis of Peptidomimetics

All peptides were synthesized by the same general procedure as described herein above unless otherwise noted.

LCE00210: H-Aib-His-D-2-Nal-D-Phe-Lys-NH$_2$ (Ipamorelin)

The product was purified by preparative HPLC (5-80% MeCN+0.1% TFA). This furnished a white powder (20.5 mg, 19%): $^1$H-NMR (400 MHz, CD3OD); D-2-Nal, D-Phe, His: δ 7.99 (s, 1H, ArH), 7.80-7.76 (m, 1H, ArH), 7.71 (d, J=8.6 Hz, 2H, ArH), 7.56 (s, 1H, ArH), 7.44-7.37 (m, 2H, ArH), 7.32-7.17 (m, 6H, ArH), 6.92 (s, 1H, His Hδ), 4.58 (m, 3H, Hα), 3.30-3.21 (m, 1H, D-2-Nal Hβ), 3.15-3.00 (m, 2H, Hβ), 2.96-2.72 (m, 3H, Hβ), Lys: 4.11 (dd, J=9.7, 4.2 Hz, 1H, Hα), 2.96-2.72 (m, 2H, Hε), 1.75-1.64 (m, 1H, Hβ), 1.54-1.40 (m, 3H, Hβ, 2Hδ), 1.05-0.93 (m, 2H, Hγ), Aib: 1.48 (s, 3H, CH3) 1.44 (s, 3H, CH3) ppm. ESI-LC-MS m/z 356.9 [M+2H]2+; HRMS (ESI-MS) calcd. for C38H50N9O5 [M+H]+ 712.3935, found 712.3959.

5.3.2 LCE00211: H-Aib-His-D-2-Nal-D-Phe-Lys(4-FB)-NH$_2$ (4-FB-Ipamorelin)

Purification by preparative HPLC (20-70% MeCN+0.1% TFA) yielded a white powder (15.4 mg, 15%): $^1$H-NMR (400 MHz, CD3OD); D-2-Nal, D-Phe, His, 4-FB: δ 7.91 (s, 1H, ArH), 7.85-7.77 (m, 3H, ArH, 2F-ArH), 7.70 (d, J=7.9 Hz, 2H, ArH), 7.54 (s, 1H, ArH), 7.45-7.40 (m, 2H, ArH), 7.29-7.19 (m, 6H, ArH), 7.14-7.07 (m, 2H, 2F-ArH), 6.93 (s, 1H, His Hδ), 4.65-4.52 (m, 3H, Hα), 3.30-3.27 (m, 1H, Hβ), 3.23 (d, J=4.0, 1H, Hβ), 3.10 (dd, J=13.5, 7.8 Hz, 1H, Hβ), 3.04-2.74 (m, 3H, Hβ), Lys: 4.12 (dd, J=9.8, 4.2 Hz, 1H, Hα), 3.04-2.74 (m, 2H, Hε), 1.77-1.67 (m, 1H, Hβ), 1.58-1.42 (m, 3H, Hβ, 2Hδ), 1.14-1.03 (m, 2H, Hγ), Aib: 1.50 (s, 3H, CH3), 1.46 (s, 3H, CH3) ppm. ESI-LC-MS m/z 418.0 [M+2H]2+; HRMS (ESI-MS) calcd. for C45H53FN9O6 [M+H]+ 834.4103, found 834.4133.

5.3.3 H-Aib-His-D-2-Nal-D-Phe-Lys(4-FB-AEEA)-NH$_2$ (4-FB-AEEA-Ipamorelin)

Peptide purification by preparative HPLC (20-60% MeCN+0.1% TFA) delivered an off-white powder (9.2 mg, 8%): $^1$H-NMR (400 MHz, CD3OD); His, D-2-Nal, D-Phe, 4-FB: δ 7.93 (s, 1H, ArH), 7.86-7.77 (m, 3H, ArH, 2F-ArH), 7.71 (d, J=8.0 Hz, 2H, ArH), 7.55 (s, 1H, ArH), 7.46-7.41 (m, 2H, ArH), 7.31-7.18 (m, 6H, ArH), 7.17-7.10 (m, 2H, F-ArH), 6.94 (s, 1H, His Hδ), 4.65-4.58 (m, 2H, Hα), 4.55 (t, J=7.5 Hz, 1H, Hα), 3.16-2.76 (m, 6H, Hβ), Lys: 4.10 (dd, J=9.7, 4.2 Hz, 1H, Hα), 3.16-2.76 (m, 2H, Hε), 1.72-1.62 (m, 1H, Hβ), 1.52-1.43 (m, 1H, Hβ), 1.41-1.30 (m, 2H, Hδ), 1.07-0.97 (m, 2H, Hγ), AEEA linker: 3.93 (s, 2H, NHCOCH2O), 3.65-3.61 (m, 6H, CH2), 3.53 (t, J=5.6 Hz, 2H, CH2), Aib: 1.50 (s, 3H, CH3), 1.47 (s, 3H, CH3) ppm. ESI-LC-MS m/z 490.4 [M+2H] 2+; HRMS (ESI-MS) calcd. for C51H64FN10O9 [M+H]+, found.

5.3.4 H-His-D-Trp-Ala-Trp-D-Phe-Lys-NH$_2$ (GHRP-6)

Purification by preparative HPLC (15-80% MeCN+0.1% TFA) gave a white powder (19.7 mg, 14%): $^1$H-NMR (400 MHz, CD3OD); His, D-Trp, Trp, D-Phe: δ 8.46 (s, 1H, His Hε), 7.54 (d, J=7.8 Hz, 1H, ArH), 7.46 (d, J=7.8 Hz, 1H, ArH), 7.28 (t, J=7.7 Hz, 2H, ArH), 7.23-7.13 (m, 4H, ArH), 7.12-6.92 (m, 8H, 7ArH, His Hδ), 4.47 (t, J=7.4 Hz, 2H, Trp Hα), 4.35 (t, J=6.7 Hz, 1H, Hα), 4.28 (t, J=7.9 Hz, 1H, Hα), 3.22-3.14 (m, 3H, Hβ), 3.14-3.02 (m, 3H, Hβ), 2.83 (d, J=8.6 Hz, 2H, Hβ), Lys: 4.03 (dd, J=10.3, 3.9 Hz, 1H, Hα), 2.75 (t, J=6.8 Hz, 2H, Hε), 1.76-1.63 (m, 1H, Hβ), 1.51-1.39 (m, 3H, Hβ, 2Hδ), 0.97-0.88 (m, 2H, Hγ), Ala: 3.91 (q, J=7.2 Hz, 1H, Hα), 0.86 (d, J=7.3 Hz, 3H CH3) ppm. ESI-LC-MS m/z 437.4 [M+2H]2+; HRMS (ESI-MS) calcd. for C46H57N12O6 [M+H]+ 873.4524 found 873.4531.

5.3.5 H-Ala-His-D-2-Nal-Ala-Trp-D-Phe-Lys-NH$_2$ (GHRP-1)

The product was purified by preparative HPLC (15-80% MeCN+0.1% TFA). This yielded a white powder (26.4 mg, 19%): $^1$H-NMR (400 MHz, CD3OD); His, D-2-Nal, Trp, D-Phe: δ 8.41 (s, 1H, His Hε), 7.81-7.71 (m, 3H, ArH), 7.65 (s, 1H, ArH), 7.49 (d, J=7.8 Hz, 1H, ArH), 7.46-7.40 (m, 2H, ArH), 7.35 (dd, J=8.4, 1.7 Hz, 1H, ArH), 7.31 (d, J=8.1 Hz, 1H, ArH), 7.24-7.13 (m, 3H, ArH), 7.10-7.04 (m, 4H, ArH), 7.00 (t, J=7.5 Hz, 1H, ArH), 6.89 (d, J=0.8 Hz, 1H, His Hδ), 4.67-4.60 (m, 2H, Hα), 4.38 (t, J=7.4 Hz, 1H, Hα), 4.32 (t, J=7.7 Hz, 1H, Hα), 3.25-2.68 (m, 8H, Hβ), Ala, Ala: 4.17-4.10 (m, 1H, Hα), 3.94 (q, J=7.0 Hz, 1H, Hα), 1.35 (d, J=7.1 Hz, 3H, CH3), 1.10-1.01 (m, 3H, CH3), Lys: 4.17-4.10 (m, 1H, Hα), 3.25-2.68 (m, 2H, Hε), 1.81-1.70 (m, 1H, Hβ), 1.58-1.45 (3H, Hβ, 2Hδ), 1.10-1.01 (m, 2H, Hγ), ppm. ESI-LC-MS m/z 478.5 [M+2H]2+; HRMS (ESI-MS) calcd. for C51H63N12O7 [M+H]+ 955.4943 found 955.4964.

5.3.6 H-Inp-D-2-Nal-D-2-Nal-Phe-Lys(4-FB)-NH$_2$ (4-FB-G-7039)

Preparative HPLC (35-80% MeCN+0.1% TFA) furnished the title compound as a white solid (5.90 mg, 6%): 1H-NMR (400 MHz, (CD3)2SO); δ 8.50 (d, J=8.2 Hz, 1H, NH), 8.45 (t, J=5.5 Hz, 1H, NH), 8.39 (s, 1H, NH), 8.15-8.09 (m, 2H, NH), 8.04 (d, J=8.4 Hz, 1H, NH), 7.86-7.82 (m, 2H, F-ArH), 7.82-7.76 (m, 2H, ArH), 7.75-7.66 (m, 4H, ArH), 7.58 (s, 1H, ArH), 7.48 (s, 1H, ArH), 7.45-7.38 (m, 4H, ArH), 7.31 (dd, J=8.5, 1.5 Hz, 1H, ArH), 7.28 (s, 1H, ArH), 7.26 (s, 1H, NH), 7.24-7.17 (m, 5H, ArH), 7.15-7.08 (m, 2H, ArH), 7.04 (s, 1H, NH), 4.66-4.60 (m, 1H, Hα), 4.60-4.53 (m, 2H, Hα), 4.20-4.14 (m, 1H, Lys-Hα), 3.25-3.14 (m, 2H, CH2), 3.13-3.02 (m, 3H, CH2), 2.98-2.91 (m, 1H, CH2), 2.90-2.83 (m, 1H, CH2), 2.81-2.56 (m, 5H, CH2), 2.30-2.22 (m, 1H, Inp-Hα), 1.75-1.65 (m, 1H, CH2), 1.62-1.55 (m, 1H, CH2), 1.54-1.43 (m, 6H, CH2), 1.38-1.19 (m, 2H, CH2), ppm. ESI-LC-MS m/z 452.5 [M+4H−F]2+; HRMS (ESI-MS) calcd. for C54H59FN7O6 [M+H]+ 920.4511 found 920.4529.

5.3.7 H-Inp-D-2-Nal-D-2-Nal-1-Nal-Lys-NH$_2$ (MMF-01-113-G)

Peptide purification by preparative HPLC (25-80% MeCN+0.1% TFA) delivered a white powder (24.9 mg, 23%): 1H-NMR (400 MHz, CD3OD); δ 8.12 (d, J=8.4 Hz, 1H, ArH), 7.84 (d, J=7.8 Hz, 1H, ArH), 7.78-7.72 (m, 2H, ArH), 7.68 (d, J=8.5 Hz, 3H, ArH), 7.62-7.46 (m, 5H, ArH), 7.43-7.35 (m, 5H, ArH), 7.30 (d, J=6.4 Hz, 1H, ArH), 7.27-7.21 (m, 2H, ArH), 7.02 (dd, J=8.4, 1.5 Hz, 1H, ArH), 4.69 (dd, J=9.4, 5.4 Hz, 1H, Hα), 4.65-4.55 (m, 2H, Hα), 4.32 (dd, J=9.4, 4.8 Hz, 1H, Lys-Hα), 3.65 (dd, J=14.4, 5.4 Hz, 1H, CH2), 3.20-3.10 (m, 2H, CH2), 3.05-2.94 (m, 3H, CH2), 2.92-2.80 (m, 5H, CH2), 2.76-2.62 (m, 2H, CH2), 2.30-2.23 (m, 1H, Inp-Hα), 1.92-1.81 (m, 1H, CH2), 1.75-

1.29 (m, 9H, CH2), ppm. ESI-LC-MS m/z 424.8 [M+2H]2+; HRMS (ESI-MS) calcd. for C51H58N7O5 [M+H]+ 848.4499, found 848.4501.

5.3.8 H-Inp-D-2-Nal-D-2-Nal-Phe-Lys-NH$_2$ (G-7039)

Purification of the peptide proceeded through preparative HPLC (25-80% MeCN+0.1% TFA). The title compound was obtained as a white powder (6.70 mg, 7%): $^1$H-NMR (400 MHz, CD3OD); 7.80-7.76 (m, 1H, ArH), 7.74 (dd, J=6.1, 2.2 Hz, 2H, ArH), 7.70 (dd, J=8.5, 3.5 Hz, 3H, ArH), 7.56 (s, 1H, ArH), 7.50 (s, 1H, ArH), 7.46-7.35 (m, 4H, ArH), 7.26 (dd, J=8.5, 1.5 Hz, 1H, ArH), 7.20-7.10 (m, 6H, ArH), 4.66-4.56 (m, 2H, Hα), 4.50 (dd, J=9.3, 5.4 Hz, 1H, Hα), 4.30 (dd, J=9.5, 4.7 Hz, 1H, Lys-Hα), 3.20-2.80 (m, 10H, CH2), 2.78-2.64 (m, 2H, CH2), 2.33-2.24 (m, 1H, Inp-Hα), 1.92-1.82 (m, 1H, CH2), 1.74-1.65 (m, 1H, CH2), 1.64-1.44 (m, 5H, CH2), 1.44-1.24 (m, 3H, CH2), ppm. ESI-LC-MS m/z 399.8 [M+2H] 2+; HRMS (ESI-MS) calcd. for C47H56N7O5 [M+H]+ 798.4343 found 798.4339.

5.3.9 H-Inp-His-D-2-Nal-D-2-Thi-Lys(4-FB)-NH$_2$ (Inp-Thi-4-FB-Ipamorelin)

The title peptide was prepared by automated peptide synthesis and purified by preparative HPLC (20-80% MeCN+0.1% TFA). This furnished a white powder (14.0 mg, 13%): $^1$H-NMR (400 MHz, CD3OD); His, D-2-Nal, D-2-Thi, 4-FB: δ 8.23 (s, 1H, His Hε), 7.86-7.81 (m, 2H, F-ArH), 7.80-7.77 (m, 1H, ArH), 7.73 (dd, J=8.8, 3.3 Hz, 2H, ArH), 7.59 (s, 1H, ArH), 7.45-7.39 (m, 2H, ArH), 7.27 (dd, J=8.5, 1.6 Hz, 1H, ArH), 7.22 (dd, J=5.0, 1.2 Hz, 1H, Thi-ArH), 7.15-7.08 (m, 2H, F-ArH), 6.92 (s, 1H, His Hδ), 6.91-6.85 (m, 2H, Thi-ArH), 4.61 (dd, J=10.3, 4.4 Hz, 1H, Hα), 4.53-4.47 (m, 2H, Hα), 4.22 (dd, J=9.8, 4.2 Hz, 1H, Lys-Hα), 3.39-3.29 (m, 6H, CH2), 3.26-3.22 (m, 1H, CH2), 3.01-2.80 (m, 5H, CH2), 2.53-2.44 (m, 1H, Inp-Hα), 1.87-1.50 (m, 8H, CH2), 1.35-1.22 (m, 2H, CH2), ppm. ESI-LC-MS m/z 433.8 [M+2H]2+; HRMS (ESI-MS) calcd. for C45H53FN9O6S [M+H]+ 866.3824 found 866.3850.

5.3.10 H-Aib-His-D-2-Nal-D-2-Thi-Lys(4-FB)-NH$_2$ (Thi-4-FB-Ipamorelin)

The title peptide was synthesized by automated peptide synthesis and purified by preparative HPLC (20-80% MeCN+0.1% TFA). This furnished a white solid (4.20 mg, 4%): 1H-NMR (400 MHz, (CD3)2SO); δ 8.83 (s, 1H, ArH), 8.59 (d, J=8.1 Hz, 1H, NH), 8.42 (t, J=5.6 Hz, 1H, NH), 8.29 (d, J=9.3 Hz, 1H, NH), 8.20 (d, J=8.2 Hz, 1H, NH), 8.09 (d, J=8.9 Hz, 1H, NH), 7.99 (s, 2H, NH), 7.86-7.81 (m, 2H, F-ArH), 7.79-7.75 (m, 1H, ArH), 7.72 (dd, J=8.7, 3.7 Hz, 2H, ArH), 7.65 (s, 1H, ArH), 7.41-7.37 (m, 2H, ArH), 7.35-7.31 (m, 2H, ArH, NH), 7.26 (dd, J=4.8, 1.5 Hz, 1H, Thi-H), 7.22-7.16 (m, 2H, F-ArH), 7.05 (s, 2H, NH, ArH), 6.88-6.84 (m, 2H, Thi-H), 4.73-4.66 (m, 1H, Hα), 4.62-4.51 (m, 2H, Hα), 4.19-4.12 (m, 1H, Lys-Hα), 3.21-3.12 (m, 4H, 2Hε, 2Hβ), 3.06-2.96 (m, 1H, Hβ), 2.87-2.77 (m, 2H, Hβ), 2.62-2.49 (m, 1H, Hβ), 1.66-1.56 (m, 1H, Lys-Hβ), 1.50-1.36 (m, 3H, Lys-Hβ, 2Hδ), 1.26 (s, 3H, CH3), 1.20-1.10 (m, 2H, Hγ), 1.16 (s, 3H, CH3), ppm. ESI-LC-MS m/z 420.8 [M+2H]2+; HRMS (ESI-MS) calcd. for C43H51FN9O6S [M+H]+ 840.3667 found 840.3693.

5.3.11 H-Inp-His-D-2-Nal-D-Phe-Lys(4-FB)-NH$_2$ (Inp-4-FB-Ipamorelin)

The title peptide was synthesized via automated peptide synthesis and purified by preparative HPLC (20-70% MeCN+0.1% TFA). The title compound was acquired as a white solid (6.30 mg, 6%): $^1$H-NMR (400 MHz, (CD3)2SO); δ 8.79 (s, 1H, His Hε), 8.72 (s, 1H, NH), 8.44 (dd, J=10.8, 6.4 Hz, 2H, NH), 8.19 (d, J=7.8 Hz, 1H, NH), 8.17-8.10 (m, 2H, NH), 7.87-7.81 (m, 2H, F-ArH), 7.80-7.76 (m, 1H, ArH), 7.71 (d, J=7.9 Hz, 2H, ArH), 7.63 (s, 1H, ArH), 7.42-7.35 (m, 2H, ArH), 7.33-7.29 (m, 2H, NH), 7.22-7.18 (m, 6H, ArH), 7.17-7.11 (m, 2H, F-ArH), 7.06 (s, 1H, NH), 6.96 (s, 1H, His Hδ), 4.64-4.56 (m, 1H, Hα), 4.55-4.44 (m, 2H, Hα), 4.15-4.07 (m, 1H, Lys-Hα), 3.19-3.07 (m, 5H, CH2), 2.94 (dd, J=13.6, 5.9 Hz, 1H, CH2), 2.87-2.67 (m, 5H, CH2), 2.58-2.48 (m, 1H, CH2), 2.38-2.29 (m, 1H, Hα), 1.67-1.34 (m, 8H, CH2), 1.15-1.00 (m, 2H, CH2), ppm. ESI-LC-MS m/z 430.9 [M+2H]2+; HRMS (ESI-MS) calcd. for C47H55FN9O6 [M+H]+ 860.4259 found 860.4284.

5.3.12 H-Inp-His-D-2-Nal-D-2-Nal-Lys(4-FB)-NH$_2$ (MMF-01-140-H)

The title peptide was made by automated peptide synthesis and purified by preparative HPLC (20-80% MeCN+0.1% TFA). This delivered a white solid (11.3 mg, 10%): $^1$H-NMR (400 MHz, (CD3)2SO); δ 8.77 (s, 1H, His Hε), 8.51 (d, J=7.5 Hz, 2H, NH), 8.36 (t, J=5.5 Hz, 1H, NH), 8.19-8.10 (m, 2H, NH), 8.05 (d, J=8.7 Hz, 1H, NH), 7.85-7.79 (m, 3H, 2F-ArH, ArH), 7.79-7.74 (m, 3H, ArH), 7.73 (s, 1H, ArH), 7.70 (s, 1H, ArH), 7.68 (d, J=2.4 Hz, 2H, ArH), 7.59 (s, 1H, ArH), 7.43-7.35 (m, 5H, ArH), 7.31-7.27 (m, 2H, NH), 7.20-7.13 (m, 2H, F-ArH), 7.05 (s, 1H, NH), 6.93 (s, 1H, His Hδ), 4.67-4.60 (m, 2H, Hα), 4.52-4.44 (m, 1H, Hα), 4.16-4.08 (m, 1H, Lys-Hα), 3.17-2.93 (m, 7H, CH2), 2.88-2.66 (m, 4H, CH2), 2.53-2.47 (m, 1H, CH2), 2.34-2.25 (m, 1H, Hα), 1.63-1.34 (m, 6H, CH2), 1.32-1.23 (m, 2H, CH2), 1.07-0.95 (m, 2H, CH2), ppm. ESI-LC-MS m/z 455.9 [M+2H]2+; HRMS (ESI-MS) calcd. for C51H57FN9O6 [M+H]+ 910.4416 found 910.4400.

5.3.13 H-Inp-D-2-Nal-D-2-Nal-1-Nal-Lys(4-FB)-NH$_2$ (MMF-01-115-H)

The product was purified by preparative HPLC (25-90% MeCN+0.1% TFA) which yielded a white powder (9.80 mg, 9%): $^1$H-NMR (400 MHz, (CD3)2SO); δ 8.64 (d, J=8.3 Hz, 1H, NH), 8.46 (t, J=5.5 Hz, 1H, NH), 8.33 (s, 1H, NH), 8.25 (d, J=8.4 Hz, 1H, ArH), 8.13 (d, J=8.0 Hz, 1H, NH), 8.09 (d, J=7.5 Hz, 1H, NH), 8.03 (d, J=8.5 Hz, 1H, NH), 8.01-7.97 (m, 1H, NH), 7.89 (d, J=8.2 Hz, 1H, ArH), 7.86-7.80 (m, 2H, F-ArH), 7.79-7.72 (m, 3H, ArH), 7.71-7.66 (m, 2H, ArH), 7.58-7.50 (m, 4H, ArH), 7.44 (d, J=6.9 Hz, 1H, ArH), 7.42-7.34 (m, 5H, ArH), 7.31-7.25 (m, 2H, ArH), 7.21-7.15 (m, 3H, 2F-ArH), 7.07 (s, 1H, NH), 7.02 (d, J=8.4 Hz, 1H, ArH), 4.72-4.65 (m, 1H, Hα), 4.62-4.50 (m, 2H, Hα), 4.19 (dd, J=13.3, 8.4 Hz, 1H, Lys-Hα), 3.61 (dd, J=14.3, 3.9, 1H, CH2), 3.24-3.00 (m, 5H, CH2), 2.97-2.89 (m, 1H, CH2), 2.82-2.49 (m, 5H, CH2), 2.29-2.19 (m, 1H, Inp-Hα), 1.78-1.66 (m, 1H, CH2), 1.66-1.54 (m, 1H, CH2), 1.53-1.40 (m, 5H, CH2), 1.40-1.16 (m, 2H, CH2), ppm. ESI-LC-MS m/z 477.4 [M+4H−F]2+; HRMS (ESI-MS) calcd. for C58H61FN7O6 [M+H]+ 970.4667 found 970.4693.

5.3.14 H-His-D-Trp-Ala-Trp-D-Phe-Lys(4-FB)-NH$_2$ (4-FB-GHRP-6)

The product was purified by preparative HPLC (15-80% MeCN+0.1% TFA). This yielded a white powder (9.60 mg, 7%): $^1$H-NMR (400 MHz, CD3OD); His, D-Trp, Trp, D-Phe, 4-FB: δ 8.50 (s, 1H, His Hε), 7.88-7.80 (m, 2H, F-ArH), 7.57 (d, J=7.9 Hz, 1H, ArH), 7.49 (d, J=7.8 Hz, 1H, ArH), 7.30 (t, J=8.2 Hz, 2H, ArH), 7.26-6.95 (m, 14H, 13ArH, His Hδ), 4.53-4.46 (m, 2H, Hα), 4.37-4.30 (m, 2H, Hα), 3.26-3.04 (m, 6H, Hβ), 2.87 (d, J=8.0 Hz, 2H, Hβ), Lys: 4.04 (dd, J=10.2, 4.0 Hz, 1H, Hα), 3.26-3.04 (m, 2H, Hε), 1.81-1.70 (m, 1H, Hβ), 1.58-1.43 (m, 3H, 2Hδ, Hβ), 1.06-0.97 (m, 2H, Hγ), Ala: 3.94 (q, J=7.3 Hz, 1H, Hα), 0.87 (d, J=7.3 Hz, 3H, CH3) ppm. ESI-LC-MS m/z 498.4 [M+2H]2+; HRMS (ESI-MS) calcd. for C53H59FN12O7Na [M+Na]+1017.4511 found 1017.4522.

5.3.15 H-His-D-Trp-Ala-Trp-D-Phe-Dpr(4-FB)-NH$_2$ (Dpr-4-FB-GHRP-6)

Preparative HPLC (25-70% MeCN+0.1% TFA) gave the title compound as a white solid (19.8 mg, 14%): $^1$H-NMR (400 MHz, CD3OD); His, D-Trp, Trp, D-Phe, 4-FB: δ 8.58 (d, J=1.3 Hz, 1H, His Hε), 7.82-7.75 (m, 2H, F-ArH), 7.52 (d, J=7.9 Hz, 1H, ArH), 7.40 (d, J=7.9 Hz, 1H, ArH), 7.27 (dd, J=8.6, 1.5 Hz, 2H, ArH), 7.15-7.07 (m, 5H, ArH), 7.06-6.98 (m, 6H, ArH), 6.97-6.89 (m, 3H, 2ArH, His Hδ), 4.54-4.45 (m, 1H, Hα), 4.44-4.30 (m, 3H, Hα), 3.22-2.98 (m, 6H, Hβ), 2.93-2.74 (m, 2H, Hβ), Dpr: 4.54-4.45 (m, 1H, Hα), 3.67 (dd, J=13.8, 5.6 Hz, 1H, Hβ), 3.54 (dd, J=13.8, 7.8 Hz, 1H, Hβ), Ala: 3.93 (q, J=7.3 Hz, 1H, Hα), 0.86 (d, J=7.3 Hz, 3H, CH3) ppm. ESI-LC-MS m/z 477.4 [M+2H]2+; HRMS (ESI-MS) calcd. for C50H54FN12O7 [M+H]+ 953.4223 found 953.4237.

5.3.16 H-D-Ala-D-2-Nal-Ala-Trp-D-Phe-Lys-NH$_2$ (GHRP-2)

Purification by preparative HPLC (25-70% MeCN+0.1% TFA) delivered the title peptide as a white powder (19.7 mg, 17%): $^1$H-NMR (400 MHz, CD3OD); D-2-Nal, Trp, D-Phe: δ 7.76 (d, J=9.2 Hz, 2H, ArH), 7.73 (s, 1H, ArH), 7.65 (s, 1H, ArH), 7.51-7.47 (m, 1H, ArH), 7.44-7.37 (m, 2H, ArH), 7.35 (dd, J=8.4, 1.7 Hz, 1H, ArH), 7.25-7.14 (m, 4H, ArH), 7.09-7.01 (m, 4H, ArH), 7.00 (s, 1H, ArH), 4.77 (dd, J=10.9, 4.6 Hz, 1H, Hα), 4.49 (t, J=6.8 Hz, 1H, Hα), 4.36 (t, J=7.6 Hz, 1H, Hα), 3.11 (t, J=6.7 Hz, 2H, Hβ), 3.07 (d, J=4.5 Hz, 1H, Hβ), 2.88-2.70 (m, 3H, Hβ), D-Ala, Ala: 4.23 (q, J=7.1 Hz, 1H, Hα), 3.79 (q, J=7.0 Hz, 1H, Hα), 1.27 (d, J=7.2 Hz, 3H, CH3), 1.00 (d, J=7.1 Hz, 3H, CH3), Lys: 4.16 (dd, J=10.3, 4.1 Hz, 1H, Hα), 2.88-2.70 (m, 2H, Hε), 1.82-1.72 (m, 1H, Hβ), 1.56-1.43 (m, 3H, Hβ, 2Hδ), 1.07-0.96 (m, 2H, Hγ), ppm. ESI-LC-MS m/z 409.9 [M+2H]2+; HRMS (ESI-MS) calcd. for C45H55N9O6Na [M+Na]+840.4204 found 840.4173.

5.3.17 H-Inp-D-2-Nal-D-2-Nal-Phe-Lys(FP)-NH$_2$ (2-FP-G-7039)

The product was purified by preparative HPLC (30-80% MeCN+0.1% TFA). This yielded a white powder (mg, %): $^1$H-NMR (400 MHz, CD3OD); δ 8.22-8.17 (m, 2H, amide NH), 8.11 (d, J=7.5 Hz, 2H, amide NH), 8.05 (dd, J=7.9, 2.0 Hz, 1H, amide NH), 7.79-7.66 (m, 6H, ArH), 7.58 (s, 1H, ArH), 7.48 (s, 1H, ArH), 7.44-7.34 (m, 4H, ArH), 7.28 (d, J=8.4 Hz, 1H, ArH), 7.16-7.06 (m, 4H, ArH), 4.96-4.90 (m, 0.5H, HC-F), 4.82-4.77 (m, 0.5H, HC-F), 4.68-4.56 (m, 2H, Hα), 4.55-4.48 (m, 1H, Hα), 4.28.4.21 (m, 1H, Lys-Hα), 3.22-3.13 (m, 4H, CH2), 3.12-2.64 (m, 8H, CH2), 2.34-2.26 (m, 1H, Inp-Hα), 1.89-1.78 (m, 1H, CH2), 1.76-1.64 (m, 1H, CH2), 1.60-1.23 (m, 11H, 8CH2, CH3), ppm.

Figure 3:
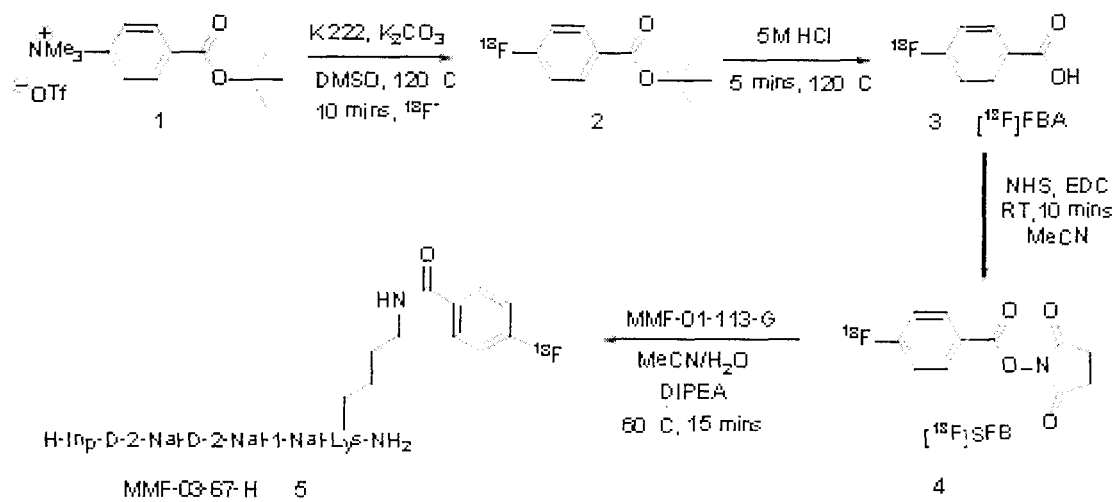
FIG. 3 Scheme showing the synthesis of the [$^{18}$F]MMF-01-115-H lead compound 5 by prosthetic group radiolabelling with [$^{18}$F]SFB (4).
Figure 4:
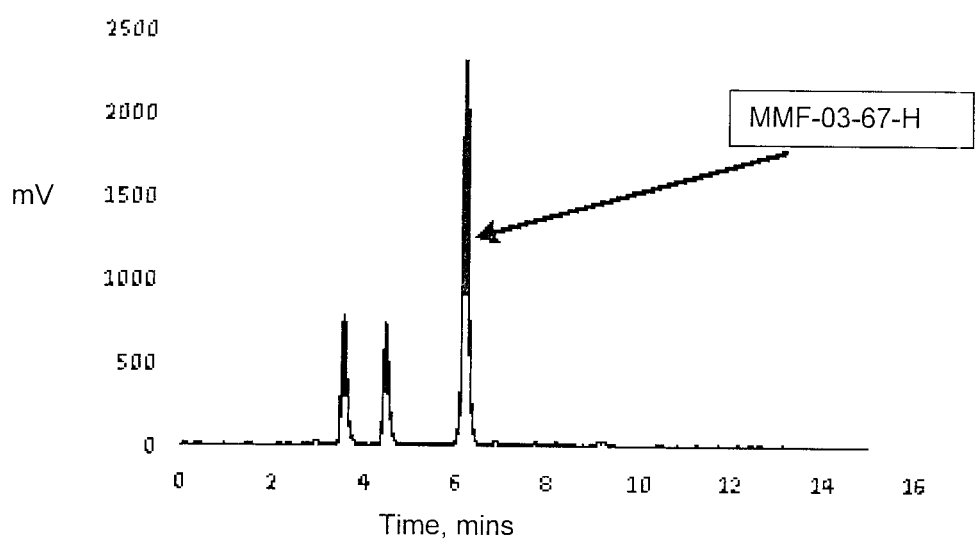
FIG. 4 Radio-chromatogram of the crude reaction mixture obtained by the radiolabelling of the precursor MMF-01-113-G with [$^{18}$F]SFB.
Figure 46A:
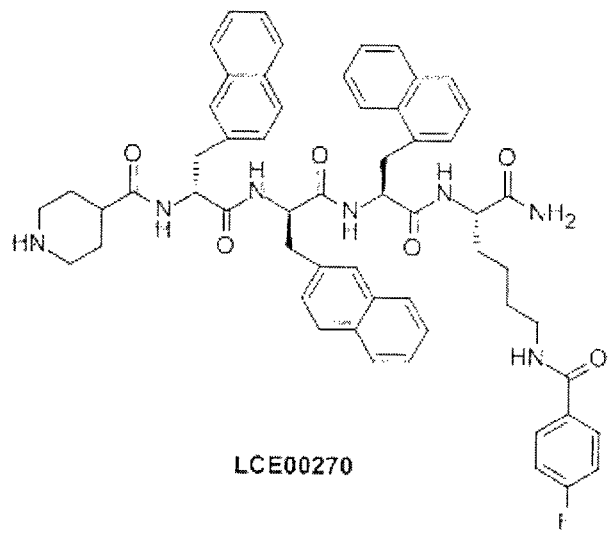
FIG. 46 (A): chemical structure of LCE00270; (B) chemical structure of LCE00295.
Figure 46B:
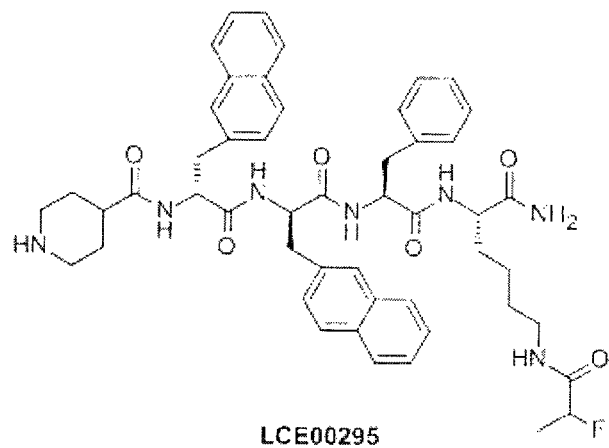

Peptidomimetics have been designed based upon known growth hormone secretagogues, which consist of 5 or 6 unnatural amino acid residues. Analogues containing non-radioactive fluoride were prepared and evaluated in vitro for GHSR-1a affinity. Promising chemical entities were identified as MMF-01-115-H (LCE270) and 2-FP-G-7039 (LCE295) with IC50 values for the GHS-R1a of 68.8 nM and 12 nM respectively. These leads compounds are illustrated in FIG. 46. In addition, using ACD/Log P software, the lipophilicities of these compounds were computed and it was found that LCE00270 and LCE00295 had high Log P values of 8.76±0.88 and 5.19±0.88 respectively. However, given that these compounds may be used as imaging agents that may be administered to a subject by intravenous injection, oral bioavailability (via oral administration) may not be a primary concern. These lead compounds may require further modification in order to adjust lipophilicity. Having chosen two lead compounds, the precursor of the first lead compound (MMF-01-113-G, LCE244) was radiolabelled using the [18F]SFB prosthetic group (4) by coupling it to the free lysine side-chain. The scheme of FIG. 3 shows the procedure used to radiolabel MMF-01-113-G with [18F] SFB. This synthetic pathway resulted in the formation of the radiolabelled version of the lead compound (MMF-03-67-H, 5) in a crude radiochemical yield of 35% by HPLC. The obtained reaction mixture is shown in FIG. 4, with the product eluting at 6.1 minutes, which is in agreement to the non-radioactive standard. Preparation of the prosthetic group 4 prior to coupling to the peptidomimetic proceeded in high yield and purity, as indicated in FIG. 5.

The synthesized compounds are listed in Table 1. Peptidomimetic chromatogram are illustrated in FIGS. 11-19, the $^1$H-NMR spectra are illustrated in FIGS. 20-36 and the peptidomimetic displacement curves are illustrated in FIGS. 37-45.

Figure 5:
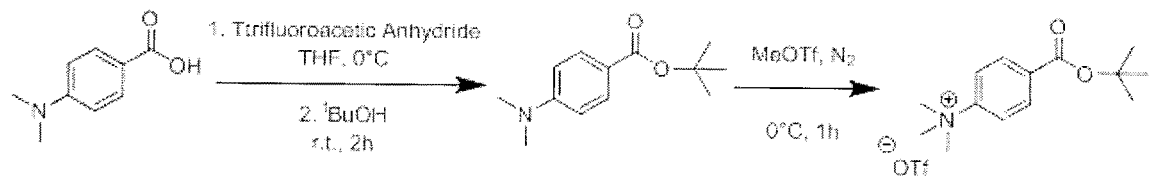
FIG. 5 Scheme showing the synthesis of the precursor 4-(tert-butoxycarbonyl)-N,N,N-trimethylbenzenammonium triflate salt.
Figure 6:
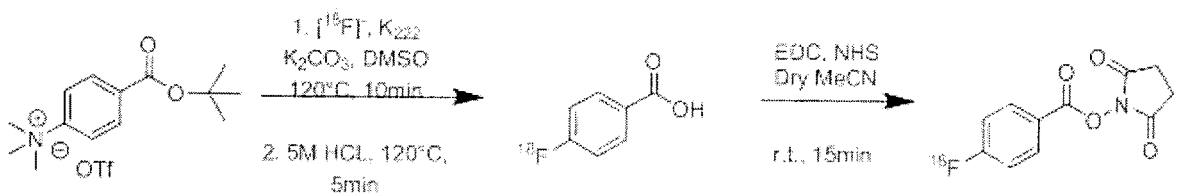
FIG. 6 Scheme showing the synthesis of $^{18}$F-labelled [1-Nal$^4$, Lys$^5$(4-fluorobenzoic acid)]G-7039 (also referred to as MMF-01-115-H or H-Inp-D-2-Nal-D-2-Nal-1-Nal-Lys(4-FB)-NH2).
Figure 6:
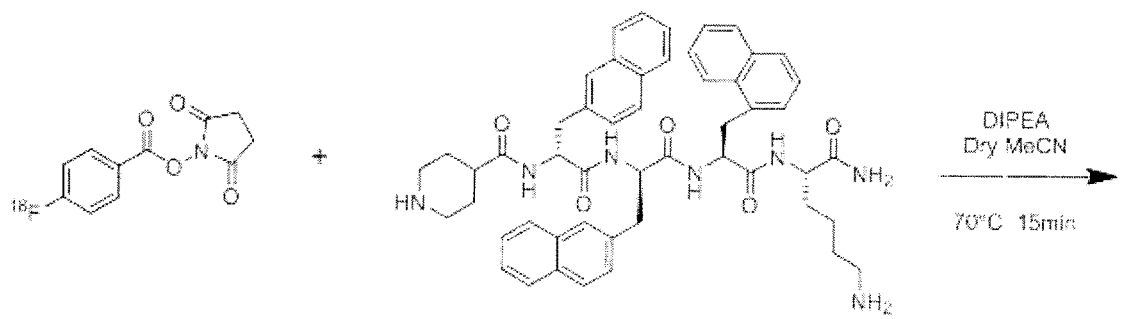
Figure 6:
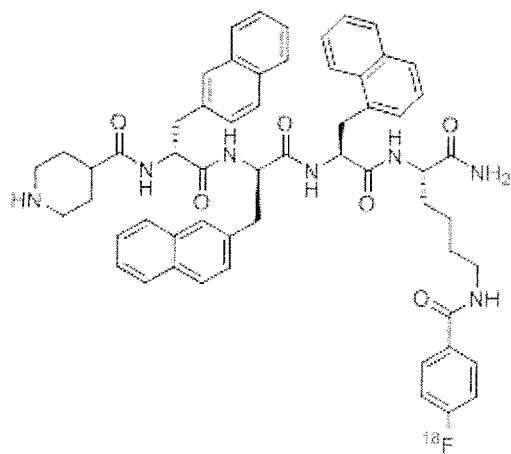

The synthesis of the precursor for obtaining MMF-01-115-H is shown in FIG. 5, while the synthesis of MMF-01-115-H is shown in FIG. 6.

Figure 10:
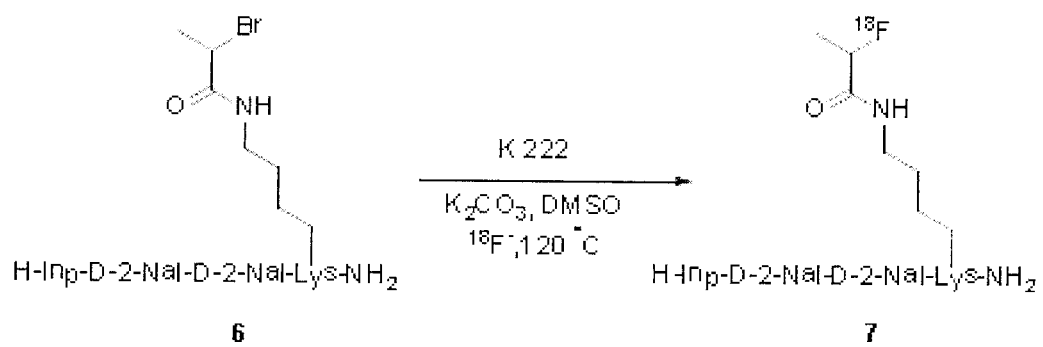
FIG. 10 Scheme of proposed radiolabelling of a brominated precursor to give the [$^{18}$F]2-FP-G-7039 compound.
Figure 11:
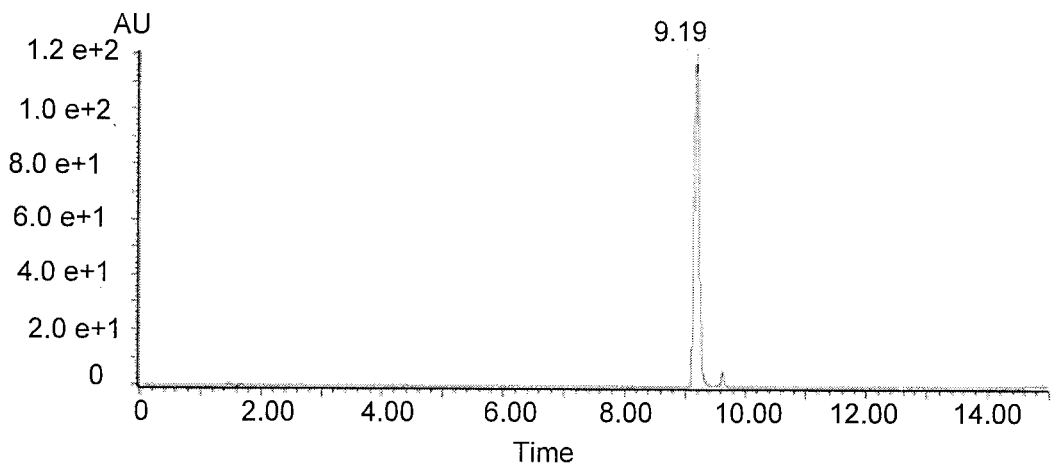
FIG. 11 Peptidomimetic chromatogram: LCE00210: H-Aib-His-D-2-Nal-D-Phe-Lys-NH2
Figure 12:
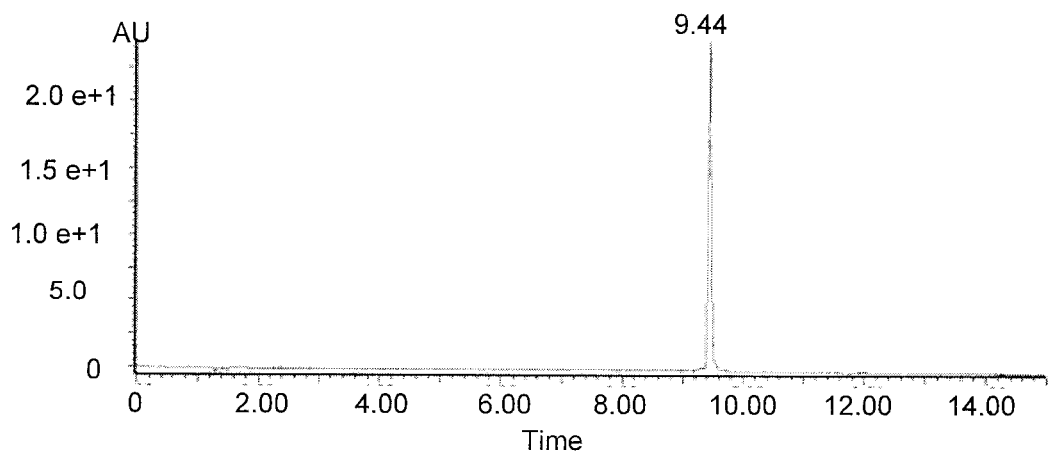
FIG. 12 Peptidomimetic chromatogram LCE00211: H-Aib-His-D-2-Nal-D-Phe-Lys(4-FB)-NH2.
Figure 13:
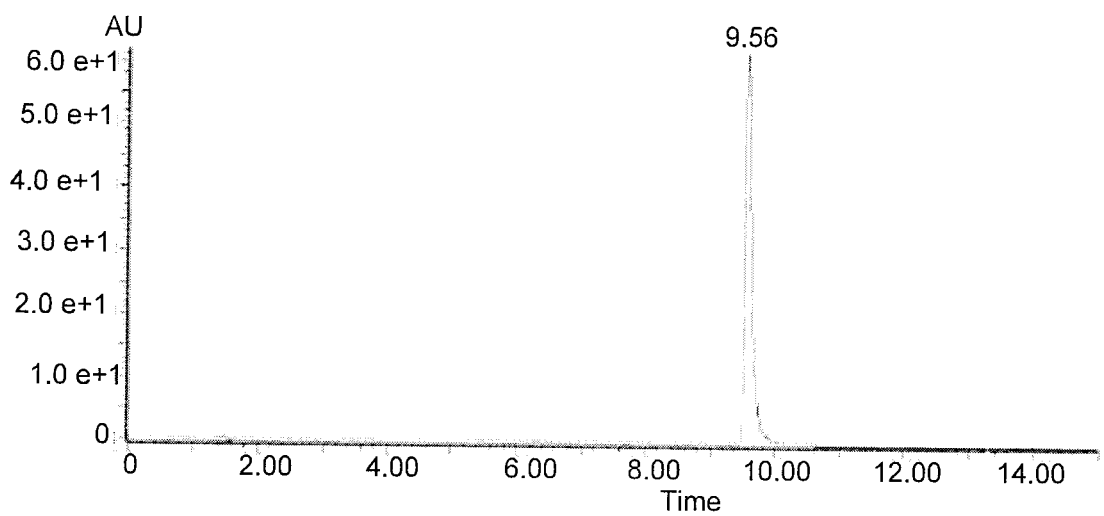
FIG. 13 Peptidomimetic chromatogram LCE00217: H-Aib-His-D-2-Nal-D-Phe-Lys(AEEA-4-FB)-NH2.
Figure 14:
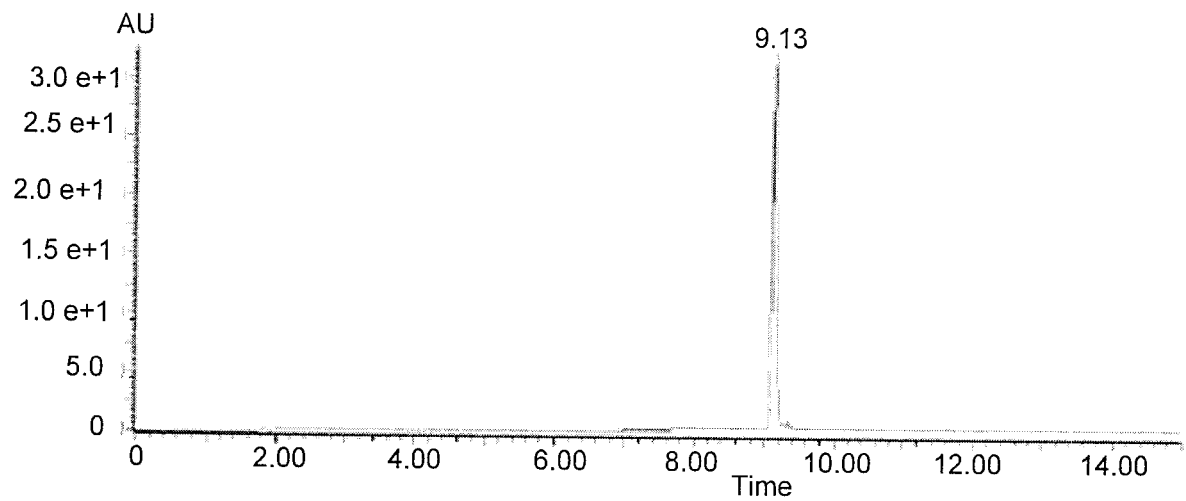
FIG. 14 Peptidomimetic chromatogram LCE00239: H-His-D-Trp-Ala-Trp-D-Phe-Lys-NH2.
Figure 15:
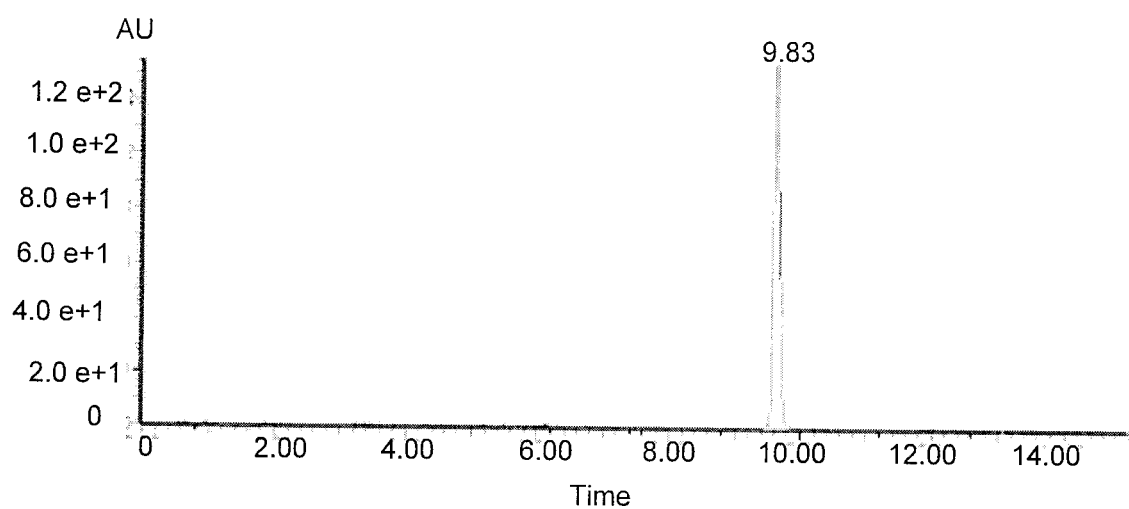
FIG. 15 Peptidomimetic chromatogram LCE00240: H-Ala-His-D-2-Nal-Ala-Trp-D-Phe-Lys-NH2.
Figure 16A:
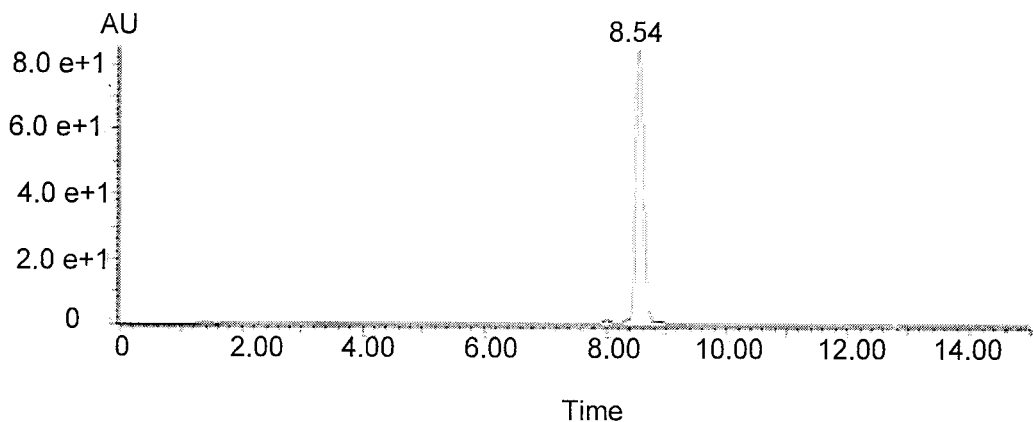
FIG. 16 (A) Peptidomimetic chromatogram LCE00243: H-Inp-D-2-Nal-D-2-Nal-Phe-Lys(4-FB)-NH2; (B) Peptidomimetic chromatogram LCE00244: H-Inp-D-2-Nal-D-2-Nal-1-Nal-Lys-NH2; (C) Peptidomimetic chromatogram LCE00245: H-Inp-D-2-Nal-D-2-Nal-Phe-Lys-NH2.
Figure 16B:
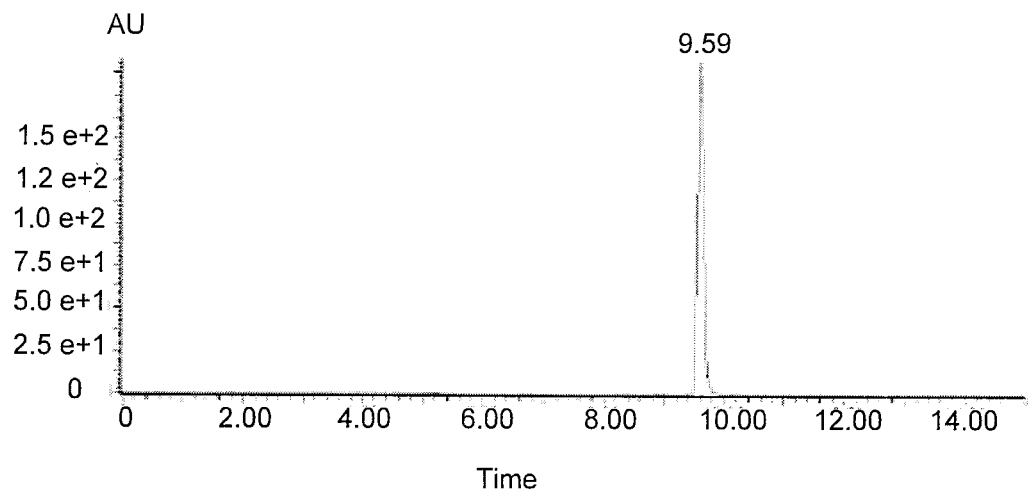
Figure 16C:
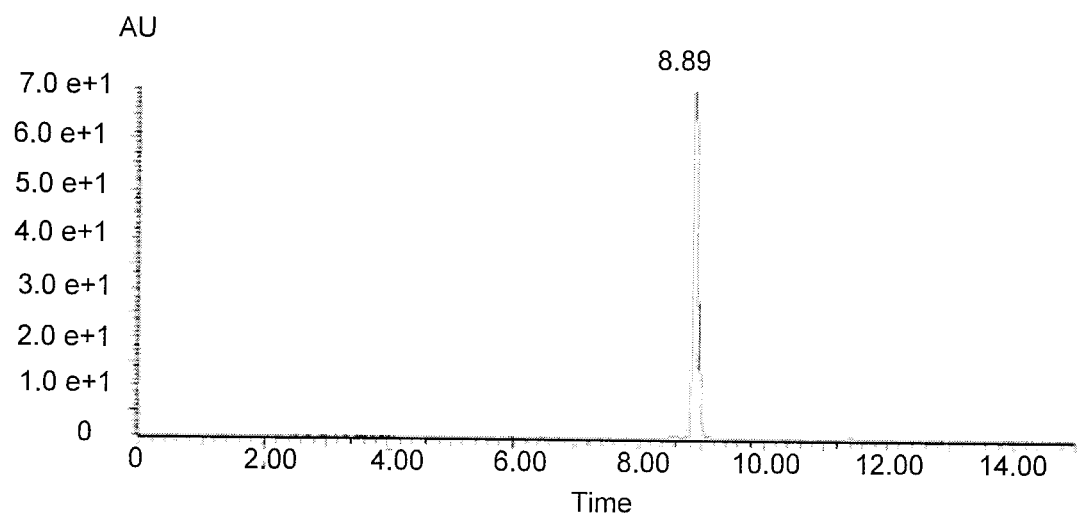
Figure 17A:
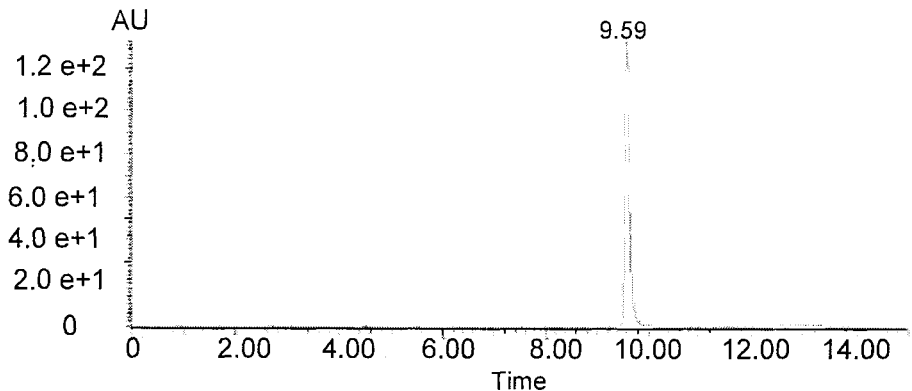
FIG. 17 (A) Peptidomimetic chromatogram LCE00246: H-Inp-His-D-2-Nal-D-2-Thi-Lys(4-FB)-NH2; (B) Peptidomimetic chromatogram LCE00267: H-Aib-His-D-2-Nal-D-2-Thi-Lys(4-FB)-NH2; (C) Peptidomimetic chromatogram LCE00268: H-Inp-His-D-2-Nal-D-Phe-Lys(4-FB)-NH2.
Figure 17B:
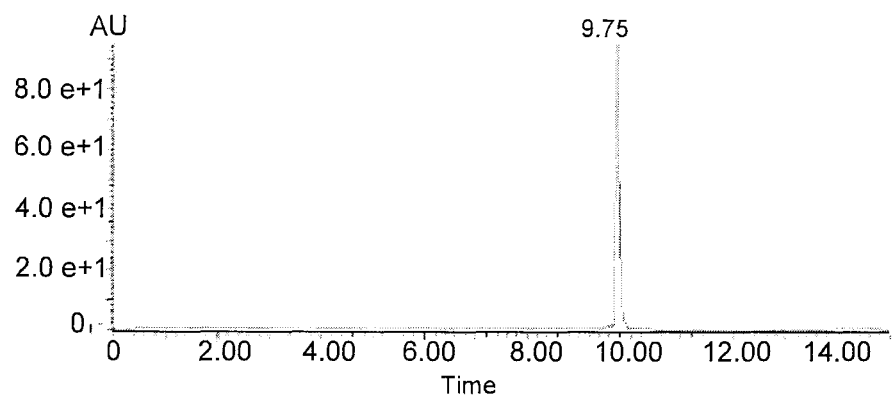
Figure 17C:
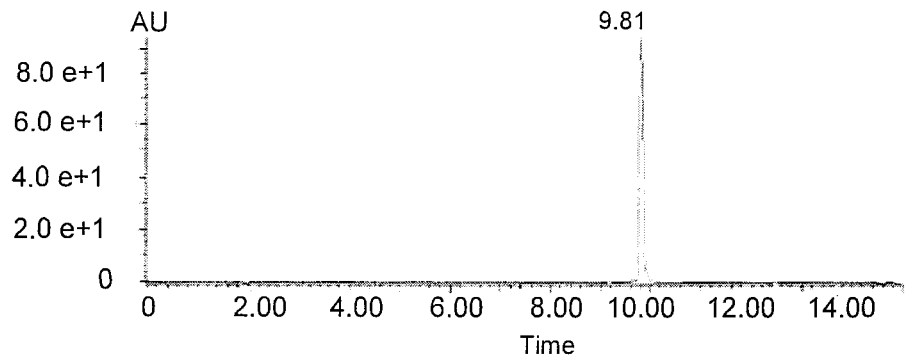
Figure 18A:
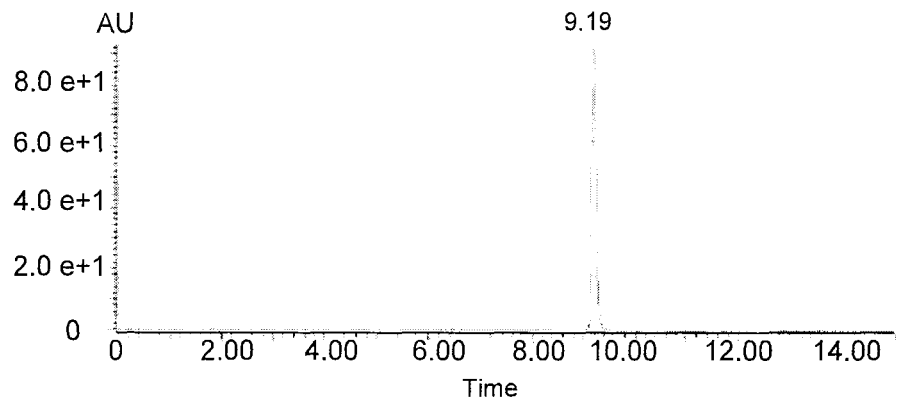
FIG. 18 (A) Peptidomimetic chromatogram LCE00269: H-Inp-His-D-2-Nal-D-2-Nal-Lys(4-FB)-NH2; (B) Peptidomimetic chromatogram LCE00270: H-Inp-D-2-Nal-D-2-Nal-1-Nal-Lys(4-FB)-NH2; (c) Peptidomimetic chromatogram LCE00272: H-His-D-Trp-Ala-Trp-D-Phe-Lys(4-FB)-NH2.
Figure 18B:
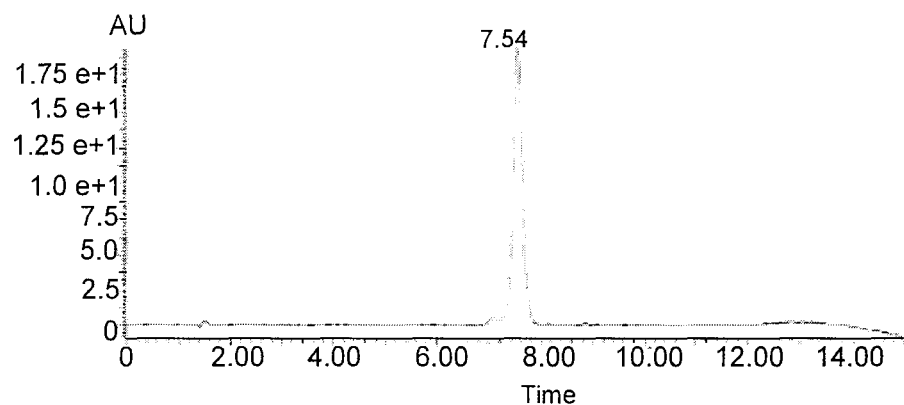
Figure 18C:
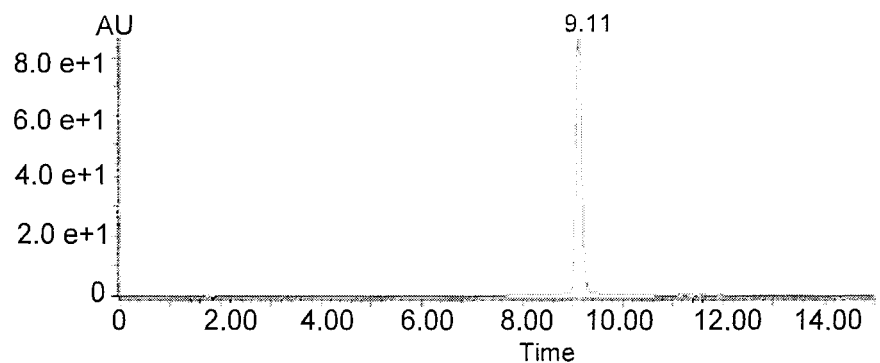
Figure 19A:
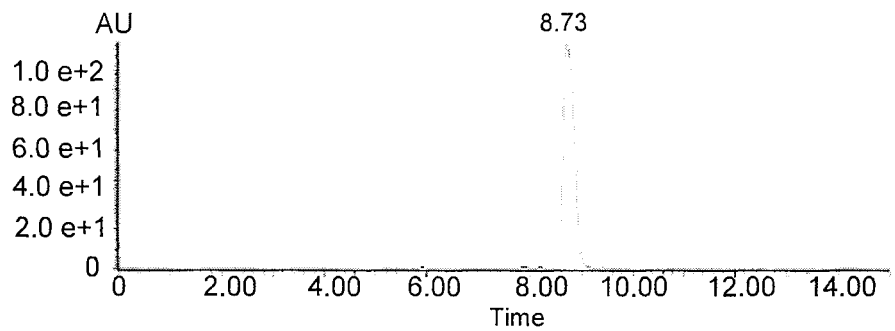
FIG. 19 (A) Peptidomimetic chromatogram LCE00281: H-His-D-Trp-Ala-Trp-D-Phe-Dpr(4-FB)-NH2; (B) Peptidomimetic chromatogram LCE00282: H-D-Ala-D-2-Nal-Ala-Trp-D-Phe-Lys-NH2; (C) Peptidomimetic chromatogram LCE00295: H-Inp-D-2-Nal-D-2-Nal-Phe-Lys(2-FP)-$NH_2$.
Figure 19B:
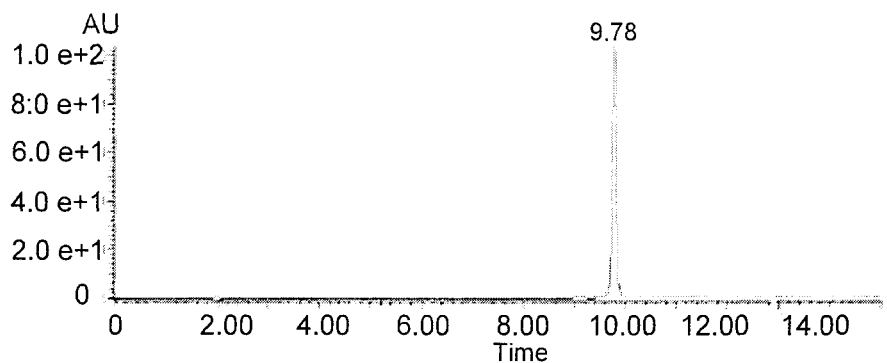
Figure 19C:
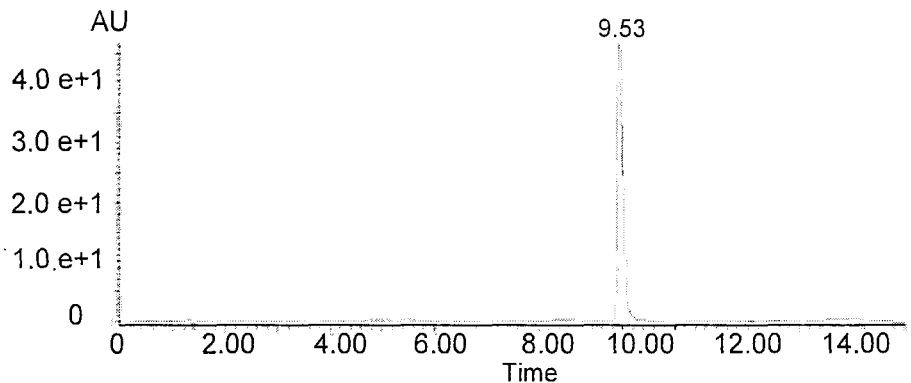
Figures 19, 20:
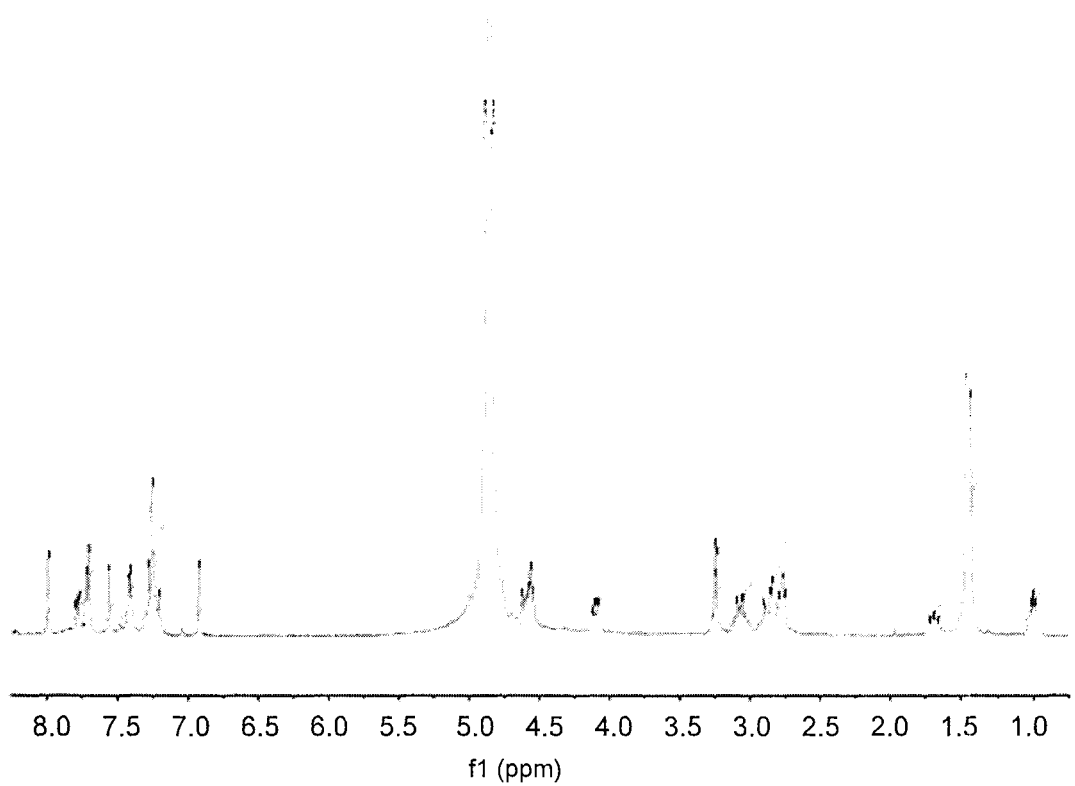
FIG. 20 Peptidomimetic $^1$H-NMR Spectrum LCE00210: H-Aib-His-D-2-Nal-D-Phe-Lys-$NH_2$.
Figure 21:
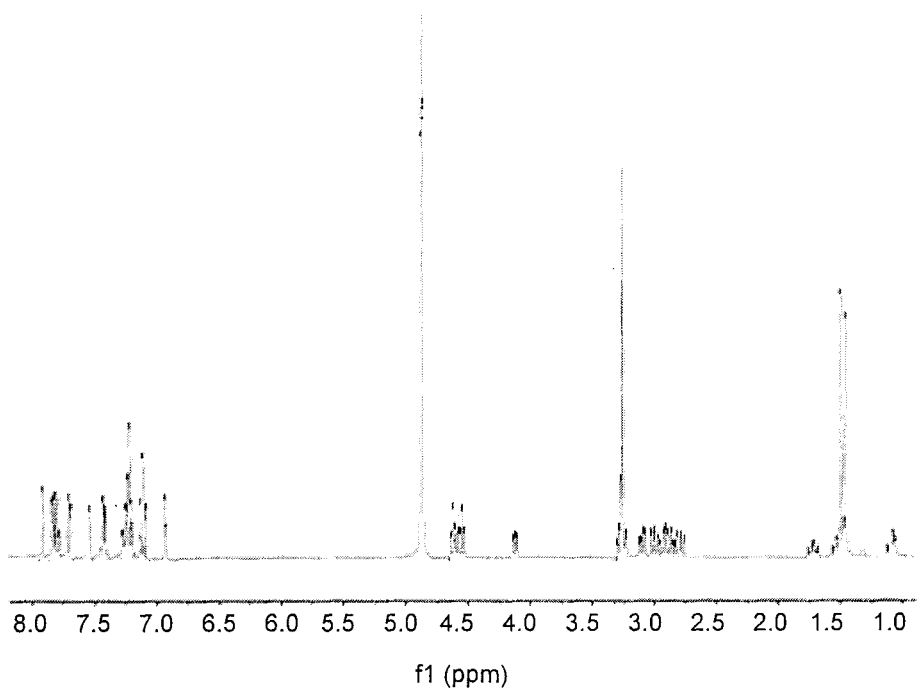
FIG. 21 Peptidomimetic $^1$H-NMR Spectrum LCE00211: H-Aib-His-D-2-Nal-D-Phe-Lys(4-FB)-$NH_2$.
Figure 22:
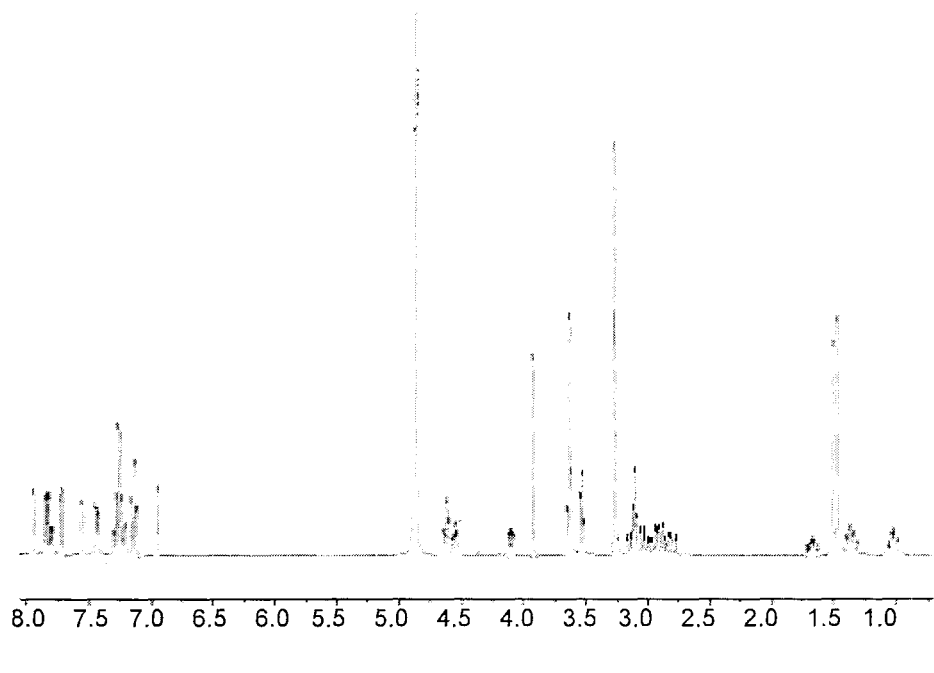
FIG. 22 Peptidomimetic $^1$H-NMR Spectrum LCE00217: H-Aib-His-D-2-Nal-D-Phe-Lys(4-FB-AEEA)-$NH_2$.
Figure 23:
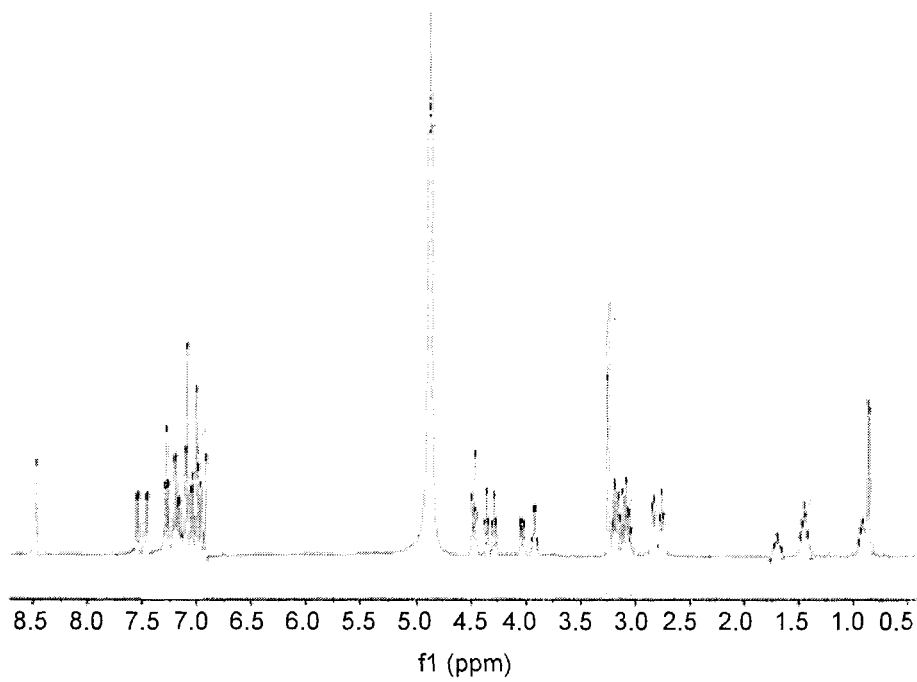
FIG. 23 Peptidomimetic $^1$H-NMR Spectrum LCE00239: H-His-D-Trp-Ala-Trp-D-Phe-Lys-$NH_2$.
Figure 24:
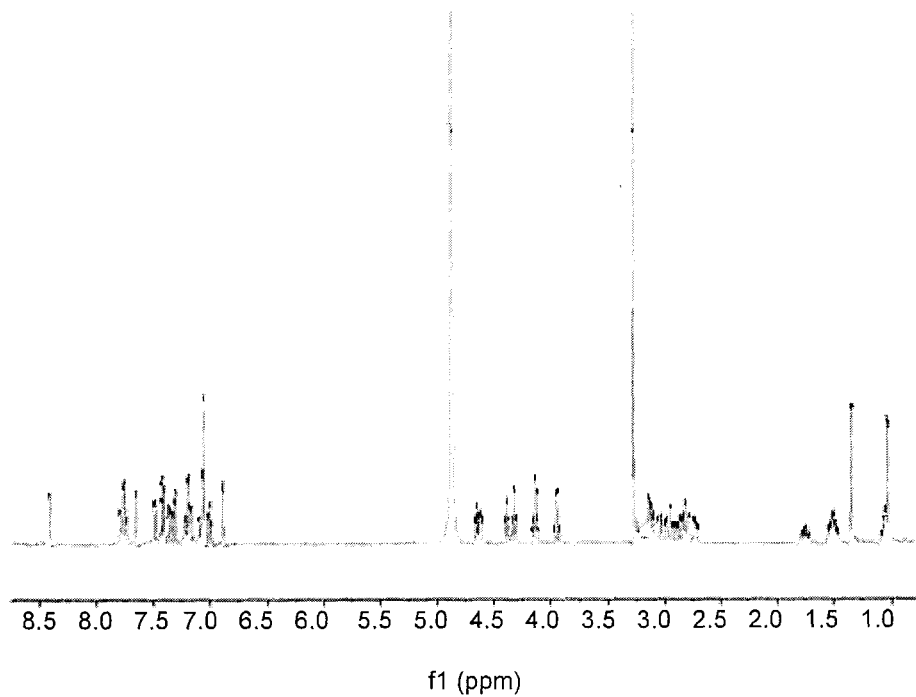
FIG. 24 Peptidomimetic $^1$H-NMR Spectrum LCE00240: H-Ala-His-D-2-Nal-Ala-Trp-D-Phe-Lys-$NH_2$.
Figure 25:
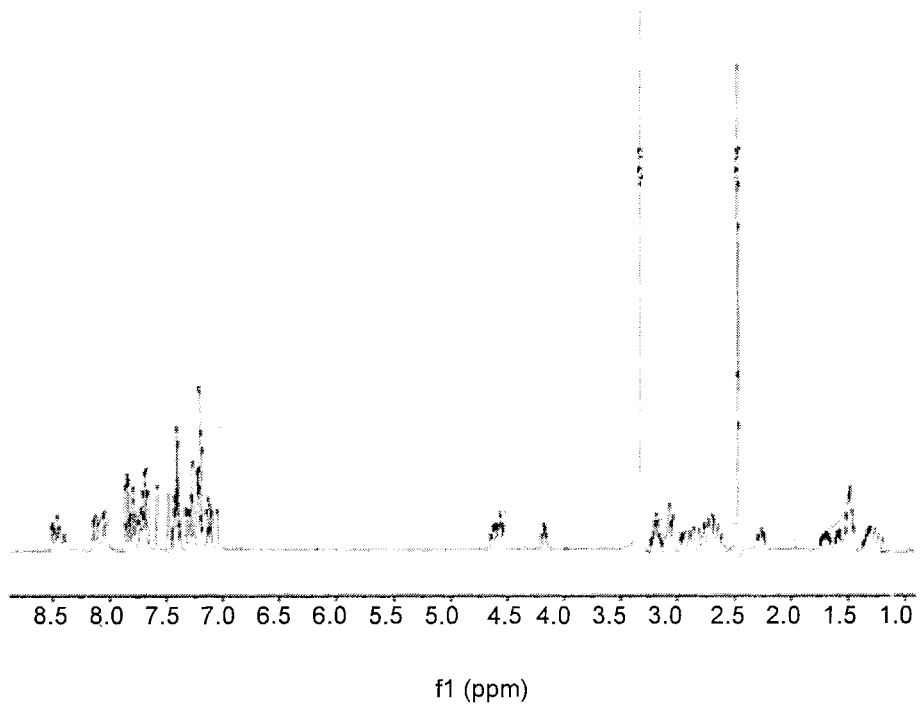
FIG. 25 Peptidomimetic $^1$H-NMR Spectrum LCE00243: H-Inp-D-2-Nal-D-2-Nal-Phe-Lys(4-FB)-$NH_2$.
Figure 26:
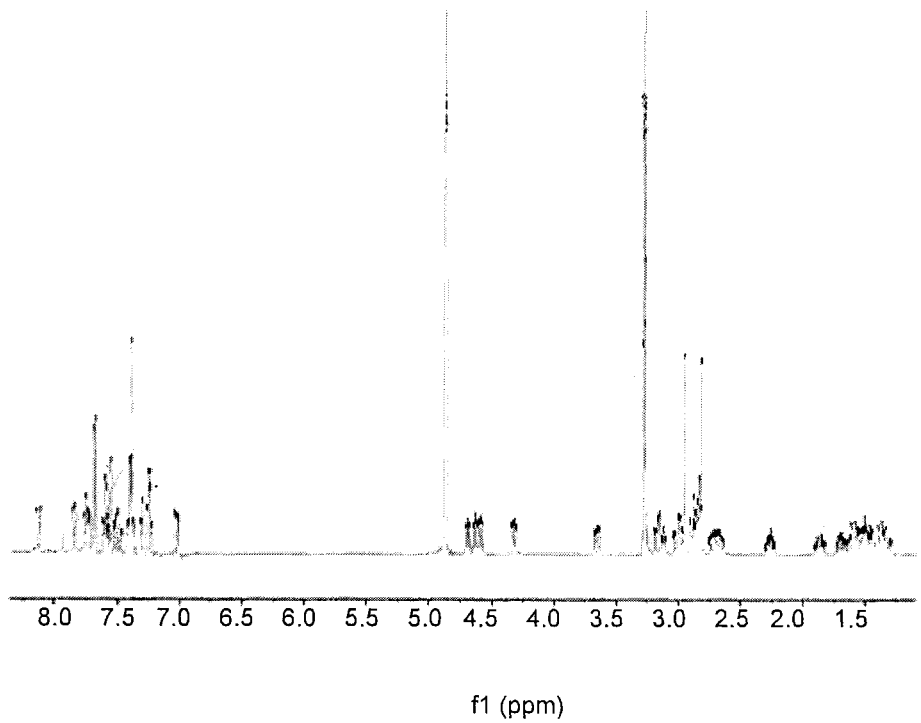
FIG. 26 Peptidomimetic $^1$H-NMR Spectrum LCE00244: H-Inp-D-2-Nal-D-2-Nal-1-Nal-Lys-$NH_2$.
Figure 27:
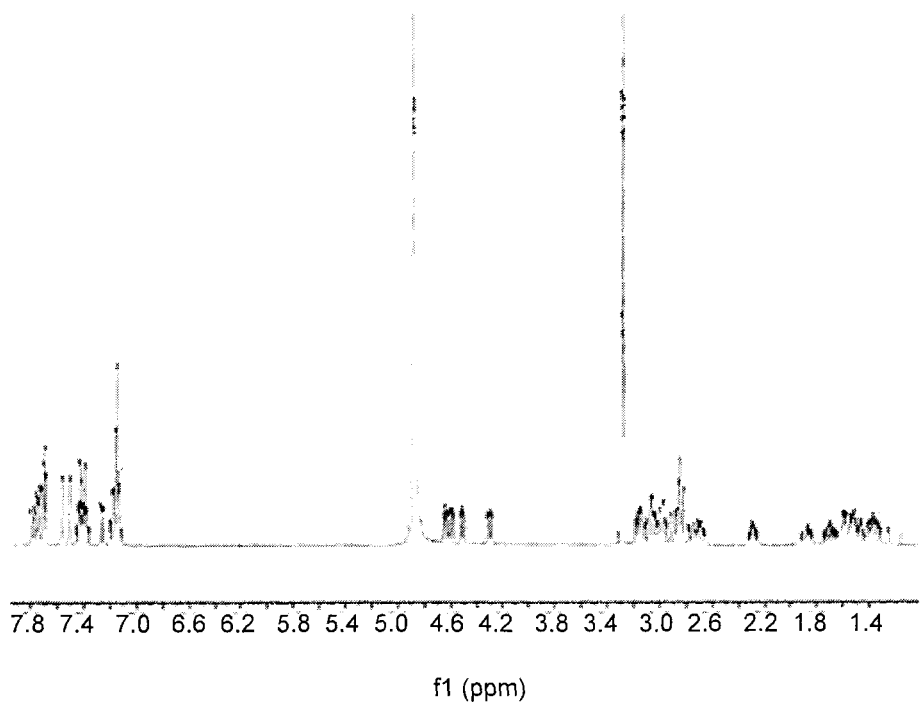
FIG. 27 Peptidomimetic $^1$H-NMR Spectrum LCE00245: H-Inp-D-2-Nal-D-2-Nal-Phe-Lys-$NH_2$.
Figure 28:
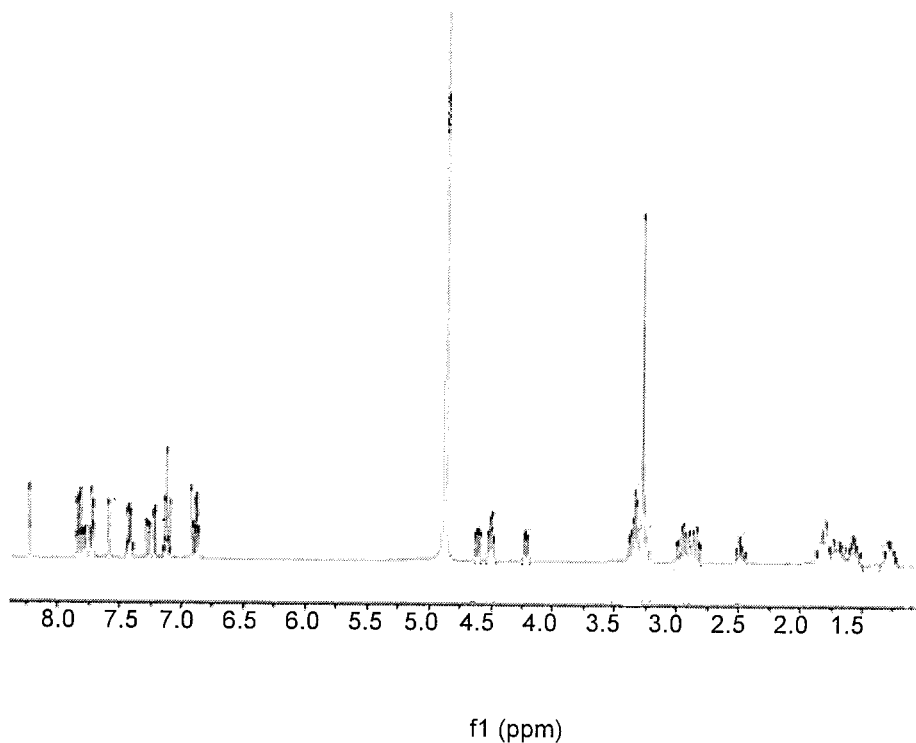
FIG. 28 Peptidomimetic $^1$H-NMR Spectrum LCE00246: H-Inp-His-D-2-Nal-D-2-Thi-Lys(4-FB)-$NH_2$.
Figure 29:
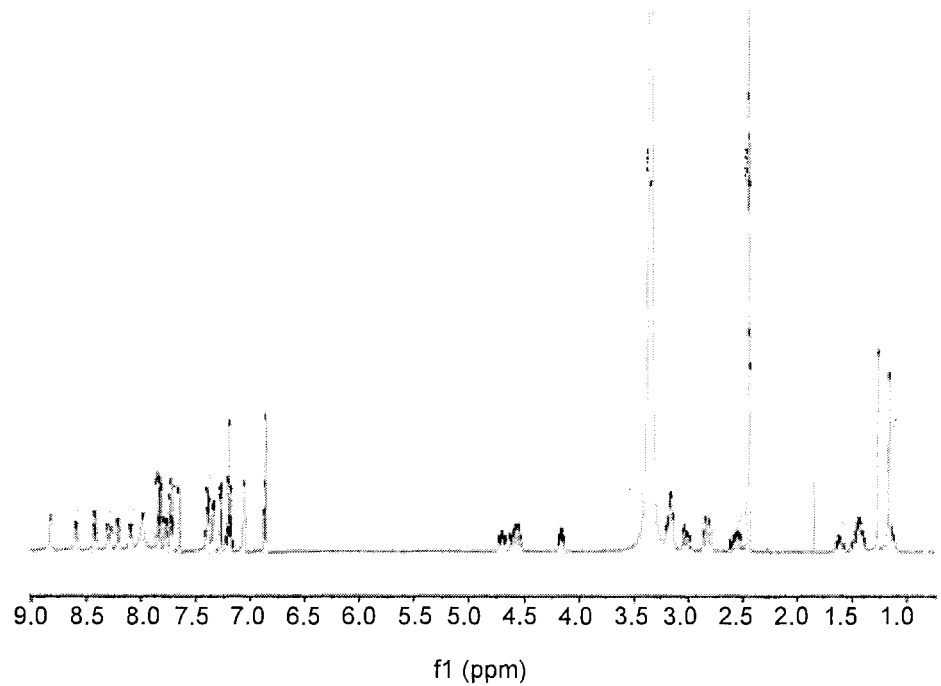
FIG. 29 Peptidomimetic $^1$H-NMR Spectrum LCE00267: H-Aib-His-D-2-Nal-D-2-Thi-Lys(4-FB)-$NH_2$.
Figure 30:
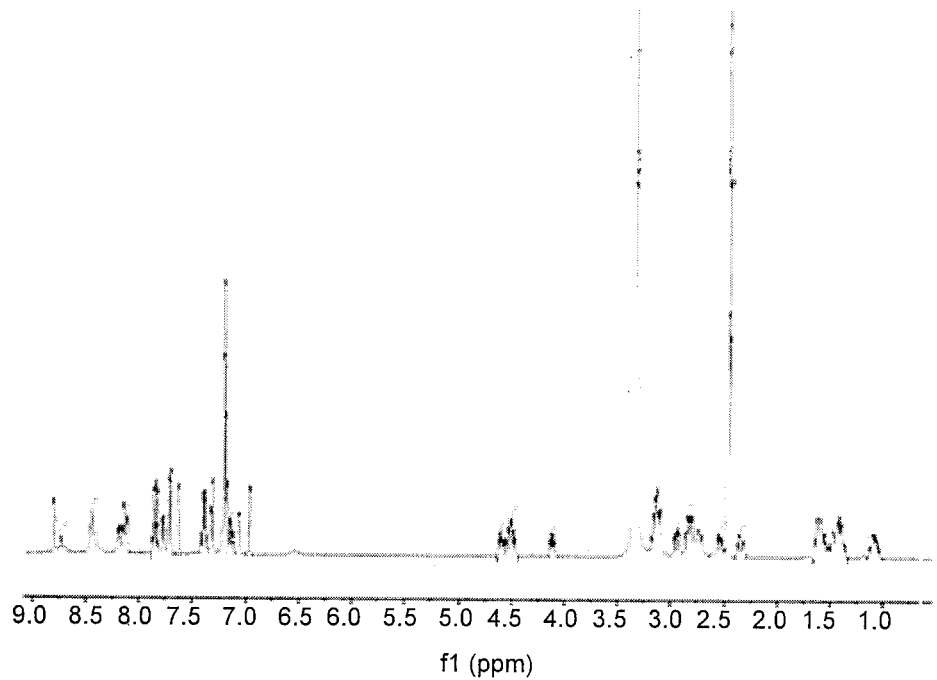
FIG. 30 Peptidomimetic $^1$H-NMR Spectrum LCE00268: H-Inp-His-D-2-Nal-D-Phe-Lys(4-FB)-$NH_2$.
Figure 31:
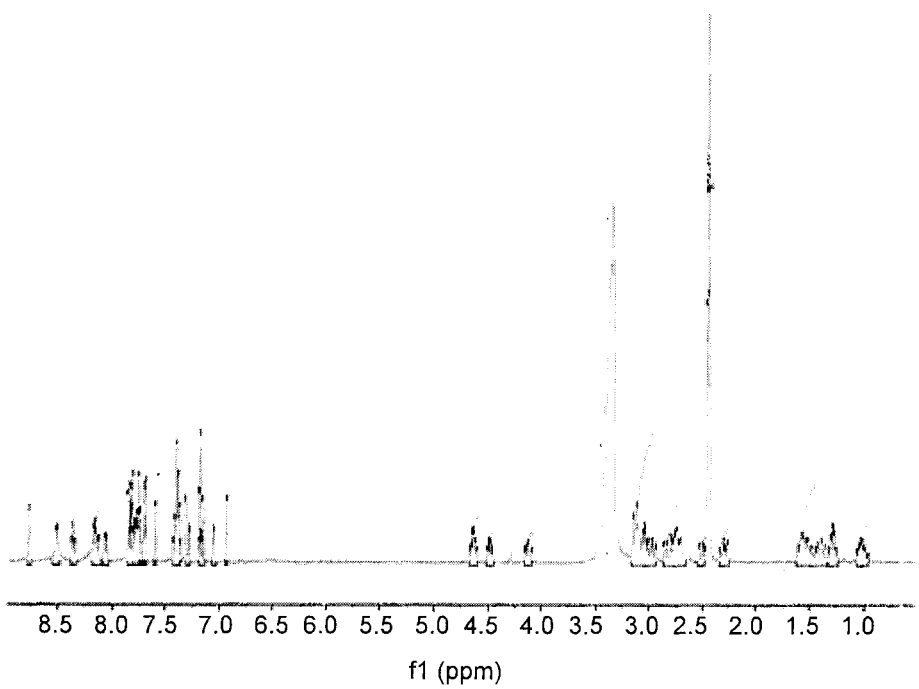
FIG. 31 Peptidomimetic $^1$H-NMR Spectrum LCE00269: H-Inp-His-D-2-Nal-D-2-Nal-Lys(4-FB)-$NH_2$.
Figure 32:
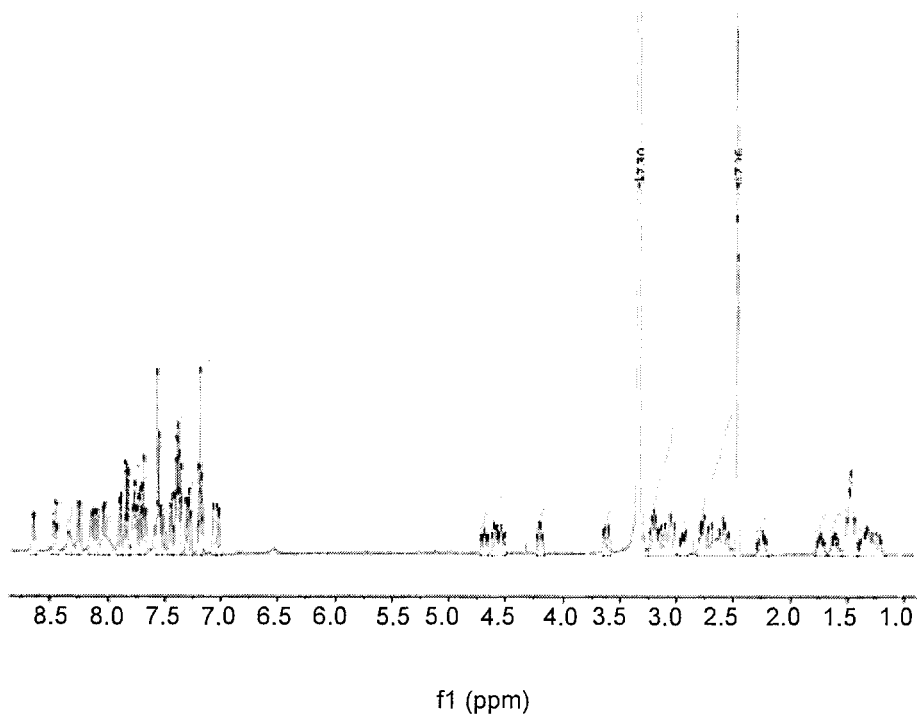
FIG. 32 Peptidomimetic $^1$H-NMR Spectrum LCE00270: H-Inp-D-2-Nal-D-2-Nal-1-Nal-Lys(4-FB)-$NH_2$.
Figure 33:
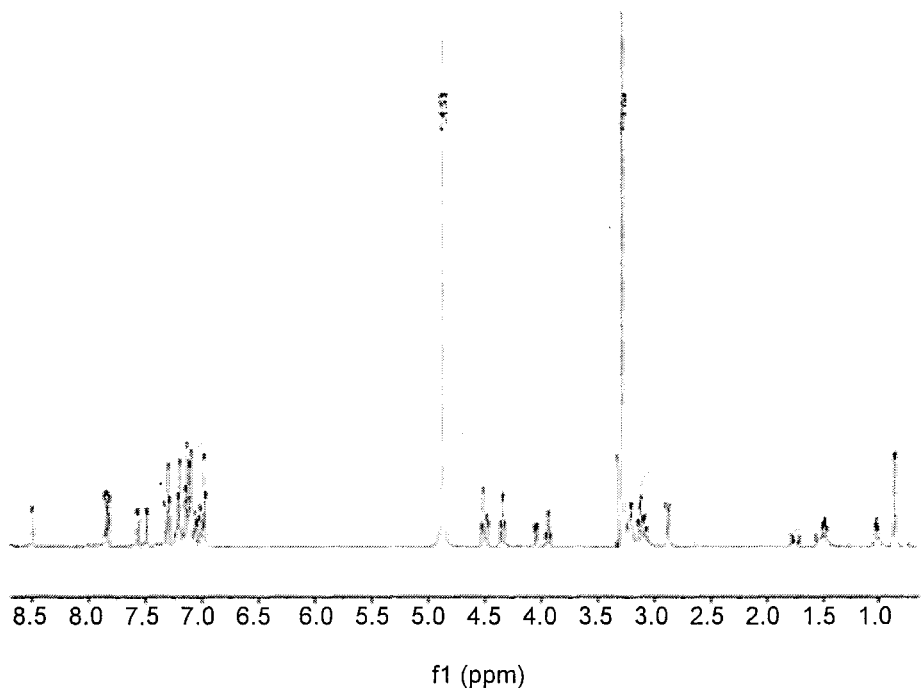
FIG. 33 Peptidomimetic $^1$H-NMR Spectrum LCE00272: H-His-D-Trp-Ala-Trp-D-Phe-Lys(4-FB)-$NH_2$.
Figure 34:
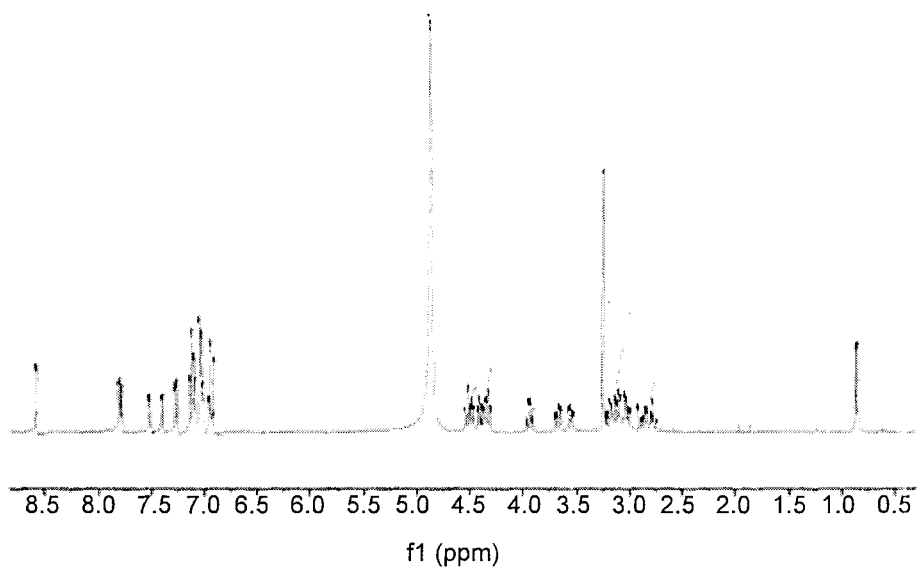
FIG. 34 Peptidomimetic $^1$H-NMR Spectrum LCE00281: H-His-D-Trp-Ala-Trp-D-Phe-Dpr(4-FB)-$NH_2$.
Figure 35:
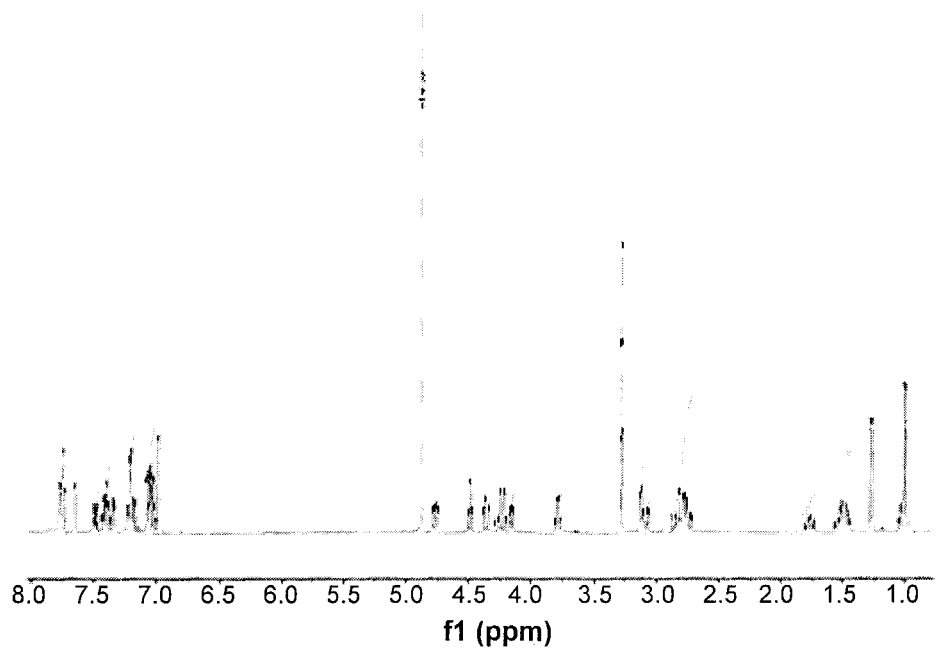
FIG. 35 Peptidomimetic $^1$H-NMR Spectrum LCE00282: H-D-Ala-D-2-Nal-Ala-Trp-D-Phe-Lys-$NH_2$.
Figure 36:
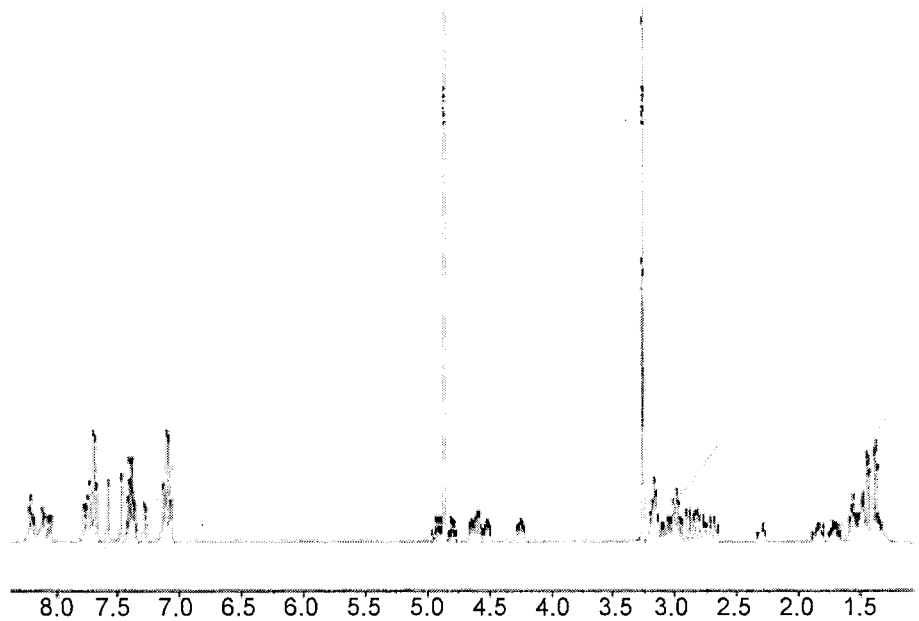
FIG. 36 Peptidomimetic $^1$H-NMR Spectrum LCE00295: H-Inp-D-2-Nal-D-2-Nal-Phe-Lys(2-FP)-$NH_2$.
Figure 37:
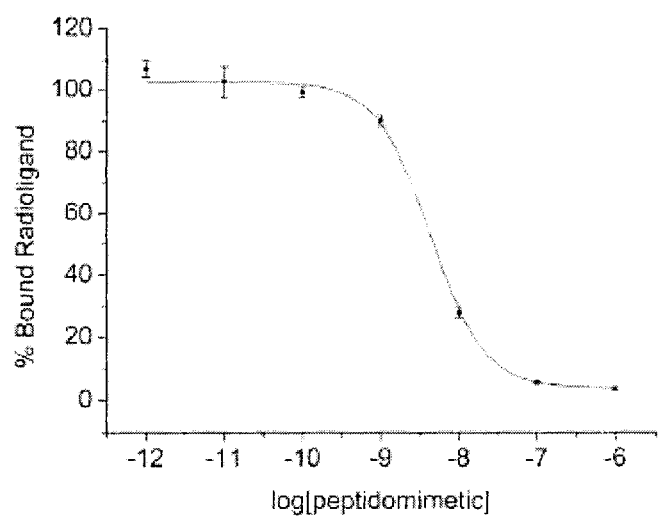
FIG. 37 Displacement curve for peptide standard ghrelin (1-28).
Figure 38A:
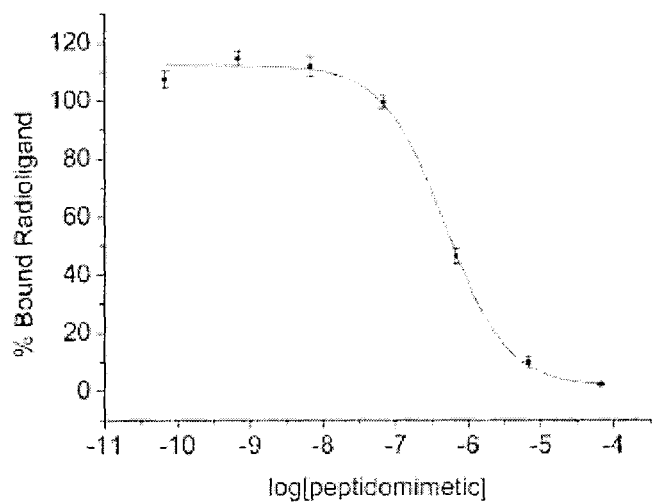
FIG. 38 Peptidomimetic displacement curve (A) LCE00210; (B) LCE00211.
Figure 38B:
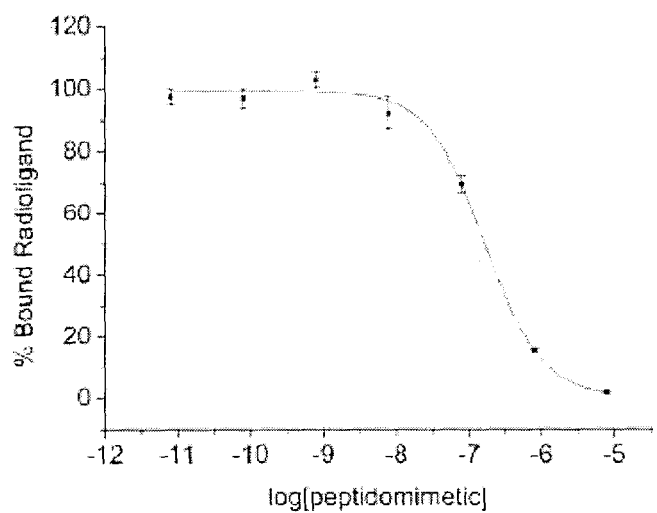
Figure 39A:
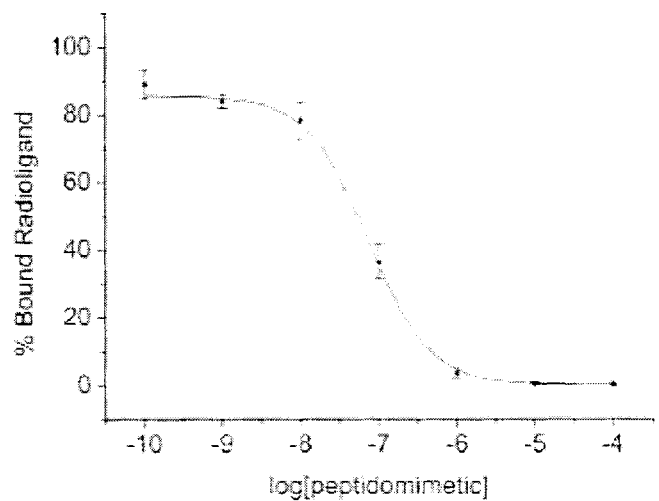
FIG. 39 Peptidomimetic displacement curve (A) LCE00239; (B) LCE00240.
Figure 39B:
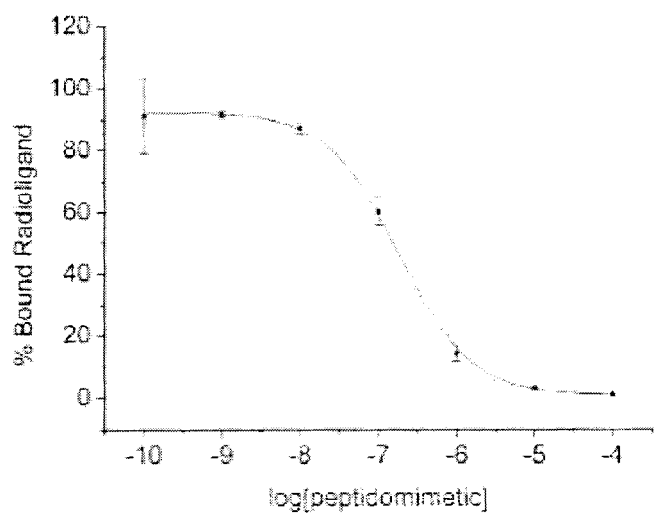
Figure 40A:
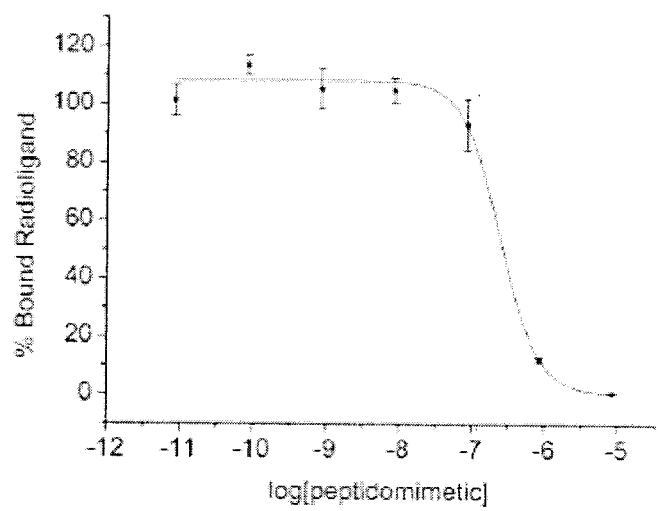
FIG. 40 Peptidomimetic displacement curve (A) LCE00243; (B) LCE00244.
Figure 40B:
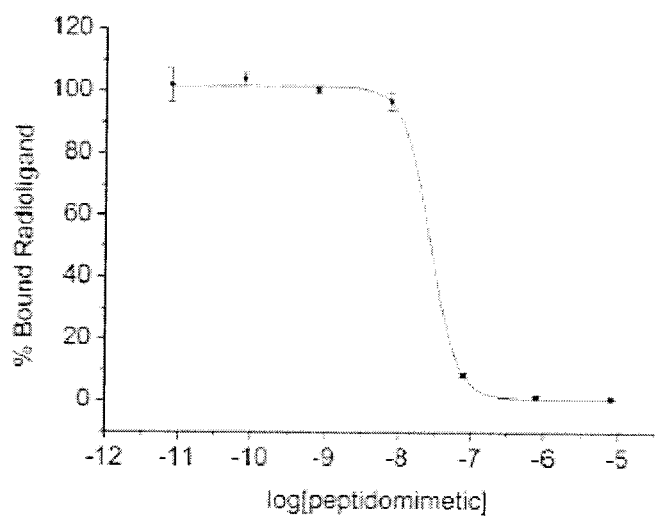
Figure 41A:
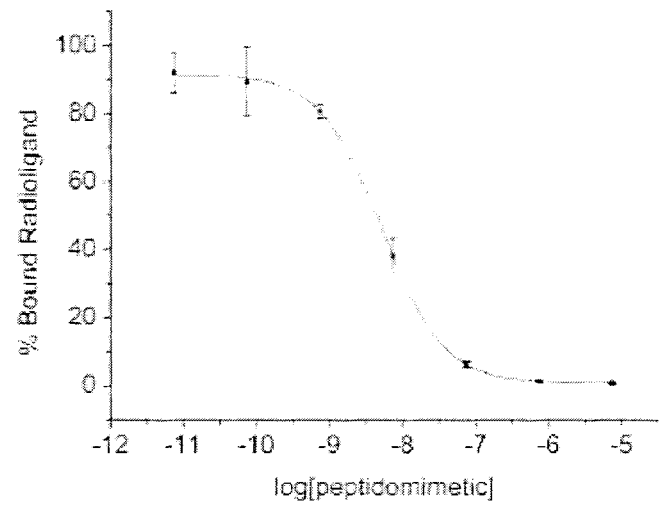
FIG. 41 Peptidomimetic displacement curve (A) LCE00245; (B) LCE00246.
Figure 41B:
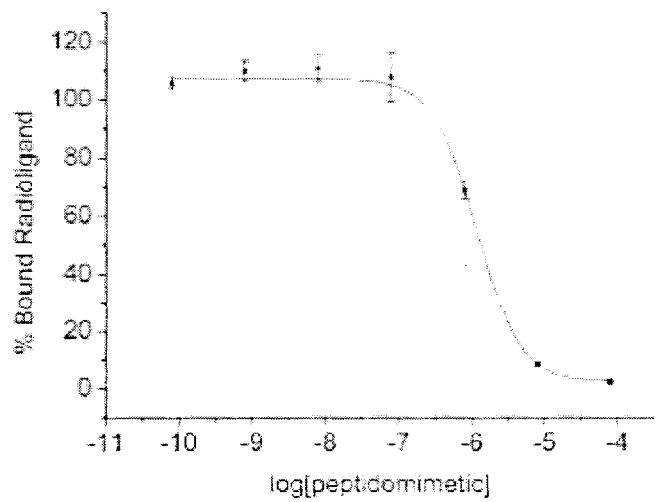
Figure 42A:
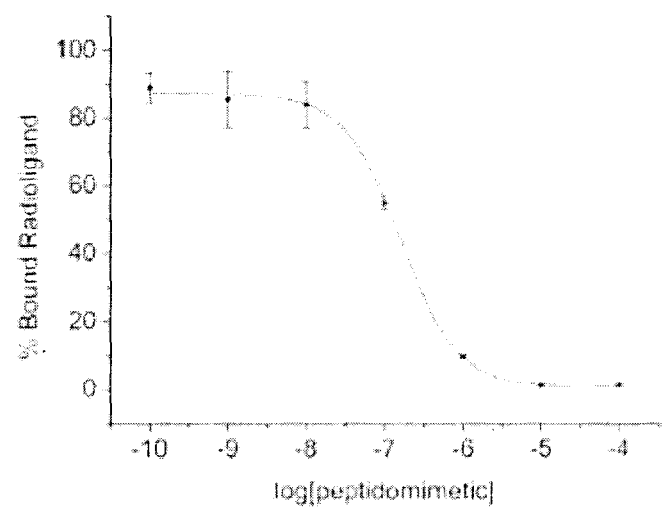
FIG. 42 Peptidomimetic displacement curve (A) LCE00267; (B) LCE00268.
Figure 42B:
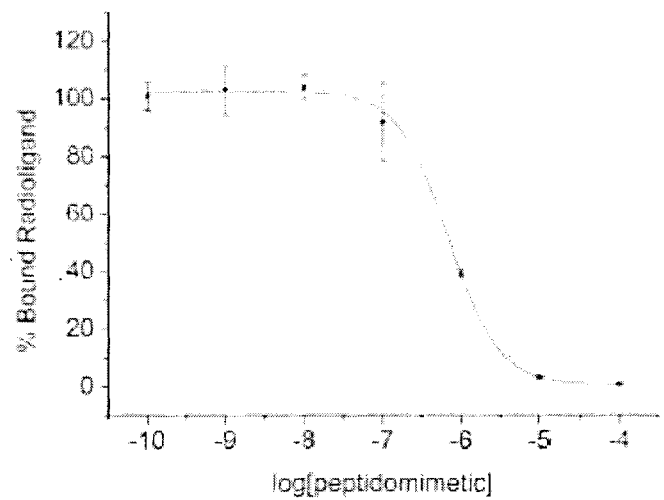
Figure 43A:
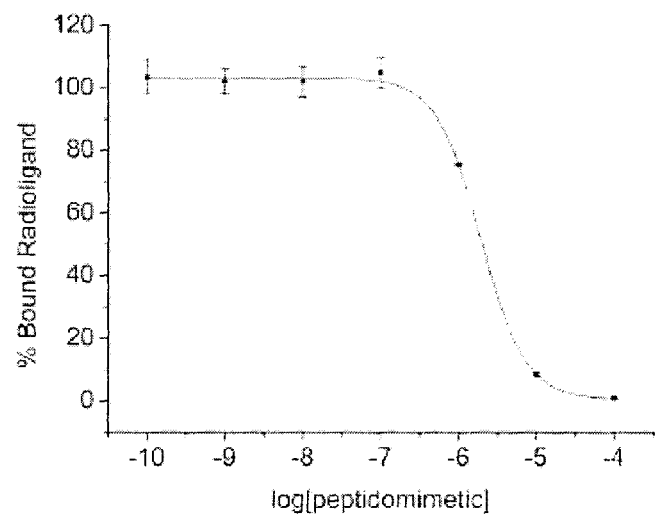
FIG. 43 Peptidomimetic displacement curve (A) LCE00269; (B) LCE00270.
Figure 43B:
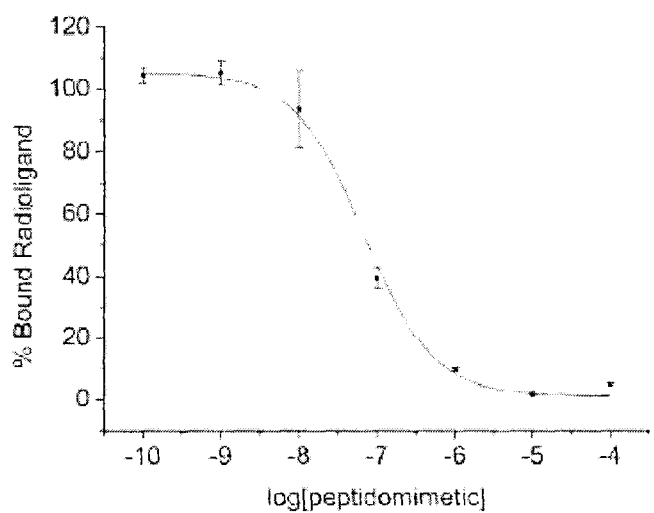
Figure 44A:
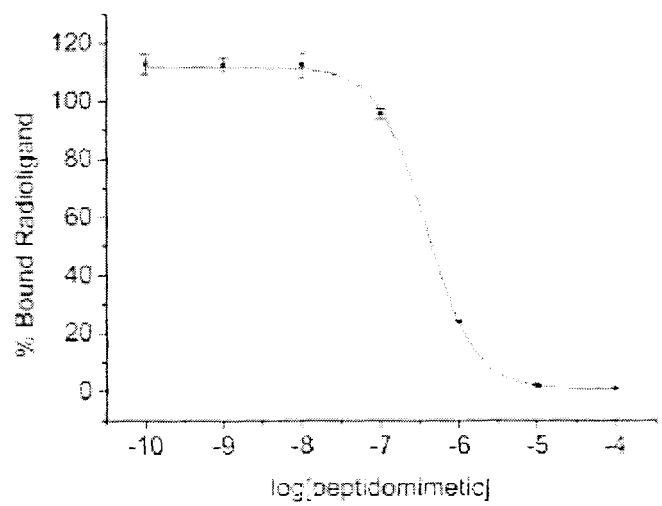
FIG. 44 Peptidomimetic displacement curve (A) LCE00272; (B) LCE00281.
Figure 44B:
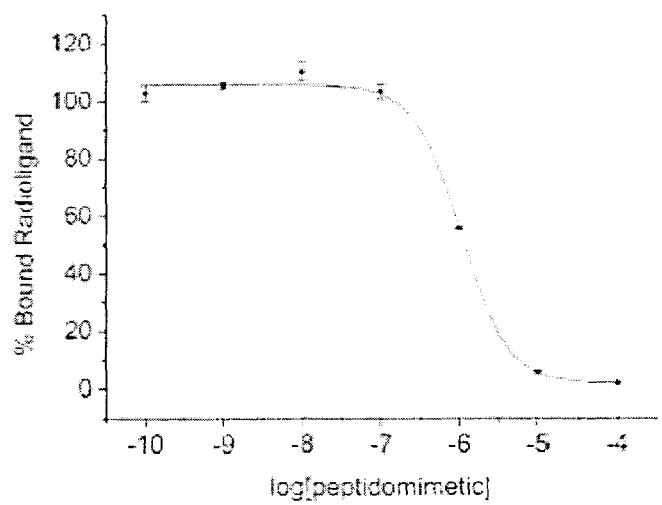
Figure 45:
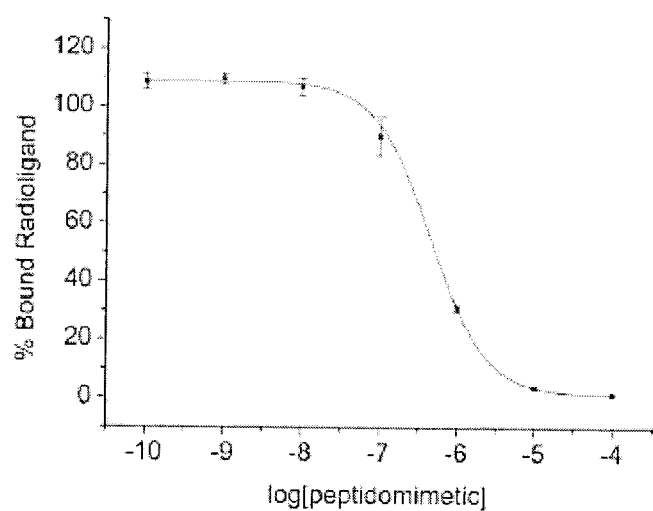
FIG. 45 Peptidomimetic displacement curve LCE00282.

An additional radiolabelling strategy for the highest affinity compound (2-FP-G-7039, LCE295) is proposed in the scheme illustrated in FIG. 10, where a direct labelling approach is used.

TABLE 1

Synthesized Compounds

| Name | Amino Acid Sequence | IC$_{50}$, nM | HRMS (calculated) | HRMS (found) | LCE no. | LogP (calc.) (ACD/Labs) |
|---|---|---|---|---|---|---|
| Ipamorelin | H-Aib-His-D-2-Nal-D-Phe-Lys-NH$_2$ | 483 | 712.3935 [M + H]$^+$ | 712.3959 | 210 | 1.72 ± 0.85 |
| 4-FB-Ipamorelin | H-Aib-His-D-2-Nal-D-Phe-Lys(4-FB)-NH$_2$ | 170 | 834.4103 [M + H]$^+$ | 834.4133 | 211 | 3.97 ± 0.89 |
| 4-FB-AEEA-Ipamorelin | H-Aib-His-D-2-Nal-D-Phe-Lys(4-FB-AEEA)-NH$_2$ | 474 | / | / | 217 | 2.80 ± 0.93 |
| Inp-Thi-4-FB-Ipamorelin | H-Inp-His-D-2-Nal-D-2-Thi-Lys(4-FB)-NH$_2$ | 1170 | 866.3824 [M + H]$^+$ | 866.3850 | 246 | 3.60 ± 0.89 |
| Thi-4-FB-Ipamorelin | H-Aib-His-D-2-Nal-D-2-Thi-Lys(4-FB)-NH$_2$ | 161 | 840.3667 [M + H]$^+$ | 840.3693 | 267 | 3.65 ± 0.90 |
| Inp-4-FB-Ipamorelin | H-Inp-His-D-2-Nal-D-Phe-Lys(4-FB)-NH$_2$ | 688 | 860.4259 [M + H]$^+$ | 860.4284 | 268 | 3.92 ± 0.89 |

TABLE 1-continued

Synthesized Compounds

| Name | Amino Acid Sequence | IC$_{50}$, nM | HRMS (calculated) | HRMS (found) | LCE no. | LogP (calc.) (ACD/Labs) |
|---|---|---|---|---|---|---|
| MMF-01-140-H | H-Inp-His-D-2-Nal-D-2-Nal-Lys(4-FB)-NH$_2$ | 1920 | 910.4416 [M + H]$^+$ | 910.4400 | 269 | 5.15 ± 0.89 |
| GHRP-6 | H-His-D-Trp-Ala-Trp-D-Ple-Lys-NH$_2$ | 73.1 | 873.4524 [M + H]$^+$ | 873.4531 | 239 | 1.51 ± 0.88 |
| 4-FB-GHRP-6 | H-His-D-Trp-Ala-Trp-D-Phe-Lys(4-FB)-NH$_2$ | 384 | 1017.4511 [M + H]$^+$ | 1017.4522 | 272 | 3.76 ± 0.92 |
| Dpr-4-FB-GHRP-6 | H-His-D-Trp-Ala-Trp-D-Phe-Dpr(4-FB)-NH$_2$ | 1060 | 953.4223 [M + H]$^+$ | 953.4237 | 281 | 3.86 ± 0.93 |
| GHRP-1 | H-Ala-His-D-2-Nal-Ala-Trp-D-Phe-Lys-NH$_2$ | 181 | 955.4943 [M + H]$^+$ | 955.4964 | 240 | 2.60 ± 0.90 |
| GHRP-2 | H-D-Ala-D-2-Nal-Ala-Trp-D-Phe-Lys-NH$_2$ | 449 | 840.4204 [M + H]$^+$ | 840.4173 | 282 | 3.41 ± 0.86 |
| G-7039 | H-Inp-D-2-Nal-D-2-Nal-Phe-Lys-NH$_2$ | 5.21 | 798.4343 [M + H]$^+$ | 798.4339 | 245 | 5.28 ± 0.82 |
| 4-FB-G-7039 | H-Inp-D-2-Nal-D-2-Nal-Phe-Lys(4-FB)-NH$_2$ | 242 | 920.4511 [M + H]$^+$ | 920.4529 | 243 | 7.53 ± 0.88 |
| 2-FP-G-7039 | H-Inp-D-2-Nal-D-2-Nal-Phe-Lys(2-FP)-NH$_2$ | 12 | / | / | 295 | 5.19 ± 0.88 |
| MMF-01-113-G | H-Inp-D-2-Nal-D-2-Nal-1-Nal-Lys-NH$_2$ | 27.6 | 848.4499 [M + H]$^+$ | 848.4501 | 244 | 6.51 ± 0.82 |
| MMF-01-115-H | H-Inp-D-2-Nal-D-2-Nal-1-Nal-Lys(4-FB)-NH$_2$ | 68.8 | 970.4667 [M + H]$^+$ | 970.4693 | 270 | 8.76 ± 0.88 |

Literature Compounds:

1. GHRP-6: H-His-D-Trp-Ala-Trp-D-Phe-Lys-NH$_2$
2. GHRP-1: H-Ala-His-D-2-Nal-Ala-Trp-D-Phe-Lys-NH$_2$
3. GHRP-2: H-D-Ala-D-2-Nal-Ala-Trp-D-Phe-Lys-NH$_2$
4. G-7039: H-Inp-D-2-Nal-D-2-Nal-Phe-Lys-NH$_2$
5. (inip) bb nPA K: H-Inp-D-2-Nal-D-2-Nal-1-Nal-Lys-NH$_2$
6. Ipamorelin: H-Aib-His-D-2-Nal-D-Phe-Lys-NH$_2$ Example 2

Using the compound G-7039 as a base, the novel conjugates of Table 2 were synthesized.

Figure 7:
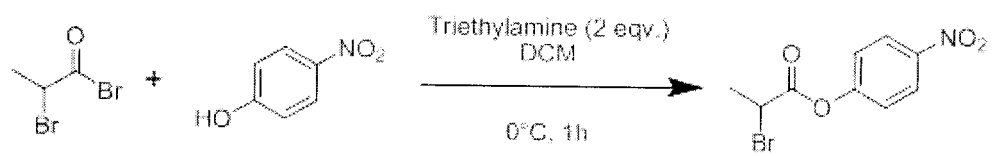
FIG. 7 Scheme showing the synthesis of 4-nitrophenyl 2-bromopropionate.
Figure 8:
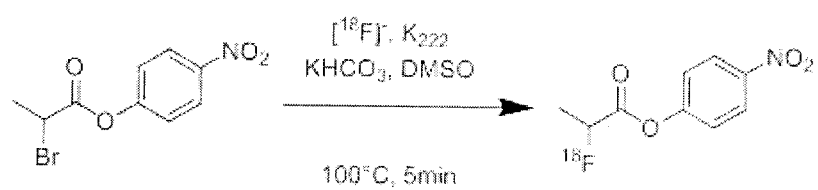
FIG. 8 Scheme showing the synthesis of $^{18}$F-labelled [Tyr$^4$, Lys$^5$(2-fluoropropionate)]G-7039 (also referred to as H-Inp-D-2-Nal-D-2-Nal-Tyr-Lys(2-FP)-NH2 or TL-MF-3-2FP (LCE No. 337).
Figure 8:
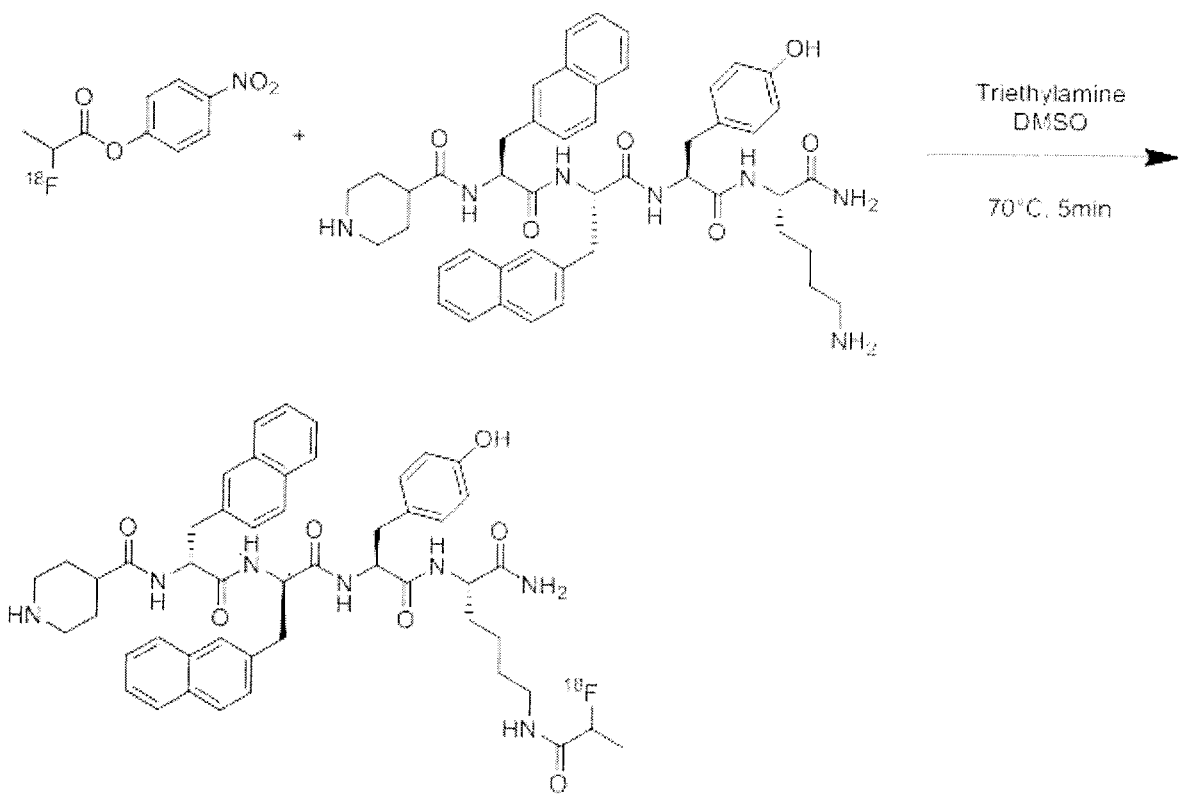
Figure 9:
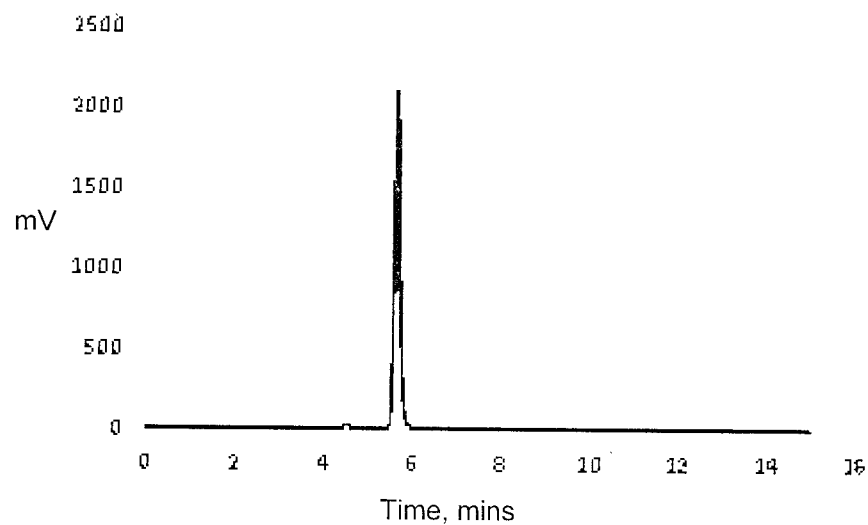
FIG. 9 Radio-chromatogram of the [$^{18}$F]SFB prosthetic group.

The synthesis of the precursor for obtaining TL-MF-3-2FP is shown in FIG. 7, while the synthesis of TL-MF-3-2FP is shown in FIG. 8.

Figure 47A:
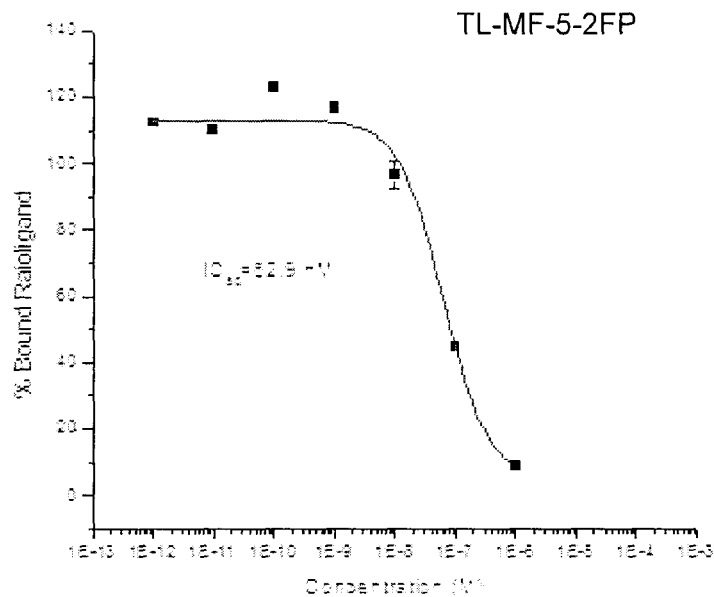
FIG. 47 Peptidomimetic displacement curve (A) TL-MF-5-2FP; (B) TL-MF-4-2FP.
Figure 47B:
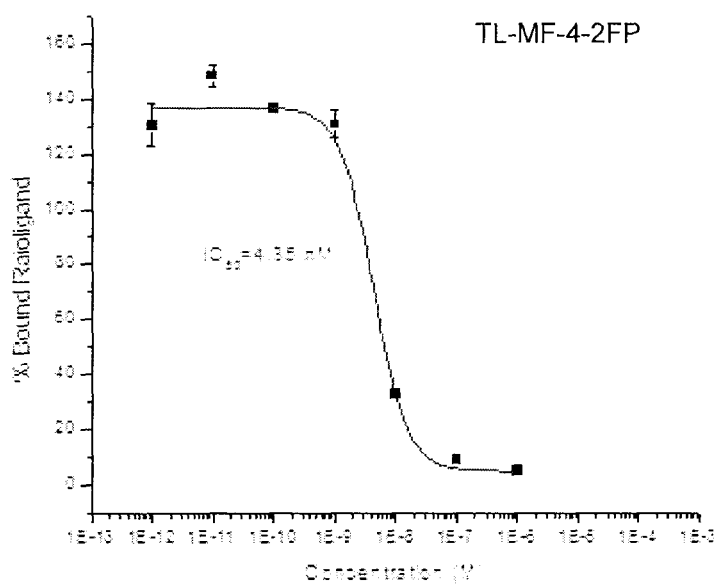
Figure 48A:
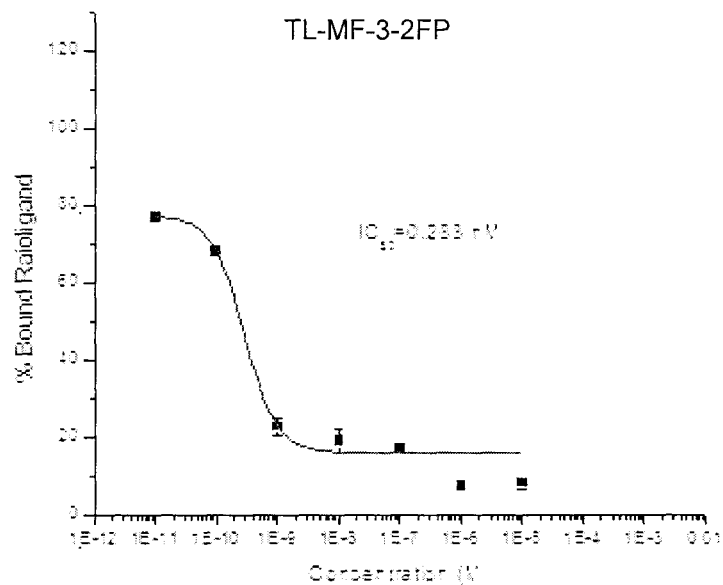
FIG. 48 Peptidomimetic displacement curve (A) TL-MF-3-2FP; (B) TL-MF-2-2FP.
Figure 48B:
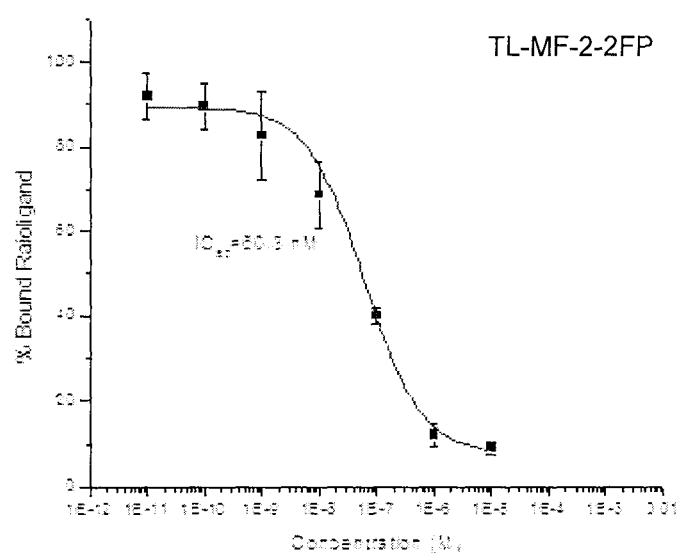
Figure 49A:
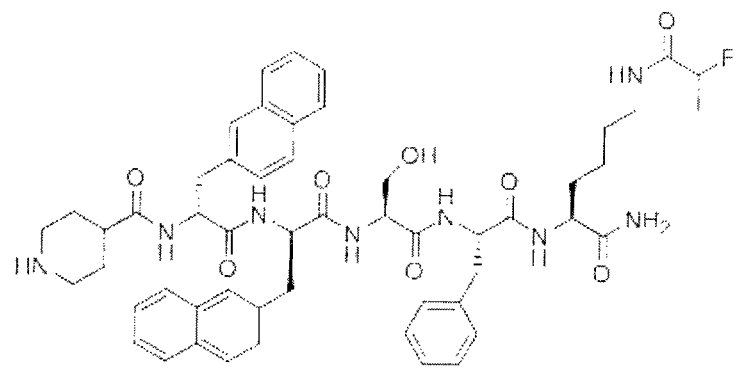
FIG. 49 Formula of (A) TL-MF-5-2FP and (B) TL-MF-4-2FP.
Figure 49B:
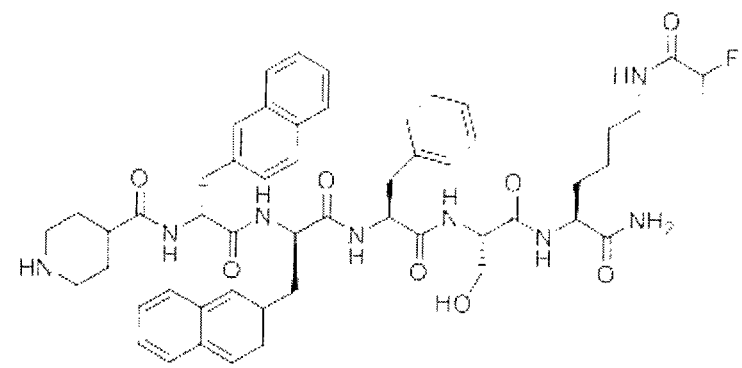
Figure 50A:
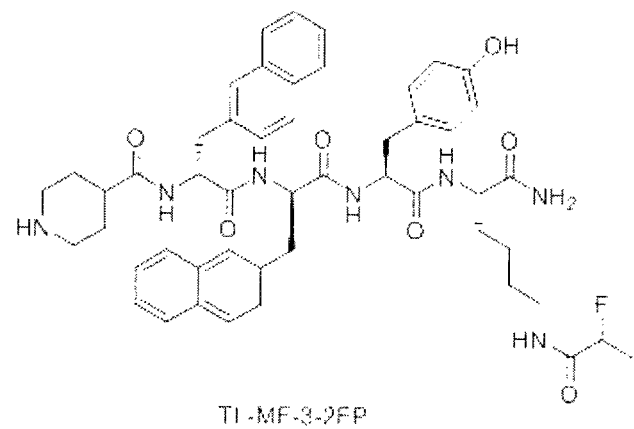
FIG. 50 Formula of (A) TL-MF-3-2FP and (B) TL-MF-2-2FP.
Figure 50B:
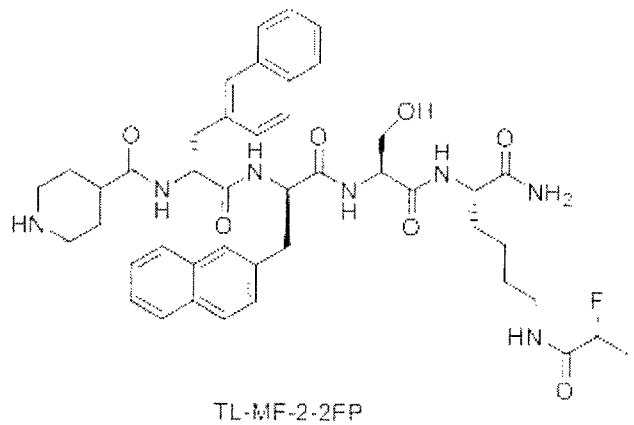

Competitive binding assays were run on the compounds of Table 2 as described in Example 1. The results of the competitive binding are shown in FIGS. 47-48. The formulas of the compounds of Table 2 are illustrated in FIGS. 49 and 50.

TABLE 2

Synthesized Compounds

| Compound | Amino Acid Sequence | IC$_{50}$ (nM) | HRMS (calculated) ([M + H]$^+$) | HRMS (found) ([M + H]$^+$) | LCE no. | LogP (calc.) (ACD/Labs) |
|---|---|---|---|---|---|---|
| TL-MF-5-2FP | H-Inp-(D-2-Nal)$_2$-Ser-Phe-Lys(2-FP)-NH$_2$ | 62.9 | 959.48 | 959.60 | LCE00335 | 4.34 +/− 0.90 |
| TL-MF-4-2FP | H-Inp-(D-2-Nal)$_2$-Phe-Ser-Lys(2-FP)-NH$_2$ | 4.35 | 959.48 | 959.60 | LCE00336 | 4.34 +/− 0.90 |
| TL-MF-3-2FP | H-Inp-D-2-Nal-D-2-Nal-Tyr-Lys(2-FP)-NH$_2$ | 0.283 | 888.44 | 888.32 | LCE00337 | 4.46 +/− 0.88 |

TABLE 2-continued

Synthesized Compounds

| Compound | Amino Acid Sequence | $IC_{50}$ (nM) | HRMS (calculated) ($[M + H]^+$) | HRMS (found) ($[M + H]^+$) | LCE no. | LogP (calc.) (ACD/Labs) |
|---|---|---|---|---|---|---|
| TL-MF-2-2FP | H-Inp-(D-2-Nal)$_2$-Ser-Lys(2-FP)-NH$_2$ | 60.3 | 812.41 | 812.41 | LCE00338 | 2.77 +/− 0.87 |

Example 3

Calcium Flux Assay

Another in vitro assay performed on the 4-fluorobenzoyl agonist [1-Nal$^4$,Lys$^5$(4-FB)]G-7039 and the [Lys$^5$(2-FP)]G-7039 agonist was a calcium flux dose-response assay. This experiment allows the determination of the half-maximal effective concentration ($EC_{50}$) for each agonist, a measure of the concentration of the agonist required to produce 50% of the maximum biological effect resulting from ghrelin receptor activation. In this particular case, the biological effect of the peptidomimetic [1-Nal$^4$,Lys$^5$(4-FB)]G-7039 and the peptidomimetic [Lys$^5$(2-FP)]G-7039 is the release of intracellular calcium ions, a process which is detected by fluorescence using a FLIPRTETRA instrument. Endogenous ghrelin was used as a control in this assay, which was performed by EMD Millipore's GPCRProfiler® service.

The calcium flux assay was carried out for both compounds [1-Nal$^4$,Lys$^5$(4-FB)]G-7039 (also referred to as 4-FBG-7039 in FIG. 51 and as compound MMF-01-115-H in Table 1) and in Lys$^5$(2-FP)]G-7039 (also referred to as compound 2-FP-G-7039 in Table 1) by the EMD Millipore GPCRProfiler® service. Samples of both compounds were dissolved in DMSO (1 ml) at a concentration of 250 μM and solubility tested in the recommended buffer (Hanks balanced salt solution: 1.26 mM CaCl$_2$, 0.493 mM MgCl$_2$.6H$_2$O, 0.407 mM MgSO$_4$.7H$_2$O, 5.33 mM KCl, 0.441 mM KH$_2$PO$_4$, 4.17 mM NaHCO$_3$, 137.9 mM NaCl, 0.338 mM Na$_2$HPO4, 5.56 mM D-Glucose with 20 mM HEPES, pH=7.4 and final concentration of 1.2% DMSO). If the compound remained soluble 15 minutes after addition, samples were shipped to the EMD Millipore Corporation (15 Research Park Drive, St. Charles, Mo. 63304, USA). The assay service calculated $EC_{50}$ values for both peptidomimetics as well as the ghrelin control in terms of intracellular $Ca^{2+}$ release. Human recombinant ghrelin receptor calcium-optimized stable cell lines (chem-1 cells) were loaded with a fluorescent calcium dye (Fluo-8 NW from ABD Bioquest 21080) and calcium flux detected in response to the agonists by a Molecular Devices FLIPR$^{TETRA}$ instrument. The agonist assay was performed for a total of 180 seconds. Each assay and assay concentration was performed in duplicate. The data acquired is presented in FIG. 51 ([1-Nal$^4$,Lys$^5$(4-FB)]G-7039) and FIG. 52 (Lys$^5$(2-FP)]G-7039).

The control ligand ghrelin was found to have a high in vitro potency ($EC_{50}$=1.6 nM), which is expected for the endogenous ligand of the GHS-R1a. The $EC_{50}$ value of [1-Nal$^4$,Lys$^5$(4-FB)]G-7039 was found to be 1.1 nM. This demonstrates that the presence of the 4-fluorobenzoyl group still results in a low nanomolar efficacy. This is in spite of the slight increase in the $IC_{50}$ value compared to the compound [1-Nal$^4$]G-7039 ($IC_{50}$=69 nM vs 28 nM respectively). The high in vitro potency acquired for [1-Nal$^4$,Lys$^5$(4-FB)]G-7039 indicates that it is a potent ghrelin receptor agonist.

The $EC_{50}$ value for Lys$^5$(2-FP)]G-7039 was found to be 20 pM or 0.02 nM, which is an exceptionally high efficacy for this peptidomimetic agonist. This is an unexpected improvement in efficacy as compared to the reported half-maximal efficacy of the parent compound G-7039 ($EC_{50}$=0.18 nM) (Elias, K., et al., Endocrinology 1995, 136, 5694-5699) despite the different mode of potency determination ($Ca^{2+}$ release for [Lys$^5$(2-FP)]G-7039 but GH release for G-7039).

Advantages

The peptidomimetics of the present invention are different from existing technology in that it attempts to distinguish between malignant and benign tumours by targeting the ghrelin receptor, which is known to have a differential expression in benign and malignant tumours compare to, for example, normal prostetic tissue. This is an issue prevalent with imaging modalities in current clinical use (18F- and 11C-PET CT, PET/CT, MRI and mpMRI). There are currently no clinical imaging agents targeting specific receptors for prostate cancer imaging. In addition, the use of peptidomimetics represents superior targeting, stability and pharmacokinetic properties compared to peptide-based approaches.

REFERENCES (1) Bowers, C. Y.; Chang, J.; Momany, F.; Folkers, K. Mol. Endocrinol. Proc. 1977, 287-292.
(2) Bowers, C. Y.; Momany, F. A.; Reynolds, G. A.; Hong, A. Endocrinology 1984, 114, 1537-1545.
(3) Bowers, C. Y. J. Pediatr. Endocrinol. 1993, 6, 21-31.
(4) Ilson, B. E.; Jorkasky, D. K.; Curnow, R. T.; Stote, R. M. J. Clin. Endocrinol. Metab. 1989, 69, 212-214.
(5) Moulin, A.; Ryan, J.; Martinez, J.; Fehrentz, J. Chem Med Chem 2007, 2, 1242-1259.
(6) Akman, M. S.; Girard, M.; O'Brien, L. F.; Ho, A. K.; Chik, C. L. Endocrinology 1993, 132, 1286-1291.
(7) Isidro, M. L.; Cordido, F. Comb. Chem. High Throughput Screening 2006, 9, 175-180.
(8) Smith, R. G.; Cheng, K.; Schoen, W., R.; Pong, S. S.; Hickey, G.; Jacks, T.; Butler, B.; Chan, W. W. S.; Chaung, L. Y. P.; et al Science 1993, 260, 1640-1643.
(9) Conley, L. K.; Giustina, A.; Imbimbo, B. P.; Stagg, L. C.; Deghenghi, R.; Wehrenberg, W. B. Endocrine 1994, 2, 691-695.
(10) Patchett, A. A.; Nargund, R. P.; Tata, J. R.; Chen, M. -.; Barakat, K. J.; Johnston, D. B. R.; Cheng, K.; Chan, W. W. -.; Butler, B.; et al Proc. Natl. Acad. Sci. 1995, 92, 7001-7005.
(11) Deghenghi, R.; Cananzi, M. M.; Torsello, A.; Battisti, C.; Muller, E. E.; Locatelli, V. Life Sci. 1994, 54, 1321-1328.

(12) Elias, K.; Ingle, G.; Burnier, J.; Hammonds, R.; Mcdowell, R.; Rawson, T.; Somers, T.; Stanley, M.; Cronin, M. *Endocrinology* 1995, 136, 5694-5699.

(13) Muccioli, G.; Broglio, F.; Tarabra, E.; Ghigo, E. *Endocr. Updates* 2004, 23, 27-45.

(14) Howard, A. D.; Feighner, S. D.; Cully, D. F.; Arena, J. P.; Liberator, P. A.; Rosenblum, C. I.; Hamelin, M.; Hreniuk, D. L.; Palyha, O. C.; et al *Science* 1996, 273, 974-977.

(15) Kojima, M.; Hosoda, H.; Date, Y.; Nakazato, M.; Matsuo, H.; Kangawa, K. *Nature* 1999, 402, 656-660.

(16) Bednarek, M. A.; Feighner, S. D.; Pong, S.; McKee, K. K.; Hreniuk, D. L.; Silva, M. V.; Warren, V. A.; Howard, A. D.; Van der Ploeg, L. H. Y.; Heck, J. V. *J. Med. Chem.* 2000, 43, 4370-4376.

(17) Torsello, A.; Ghe, C.; Bresciani, E.; Catapano, F.; Ghigo, E.; Deghenghi, R.; Locatelli, V.; Muccioli, G. *Endocrinology* 2002, 143, 1968-1971.

(18) Ye, Z.; Gao, Y.; Bakshi, R. K.; Chen, M.; Rohrer, S. P.; Feighner, S. D.; Pong, S.; Howard, A. D.; Blake, A.; Birzin, E. T.; Locco, L.; Parmar, R. M.; Chan, W. W. -.; Schaeffer, J. M.; Smith, R. G.; Patchett, A. A.; Nargund, R. P. *Bioorg. Med. Chem. Lett.* 2000, 10, 5-8.

(19) Li, J. J.; Wang, H.; Li, J.; Qu, F.; Swartz, S. G.; Hernandez, A. S.; Biller, S. A.; Robl, J. A.; Tino, J. A.; Slusarchyk, D.; Seethala, R.; Sleph, P.; Yan, M.; Grover, G.; Flynn, N.; Murphy, B. J.; Gordon, D. *Bioorg. Med. Chem. Lett.* 2008, 18, 2536-2539.

(20) Tokunaga, T.; Hume, W. E.; Nagamine, J.; Kawamura, T.; Taiji, M.; Nagata, R. *Bioorg. Med. Chem. Lett.* 2005, 15, 1789-1792.

(21) Raun, K.; Hansen, B. S.; Johansen, N. L.; Thogersen, H.; Madsen, K.; Ankersen, M.; Andersen, P. H. *Eur. J. Endocrinol.* 1998, 139, 552-561.

(22) Ankersen, M.; Johansen, N. L.; Madsen, K.; Hansen, B. S.; Raun, K.; Nielsen, K. K.; Thogersen, H.; Hansen, T. K.; Peschke, B.; Lau, J.; Lundt, B. F.; Andersen, P. H. *J. Med. Chem.* 1998, 41, 3699-3704.

(23) Hansen, T. K.; Ankersen, M.; Hansen, B. S.; Raun, K.; Nielsen, K. K.; Lau, J.; Peschke, B.; Lundt, B. F.; Thogersen, H.; Johansen, N. L.; Madsen, K.; Andersen, P. H. *J. Med. Chem.* 1998, 41, 3705-3714.

(24) Ankersen, M.; Hansen, B. S.; Hansen, T. K.; Lau, J.; Peschke, B.; Madsen, K.; Johansen, N. L. *Eur. J. Med. Chem.* 1999, 34, 783-790.

(25) Hansen, B.; Raun, K.; Nielsen, K.; Johansen, P.; Mansen, T.; Peschke, B.; Lau, J.; Andersen, P.; Ankersen, M. *Eur. J. Endocrinol.* 1999, 141, 180-189.

(26) Peschke, B.; Ankersen, M.; Hansen, B.; Hansen, T.; Johansen, N.; Lau, J.; Madsen, K.; Petersen, H.; Thogersen, H.; Watson, B. *Eur. J. Med. Chem.* 1999, 34, 363-380.

(27) Peschke, B.; Hansen, B. S. *Bioorg. Med. Chem. Lett.* 1999, 9, 1295-1298.

(28) Ankersen, M.; Nielsen, K. K.; Hansen, T. K.; Raun, K.; Hansen, B. S. *Eur. J. Med. Chem.* 2000, 35, 487-497.

(29) Peschke, B.; Ankersen, M.; Hansen, T. K.; Hansen, B. S.; Lau, J.; Nielsen, K. K.; Raun, K. *Eur. J. Med. Chem.* 2000, 35, 599-618.

(30) Hansen, T.; Ankersen, M.; Raun, K.; Hansen, B. *Bioorg. Med. Chem. Lett.* 2001, 11, 1915-1918.

(31) Peschke, B.; Ankersen, M.; Bauer, M.; Hansen, T. K.; Hansen, B. S.; Nielsen, K. K.; Raun, K.; Richter, L.; Westergaard, L. *Eur. J. Med. Chem.* 2002, 37, 487-501.

(32) Muccioli, G.; Tschop, M.; Papotti, M.; Deghenghi, R.; Heiman, M.; Ghigo, E. *Eur. J. Pharmacol.* 2002, 440, 235-254.

(33) Broglio, F.; Guarracino, F.; Benso, A.; Gottero, C.; Prodam, F.; Granata, R.; Avogadri, E.; Muccioli, G.; Deghenghi, R.; Ghigo, E. *Eur. J. Pharmacol.* 2002, 448, 193-200.

(34) Jeffery, P. L.; Herington, A. C.; Chopin, L. K. *J. Endocrinol.* 2002, 172, R7-R11.

(35) Lu, C.; McFarland, M. S.; Nesbitt, R.; Williams, A. K.; Chan, S.; Gomez-Lemus, J.; Autran-Gomez, A. M.; Al-Zahrani, A.; Chin, J. L.; Izawa, J. I.; Luyt, L. G.; Lewis, J. D. *The Prostate* 2012, 72, 825-833.

(36) Jemal, A.; Siegel, R.; Xu, J.; Ward, E. *CA Cancer J. Clin.* 2010, 60, 277-300.

(37) The Canadian Cancer Society Prostate Cancer Risks. http://www.cancer.ca/en/cancer-information/cancer-type/prostate/risks/?region=on (accessed May 25, 2013, 2013).

(38) Seitz, M.; Shukla-Dave, A.; Bjartell, A.; Touijer, K.; Sciarra, A.; Bastian, P. J.; Stief, C.; Hricak, H.; Graser, A. *Eur. Urol.* 2009, 55, 801-814.

(39) Kattan, M. W.; Eastham, J. A.; Stapleton, A. M.; Wheeler, T. M.; Scardino, P. T. *J Natl Cancer Inst* 1998, 90, 766-771.

(40) Eifler, J. B.; Feng, Z.; Lin, B. M.; Partin, M. T.; Humphreys, E. B.; Han, M.; Epstein, J. I.; Walsh, P. C.; Trock, B. J.; Partin, A. W. *BJU Int* 2013, 111, 22-29.

(41) D'Amico, A. V.; Whittington, R.; Malkowicz, S. B.; Schultz, D.; Blank, K.; Broderick, G. A.; Tomaszewski, J. E.; Renshaw, A. A.; Kaplan, I.; Beard, C. J.; Wein, A. *Jama* 1998, 280, 969-974.

(42) Gupta, R. T.; Kauffman, C. R.; Polascik, T. J.; Taneja, S. S.; Rosenkrantz, A. B. *Oncology (Williston Park)* 2013, 27, 262-270.

(43) Turkbey, B.; Mani, H.; Shah, V.; Rastinehad, A. R.; Bernardo, M.; Pohida, T.; Pang, Y.; Daar, D.; Benjamin, C.; McKinney, Y. L.; Trivedi, H.; Chua, C.; Bratslaysky, G.; Shih, J. H.; Linehan, W. M.; Merino, M. J.; Choyke, P. L.; Pinto, P. A. *J Urol* 2011, 186, 1818-1824.

(44) Thormer, G.; Otto, J.; Reiss-Zimmermann, M.; Seiwerts, M.; Moche, M.; Garnov, N.; Franz, T.; Do, M.; Stolzenburg, J.; Horn, L.; Kahn, T.; Busse, H. *Eur Radiol* 2012, 22, 1820-1828.

(45) Jadvar, H. *J. Nucl. Med* 2011, 52, 81-89.

(46) Fuchsjager, M.; Shukla-Dave, A.; Akin, O.; Barentsz, J.; Hricak, H. *Acta Radiol* 2008, 49, 107-120.

(47) Schwarzenboeck, S.; Souvatzoglou, M.; Krause, B. J. *Theranostics* 2012, 2, 318-330.

(48) Warburg, O. *Science* 1956, 123, 309-314.

(49) Fanti, S.; Nanni, C.; Ambrosini, V.; Gross, M. D.; Rubello, D.; Farsad, M. *Q J Nucl Med Mol Imaging* 2007, 51, 260-271.

(50) Kato, T.; Tsukamoto, E.; Kuge, Y.; Takei, T.; Shiga, T.; Shinohara, N.; Katoh, C.; Nakada, K.; Tamaki, N. *Eur. J. Nucl. Med. Mol. Imaging* 2002, 29, 1492-1495.

(51) Watanabe, H.; Kanematsu, M.; Kondo, H.; Kako, N.; Yamamoto, N.; Yamada, T.; Goshima, S.; Hoshi, H.; Bae, K. T. *J Magn Reson Imaging* 2010, 31, 1151-1156.

(52) Shiiba, M.; Ishihara, K.; Kimura, G.; Kuwako, T.; Yoshihara, H.; Yoshihara, N.; Sato, H.; Kondo, Y.; Tsuchiya, S.; Kumita, S. *Ann Nucl Med* 2012, 26, 138-145.

(53) Pretka, J. E.; Lindwall, H. G. *J. Org. Chem.* 1954, 19, 1080-1088.

Through the embodiments that are illustrated and described, the currently contemplated best mode of making and using the invention is described. Without further elaboration, it is believed that one of ordinary skill in the art can, based on the description presented herein, utilize the present invention to the full extent. Future applications claiming priority to this application may or may not include the following claims, and may include claims broader, narrower, or entirely different from the following claims.

What is claimed is:

1. A compound comprising the sequence H-Inp-D-2-Nal-D-2-Nal-Xaa-Aaa-NH$_2$,
  wherein Aaa is a (a) Lys, or (b) a Lys(azide), or (c) a Lys conjugated to a detectable label, or (d) a Lys(azide) conjugated to a detectable label, and
wherein Xaa is 1 or 2 variable amino acid residues,
wherein when Xaa is 1 variable amino acid, then Xaa is Ser or Tyr, with the proviso that when Aaa is (a) Lys, then Xaa is Ser, and
when Xaa is 2 variable amino acid residues, then at least one Xaa is Tyr or Ser.

2. The compound of claim 1, wherein the Aaa is Lys (azide).

3. The compound of claim 1, wherein the compound comprises a formula selected from the group of formulae consisting of:

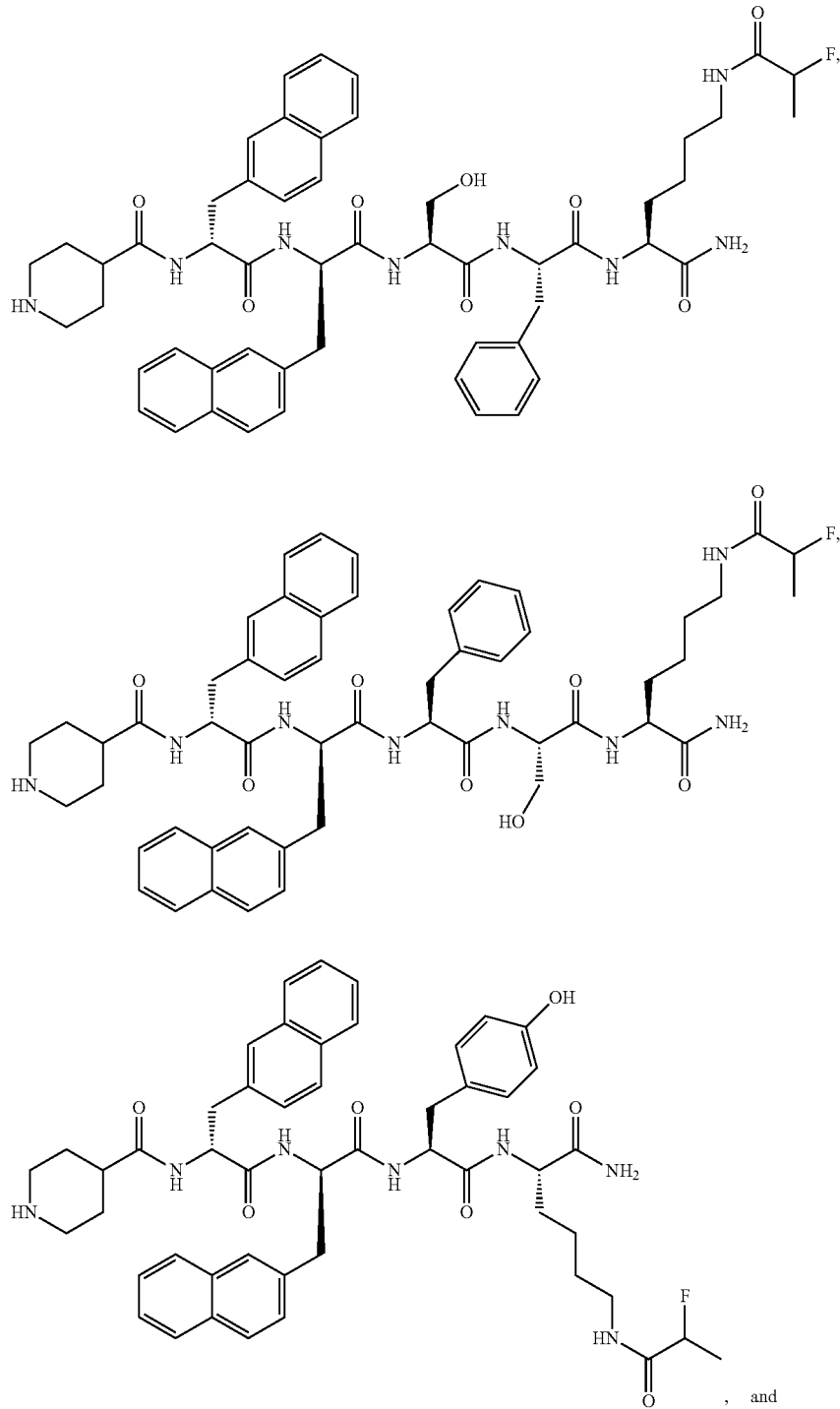

, and

-continued

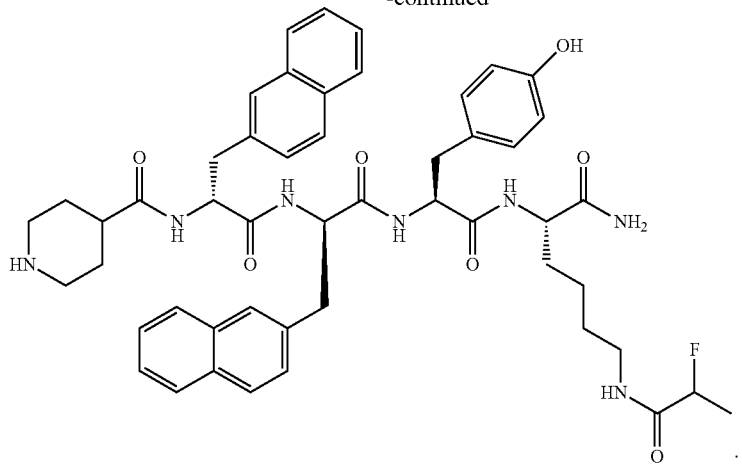

4. The compound of claim 1, wherein the a detectable label is 2-fluoropropionyl (2-FP).

5. The compound of claim 1, wherein the detectable label is a fluorine or a fluorine-containing group.

6. The compound of claim 1, wherein the Aaa is Lys.

7. The compound of claim 5, wherein the fluorine or the fluorine-containing group is radioactive.

8. The compound of claim 1, wherein the compound is H-Inp-(D-2-Nal)$_2$-Ser-Phe-Lys(2-FP)-NH$_2$, H-Inp-(D-2-Nal)$_2$-Phe-Ser-Lys(2-FP)-NH$_2$, H-Inp-(D-2-Nal)$_2$-Tyr-Lys(2-FP)-NH$_2$ or H-Inp-(D-2-Nal)$_2$-Ser-Lys(2-FP)-NH$_2$.

9. A method of detecting ghrelin (GHSR-1a) receptors at a target site of a subject, the method comprising:
 (a) providing the compound as described in claim 1;
 (b) administering a concentration of the compound of step (a) to the subject effective to detect the ghrelin (GHSR-1a) receptors at the target site; and
 (c) detecting the compound at the target site thereby detecting the ghrelin (GHSR-1a) receptors at the target site wherein the detecting is performed with positron emission tomography (PET), PET-computed tomography (CT) hybrid or PET-magnetic resonance imaging (MRI) hybrid.

10. The method of claim 9, wherein the target site is a tumor.

11. The method of claim 9, wherein the target site is a cardiac tissue.

12. The method of claim 10, further comprising:
 (d) comparing an expression of the GHSR-1a receptors in the detection of step (c) with the expression of ghrelin (GHSR-1a) receptors in a benign tumor control tissue, and
 (e) assessing a malignancy of the tumor based on the comparison, wherein a higher expression of the GHSR-1a receptors in the target site compared to the benign tumor control tissue is indicative of malignancy.

13. A pharmaceutical composition comprising the compound as defined in claim 1, and a pharmaceutically acceptable carrier.

14. A method of increasing the level of endogenous growth hormone in a subject comprising administering to the subject a pharmaceutically effective amount of the pharmaceutical composition of claim 13.

15. The method of claim 14, wherein the subject suffers of cancer, cachexia, gastrointestinal motility, ulcers or gastroparesis, anorexia nervosa, heart failure, diabetes mellitus, constipation or Parkinson's disease.

16. The compound of claim 1, wherein when Xaa is 2 variable amino acid residues, then one Xaa is Tyr or Ser and the other Xaa is selected from the group consisting of 1-Nal, Tyr, Phe and Ser.

17. The compound of claim 1, wherein Xaa is Ser.

18. The compound of claim 4, wherein the 2-FP is radioactive.

19. A method of imaging a target tissue in a subject, the method comprising:
 (a) contacting the target tissue with the compound of claim 1; and
 (b) imaging the target tissue in the subject, wherein the imaging is performed with positron emission tomography (PET), PET-computed tomography (CT) hybrid or PET-magnetic resonance imaging (MRI) hybrid.

20. A method of diagnosing cancer in a target site of a subject, the method comprising:
 (a) contacting the target site with the compound of claim 1;
 (b) detecting the expression of the compound in the target site, wherein the detecting is performed with positron emission tomography (PET), PET-computed tomography (CT) hybrid or PET-magnetic resonance imaging (MRI) hybrid; and
 (c) comparing the expression of step (b) with the expression of the compound in a control normal tissue or a control cancer tissue, wherein a higher expression of the compound in the target site relative to the control normal tissue, or a similar or higher expression of the compound in the target site relative to the control cancer tissue is indicative of cancer diagnosis in the subject.

* * * * *